(12) United States Patent
Deschenes et al.

(10) Patent No.: US 7,883,860 B2
(45) Date of Patent: Feb. 8, 2011

(54) HUMAN PROTEIN ACYL TRANSFERASES AND METHODS OF USES THEREFOR

(75) Inventors: Robert J. Deschenes, Brookfield, WI (US); Sandra Lobo, Eden Prairie, MN (US); John Swarthout, St. Louis, MO (US); Maurine E. Linder, University City, MO (US)

(73) Assignees: Washington University, St. Louis, MO (US); The University of Iowa Research Foundation, Iowa City, IA (US)

( * ) Notice: Subject to any disclaimer, the term of this patent is extended or adjusted under 35 U.S.C. 154(b) by 106 days.

(21) Appl. No.: 12/346,556

(22) Filed: Dec. 30, 2008

(65) Prior Publication Data

US 2009/0208990 A1    Aug. 20, 2009

Related U.S. Application Data

(62) Division of application No. 10/947,052, filed on Sep. 22, 2004, now Pat. No. 7,488,592.

(60) Provisional application No. 60/505,631, filed on Sep. 24, 2003.

(51) Int. Cl.
*C12Q 1/68* (2006.01)
*G01N 33/53* (2006.01)
*G01N 33/537* (2006.01)

(52) U.S. Cl. .................. 435/7.92; 435/15; 435/193; 536/23.2

(58) Field of Classification Search ................. None
See application file for complete search history.

*Primary Examiner*—Manjunath N Rao
*Assistant Examiner*—Kagnew H Gebreyesus

(57) ABSTRACT

The present invention provides the identification of human Ras palmitoyl acyl transfersase complexes, and nucleic acids coding therefor. In addition, methods of screening for modulators of human Ras palmitoyl acyl transfersase, including high throughput yeast screens, are also provided.

15 Claims, 20 Drawing Sheets

(A)
ERF2 (YLR246W) Gene sequence Length: 1080

```
   1  ATGGCCTTGG  TCTCTAGAAG  GTCGACAAGA  TCGGAAAGCA  CCTCAATAAC
  51  AAAGGAAGAG  CATACAGGAG  AAGGTTCATT  GACGAAGTTG  TTCTTCCGAT
 101  GGCTTGTTAC  CTTGGAGGGT  GATCAGGATA  TAAACGATGG  AAAAGGTTAT
 151  ATATCGTTAC  CGAATGTCTC  GAATTATATA  TTCTTCCTTG  GTGGCAGGTT
 201  CAGGACAGTA  AAGGGCGCCA  AACCGTTGTG  GTTAGGTGTT  CTCCTTGCTA
 251  TTGTATGTCC  CATGGTTCTC  TTCTCCATAT  TTGAGGCTCA  CAAATTGTGG
 301  CATACCCAAA  ATGGTTATAA  AGTGCTGGTC  ATTTTCTTCT  ATTATTTTTG
 351  GGTCATAACG  CTAGCATCCT  TTATCAGAAC  AGCCACTAGT  GATCCTGGCG
 401  TTCTTCCGAG  AAATATTCAT  TTAAGTCAAC  TAAGAAATAA  TTATCAGATC
 451  CCGCAAGAAT  ATTACAACTT  GATAACACTA  CCAACACATT  CTTCAATTTC
 501  AAAAGACATT  ACTATCAAGT  ATTGTCCATC  ATGTAGGATA  TGGAGACCAC
 551  CTCGGTCTTC  TCACTGTTCC  ACATGTAACG  TCTGCGTAAT  GGTTCATGAC
 601  CACCATTGCA  TATGGGTCAA  TAATTGCATA  GGAAAAAGGA  ACTACCGGTT
 651  CTTTTTAATA  TTCCTGTTAG  GTGCAATACT  TTCGTCCGTC  ATATTATTAA
 701  CTAATTGTGC  CATCCATATT  GCACGGGAAT  CAGGGGGGCC  TCGCGATTGT
 751  CCCGTTGCAA  TATTGTTACT  TTGCTATGCA  GGGCTAACCT  TATGGTATCC
 801  GGCAATACTG  TTTACTTATC  ACATATTTAT  GGCAGGTAAT  CAGCAAACAA
 851  CAAGGGAATT  TTTGAAAGGT  ATTGGATCGA  AAAAAAACCC  TGTATTCCAT
 901  CGTGTGGTCA  AGGAGGAAAA  CATATATAAT  AAGGGGTCCT  TTTTGAAAAA
 951  TATGGGTCAC  TTGATGTTAG  AACCAAGGGG  CCCAAGCTTT  GTAAGTGCCA
1001  GAAAGCCACA  TGAAGCTGGA  GATTGGAGAT  TTATGGATTT  ATCGCCAGCA
1051  CACAGCTTTG  AAAAAATACA  GAAATATAA
```

(B)
Erf2 (YLR246W) Protein sequence

```
   1  MALVSRRSTR  SESTSITKEE  HTGEGSLTKL  FFRWLVTLEG  DQDINDGKGY
  51  ISLPNVSNYI  FFLGGRFRTV  KGAKPLWLGV  LLAIVCPMVL  FSIFEAHKLW
 101  HTQNGYKVLV  IFFYYFWVIT  LASFIRTATS  DPGVLPRNIH  LSQLRNNYQI
 151  PQEYYNLITL  PTHSSISKDI  TIKYCPSCRI  WRPPRSSHCS  TCNVCVMVHD
 201  HHCIWVNNCI  GKRNYRFFLI  FLLGAILSSV  ILLTNCAIHI  ARESGGPRDC
 251  PVAILLLCYA  GLTLWYPAIL  FTYHIFMAGN  QQTTREFLKG  IGSKKNPVFH
 301  RVVKEENIYN  KGSFLKNMGH  LMLEPRGPSF  VSARKPHEAG  DWRFMDLSPA
 351  HSFEKIQKI*
```

FIG. 3A-B

(A)
ERF4 (YOL110W) Gene Sequence   Length: 714

```
  1  ATGTGCGATA GCCATCAAAA GGAAGAAGAT AACGCAAATA CGAGCGAAAG
 51  GGCGTTATTT TTTAATTACC ATGAGTTTTC GTATTCATTC TACGAAGACC
101  TCGGTTCCGA AGACGCTAAA CCCACAGAGC ACGACGAAGA CCACAAATTG
151  TGTATTACAC ATTTCCCGAA TGTGTATGCT GCTCGGGGCT CTGCCGAGTT
201  CCAGGTGACC CGGGTGGTAC GAGTGCCCCG GCGGTTCGAT GAGTCTCGCA
251  GCAGCCTTGA AACGCCACAA TTTAGTACAC AGCTTCCCGG TAGCGAGCCG
301  GCGGCAATCG TGGGCGACGA TGGCACTAGC TTTGTGCGGT GCGGGCGTTA
351  CGACATTGGG GATCACGTGT TTGGCTGCTC CTCCGTCTCG CCTCTGTCAG
401  AATATCTTAG TGCGGCAGAG CTCGCGGAGG TTGTGCACCG GGTAAACGGA
451  TTCTTGCTGC GTGAAGAAGG TGAGGTGTTC GGGTGGCGTA ACTTAAGTGG
501  CCTGTTGCTC GATATGCTTA CGGGCGGTCT GTGGAGCTGG GTTTTGGGGC
551  CCCTTCTTTC TAGACCTGTG TTTCAGGAGT CTCTCGCGTT AGAGCAGTAC
601  GTGGCGCAGC TAAACTCGCC GGGAGGTCTG CTTCACGAGC GCGGTGTGCG
651  CCTAGTATTG CCCCGACGGT CCGGGTGCCT ATCCCTAGAT TTCGTCGTGC
701  CCCGACCCAA ATAG
```

(B)
Erf4 (YOL110W) Protein Gene Sequence  Length: 238

```
  1  MCDSHQKEED NANTSERALF FNYHEFSYSF YEDLGSEDAK PTEHDEDHKL
 51  CITHFPNVYA ARGSAEFQVT RVVRVPRRFD ESRSSLETPQ FSTQLPGSEP
101  AAIVGDDGTS FVRCGRYDIG DHVFGCSSVS PLSEYLSAAE LAEVVHRVNG
151  FLLREEGEVF GWRNLSGLLL DMLTGGLWSW VLGPLLSRPV FQESLALEQY
201  VAQLNSPGGL LHERGVRLVL PRRSGCLSLD FVVPRPK*
```

FIG. 4A-B

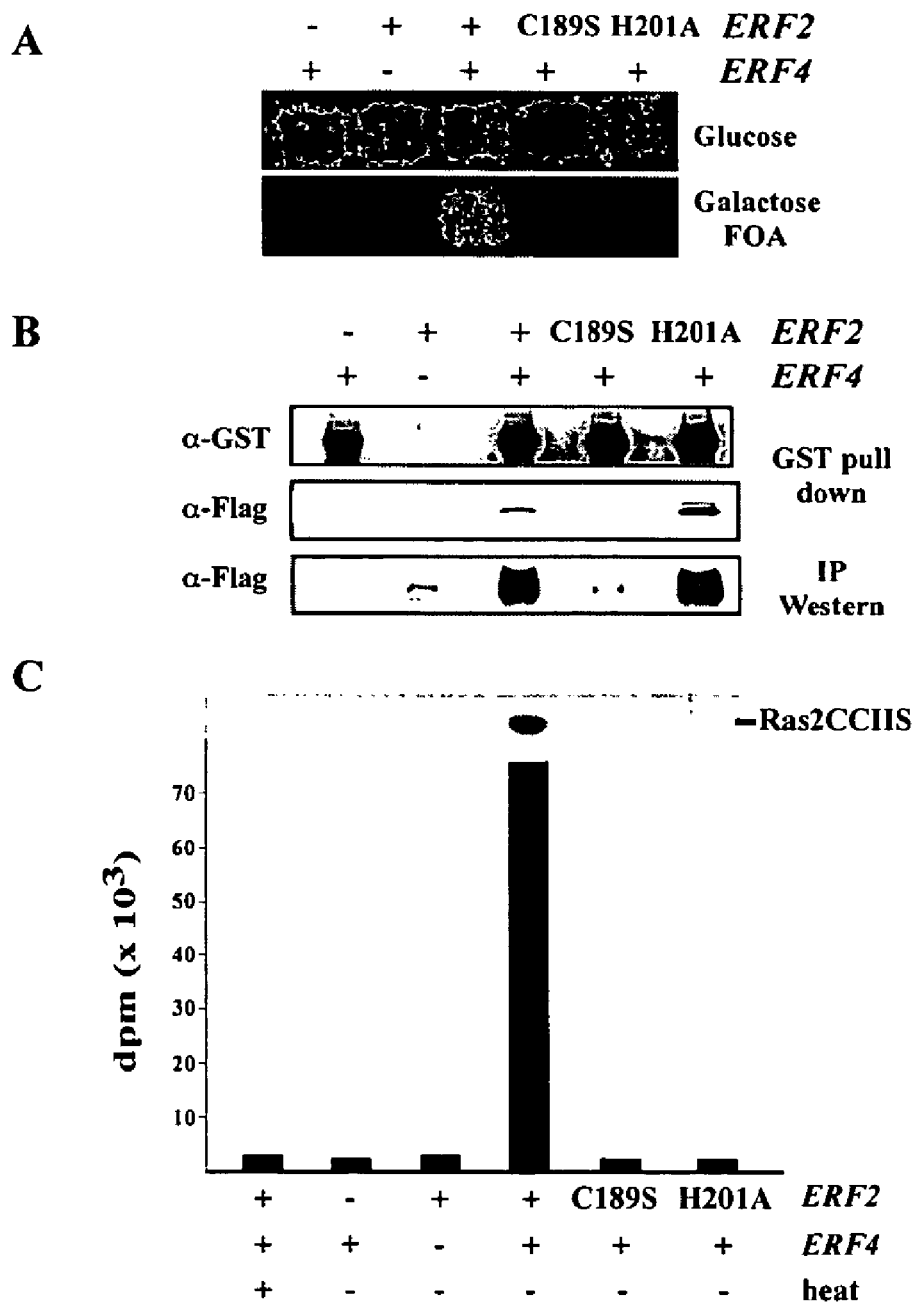
FIG. 6A-C

A
B
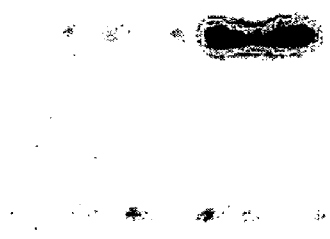
C
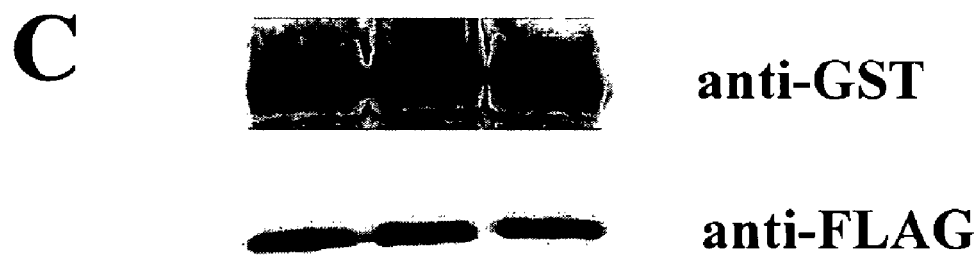
FIG. 7A-C

[³H]Palmitate
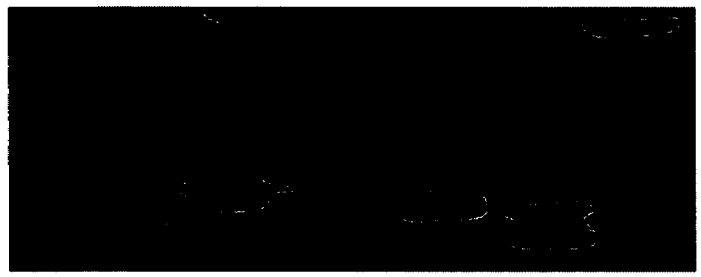
α-FLAG blot
FIG. 9

A

```
            1         10        20        30        40        51
            |---------+---------+---------+---------+---------+|
    Erf2sc  IKYCPSCRIWRPPRSSHCSTCNVCVMVHDHHCIMVNNCIGKRNYRFFLIFL
    DHHC18  LKYCFTCKMFRPPRTSHCSVCDNCVERFDHHCPWVGNCVGRRNYRFFYAFI
    DHHC9   LKYCYTCKIFRPPRASHCSICDNCVERFDHHCPWVGNCVGKRNYRYFYLFI
    DHHC14  LKYCFTCKIFRPPRASHCSLCDNCVERFDHHCPWVGNCVGKRNYRFFYMFI
    DHHC8   MKWCATCHFYRPPRCSHCSVCDNCVEDFDHHCPWVNNCIGRRNYRYFFLFL
    DHHC5   MKWCATCRFYRPPRCSHCSVCDNCVEEFDHHCPWVNNCIGRRNYRYFFLFL
    DHHC19  LQWCPKCCFHRPPRTYHCPWCNICVEDFDHHCKWVNNCIGHRNFRFFMLLV
    DHHC16  VSICKKCIYPKPARTHHCSICNRCVLKMDHHCPWLNNCVGHYNHRYFFSFC
    DHHC3   VYKCPKCCSIKPDRAHHCSVCKRCIRKMDHHCPWVNNCVGENNQKYFVLFT
    DHHC7   IYKCPKCCCIKPERAHHCSICKRCIRKMDHHCPWVNNCVGEKNQRFFVLFT
    DHHC2   IRYCDRCQLIKPDRCHHCSVCDKCILKMDHHCPWVNNCVGFSNYKFFLLFL
    DHHC15  VRFCDRCHLIKPDRCHHCSVCAMCVLKMDHHCPWVNNCIGFSNYKFFLQFL
    DHHC21  WELCNKCNLMRPKRSHHCSRCGHCVRRMDHHCPWINNCVGEDNHWLFLQLC
    DHHC6   LQYCKYCQAYKAPRSHHCRKCNRCVMKMDHHCPWINNCCGYQNHASFTLFL
    DHHC12  LRRCRYCLVLQPLRARHCRECRRCVRRYDHHCPWMENCVGERNHPLFVVYL
    DHHC17  SIFCSTCLIRKPVRSKHCGVCNRCIAKFDHHCPWVGNCVGAGNHRYFMGYL
    DHHC4   NVRCSTCDLRKPARSKHCSVCNMCVHRFDHHCVWVNNCIGAWNIRYFLIYV
    DHHC13  RTFCTSCLIRKPLRSLHCHVCNCCVARYDQHCLWTGRCIGFGNHHYYIFFL
    DHHC1   DLHCNLCNVDVSARSKHCSACNKCVCGFDHHCKWLNNCVGERNYRLFLHSV
    DHHC11  NQFCHLCKVTVNKKTKHCISCNKCVSGFDHHCKWINNCVGSRNYWFFFSTV
    DHHC23  EDWCAKCQLVRPARRAWHCRICGICVRRMDHHCVWYSVIITAGMAYIFLIQL
 Consensus  ...C..C....p.R..HCs.Cn.C!...DHHCpW.nnC!G..N...F...l
                 ↑    ↑↑              ↑↑                ↑
```

B

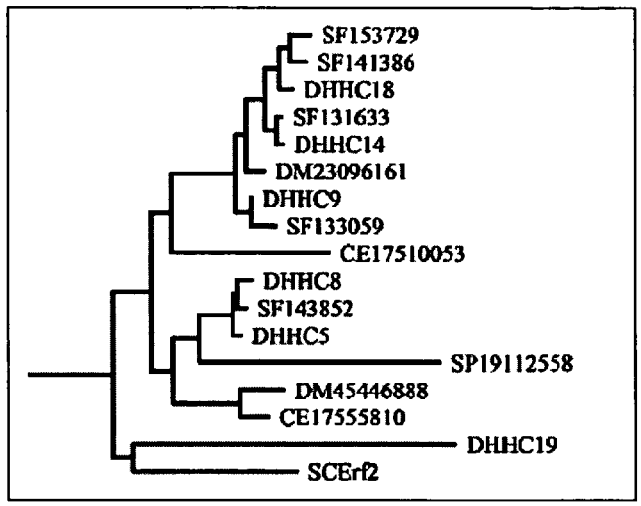

FIG. 10A-B

```
Erf2         ------MALVSRRSTRSESTSITKEEHTGEGSLTKLFFRWLVTLE--------------- 39
DHHC9(hE2-1) -------------MFLLSCNRKTHFGAGIPIMSVMVVRKKVT---------------- 29
DHHC14       --------MPPGGGGPMKDCEYSQISTHSSSPMESPHKKKKIA---------------- 35
DHHC18       MKDCEYQQISPG-AAPLPASPGARRPGPAASPTPGPGPAPPAAPAPPRWSSSGSGSGSGS 59
DHHC8        ------------------------------------------------------------
DHHC5        ------------------------------------------------------------
DHHC19       ------------------------------------------------------------

Erf2         GDQDINDGKGYISLPNVSNYIFFLGGRFRTVKGAKPLWLGVLLAIVCPMVLFSIFEAHKL  99
DHHC9(hE2-1) --------RKWEKLP--GRNTFCCDGRVMMARQKGIFYLTLFLILGTCTLFFAFECR---  76
DHHC14       ------ARRKWEVFP--GRNKFFCNGRIMMARQTGVFYLTLVLILVTSGLFFAFDCP---  84
DHHC18       GSLGRRPPRKWEVFP--GRNRFYCGGRLMLAGHGGVFALTLLLILTTTGLFFVFDCP--- 114
DHHC8        ------------MP--RSP-----GTRLKPAKYIPVATAAALLVGSSTLFFVFTCP---  37
DHHC5        ------------MP--AES-----GKRFKPSKYVPVSAAAIFLVGATTLFFAFTCP---  37
DHHC19       ----MTLLTDATPLV--KEPHPLPLVPRPWFLPSLFAAFNVVLLVFFSGLFFAFPCR---  51
                                            : :    ::*  :

Erf2         WHTQNGYKVLVIFFYYFWVITLASFIRTATSDPGVLPRNIHLSQLRNNYQIP-------Q 152
DHHC9(hE2-1) YLAVQLSPAIPVFAAMLFLFSMATLLRTSFSDPGVIPRALPDEAAFIEMEIEATNGAVPG 136
DHHC14       YLAVKITPAIPAVAGILFFFVMGTLLRTSFSDPGVLPRATPDEAADLERQIDIANGTSSG 144
DHHC18       YLARKLTLAIPIIAAILFFFVMSCLLQTSFTDPGILPRATVCEAAALEKQIDNTG---SS 171
DHHC8        WLTRAVSPAVPVYNGIIFLFVLANFSMATFMDPGVFPRADEDEDEKDD------------  85
DHHC5        GLSLYVSPAVPIYNAIMFLFVLANFSMATFMDPGIFPRAEEDEDEKDD------------  85
DHHC19       WLAQNGEWAFPVITGSLFVLTFFSLVSLNFSDPGILHQGSAEQG----------------  95
               :         ..   ::.:  :   :      ***::  :           .

Erf2         EYYNLITLPTHSSISKDITIKYCPSCRIWRPPRSSHCSTCNVCVMVHDHHCIWVNNCIGK 212
DHHC9(hE2-1) YQRPPPRIKNFQINNQIVKLKYCYTCKIFRPPRASHCSICDNCVERFDHHCPWVGNCVGK 196
DHHC14       GYRPPPRTKEVIINGQTVKLKYCFTCKIFRPPRASHCSLCDNCVERFDHHCPWVGNCVGK 204
DHHC18       TYRPPPRTREVLINGQMVKLKYCFTCKMFRPPRTSHCSVCDNCVERFDHHCPWVGNCVGR 231
DHHC8        --FRAPLYKNVDVRGIQVRMKWCATCHFYRPPRCSHCSVCDNCVEDFDHHCPWVNNCIGR 143
DHHC5        --FRAPLYKTVEIKGIQVRMKWCATCRFYRPPRCSHCSVCDNCVEEFDHHCPWVNNCIGR 143
DHHC19       ----PLTVHVVWVNHGAFRLQWCPKCCFHRPPRTYHCPWCNICVEDFDHHCKWVNNCIGH 151
                .  ::::*  .*  :  ****  **. *: ** .**** **.**:*:

Erf2         RNYRFFLIFLLGAILSSVILLTNCAIHIARESGGPR------DCPVAILLLCYAGLTLWY 266
DHHC9(hE2-1) RNYRYFYLFILSLSLLTIYVFAFNIVYVALKSLKIGFLETLKETPGTVLEVLICFFTLWS 256
DHHC14       RNYRFFYMFILSLSFLTVFIFAFVITHVILRSQQTGFLNALKDSPASVLEAVVCFFSVWS 264
DHHC18       RNYRFFYAFILSLSFLTAPIFACVVTHLTLRAQGSNFLSTLKETPASVLELVICFFSIWS 291
DHHC8        RNYRYFFLFLLSLSAHMVGVFAFGLVYVLNHAEGLGAAH----TTITMAVMCVAGLFFIP 199
DHHC5        RNYRYFFLFLLSLTAHIMGVFGFGLLYVLYHIEELSGVR----TAVTMAVMCVAGLFFIP 199
DHHC19       RNFRFFMLLVLSLCLYSGAMLVTCLIFLVRTTHLP-------FSTDKAIAIVVAVSAAGL 204
             **:*:*  ::*.          :.        .:              .

Erf2         PAILFTYHIFMAGNQQTTREFLKGIGSKKNPVFHRVVKEENIYNKGSFLKNMGHLMLEPR 326
DHHC9(hE2-1) VVGLTGFHTFLVALNQTTNEDIKGSWTGKNRVQN-------PYSHGNIVKNCCEVLCGPL 309
DHHC14       IVGLSGFHTYLISSNQTTNEDIKGSWSNKRGKEN-----YNPYSYGNIFTNCCVALCGPI 319
DHHC18       ILGLSGFHTYLVASNLTTNEDIKGSWSSKRGGEA----SVNPYSHKSIITNCCAVLCGPL 347
DHHC8        VIGLTGFHVVLVTRGRTTNEQVTGKFRGG---------VNPFTRG-CCGNVEHVLCSPL 248
DHHC5        VAGLTGFHVVLVARGRTTNEQVTGKFRGG---------VNPFTNG-CCNNVSRVLCSSP 248
DHHC19       LVPLSLLLLIQALSVSSADRTYKGKCRHLQG--------YNPFDQG-CASNWYLTICAPL 255
                *         :: .  .*            :         *    :   .
```

FIG. 11

```
Erf2          GPSFVSAR------------------------------------------------ 334
DHHC9(hE2-1)  PPSVLDRR-----------GILPLEESGSRP------------------------- 329
DHHC14        SPSLIDRR-----------GYIQPDTPQPAAPSNGITMYGATQSQSDMCDQDQCIQSTKF 368
DHHC18        PPSLIDRR-----------GFVQSDTVLPSP------------------------- 367
DHHC8         APRYVVEPPRLPLAVSLKPPFLRPELLDRAAPLKVKLSDNGLKAGLGRSKSKGSLDRLDE 308
DHHC5         APRYLGRP-KKEKTIVIRPPFLRPEVSD--GQITVKIMDNGIQGELRRTKSKGSLEITES 305
DHHC19        GPKAAASW------------------------------------------------ 263
                      *
Erf2          ---------------KPHEAGDWRFMDLSPAHSFEKIQKI------------------ 359
DHHC9(hE2-1)  ---------------PSTQETSSSLLPQSPAPTEHLNSNEMPEDSSTP---------- 362
DHHC14        VLQAAATPLLQSEPSLTSDELHLPGKPGLGTPCASLTLGPPTPPASMPNLAEATLADVMP 428
DHHC18        ---------------IRSDEPACRAKP-----DASMVGGHP----------------- 388
DHHC8         KPLDLGPPLPPKIEAGTFSSDLQTPRPGSAESALSVQRTSPPTPAMYKFRPAFP---TGP 365
DHHC5         QSADAEPPPPPKPDLSRYTGLRTHLGLATNEDSSLLAKDSPPTPTMYKYRPGYSSSSTSA 365
DHHC19        ---------------MRLASASCRAKPWAVCFPS----------------------- 282

Erf2          ------------------------------------------------------------
DHHC9(hE2-1)  --------EEMPPPEPPEPPQEAAEAEK----------------------------- 382
DHHC14        RKDEHMGHQFLTPDEAPSPPRLLAAGSPLAHSRTMHVLGLASQDSLHEDSVRGLVKLSSV 488
DHHC18        ------------------------------------------------------------
DHHC8         KVPFCGPGEQVPGPDSLTLGD---DSIRSLDFVSEPSLDLPDYGPGGLHAAYPPSPPLSA 422
DHHC5         AMPHSSSAKLSRG-DSLKEPTSIAESSRHPSYRSEPSLEPESFRSPTFGKSFHFDP-LSS 423
```

FIG. 11 CONT.

```
Erf4sc    MCDSHQKEEDNANTSERALFFNYHEFSYSFYEDLGSEDAKPTEHDEDHKLCITHFPNVYA
hE4-1     ---------------------------------------------------MRPQQ--
hE4-2     ------------------------------------MGLTTDFLPYEMLLGPVFTLLPVHNL
                                                                      *

Erf4sc    ARGSAEFQVTRVVRVPRRFDESRSSLETPQFSTQLPGSEPAAIVGDDGTSFVRCGRYDIG
hE4-1     ------APVSGKVFIQRDYSSG----TRCQFQTKFP------------------------
hE4-2     QELRRSASLATKVFIQRDYSDG----TICQFQTKFP------------------------
                ::  * : * :...      **.*::*

Erf4sc    DHVFGCSSVSPLSEYLSAAELAEVVHRVNGFLLREEGEVFGWRNLSGLLLDMLTGGLWSW
hE4-1     ---------AELENRIDRQQFEETVRTLNNLYA--EAEKLGGQSYLEGCLACLTAYTIFL
hE4-2     ---------PELDSRIERQLFEETVKTLNGFYA--EAEKIGGSSYLEGCLACATAYFIFL
                   . *.. :.    : *.*: :*.:    *.* :*  .     *    *.

Erf4sc    VLGPLLSRPVFQESLALEQYVAQLNSPGGLLHERGVRLVLPRRSGCLSLDFVVPRPK
hE4-1     CMETHYEKVLKKVSKYIQEQNEKIYAPQGLLLTDPIERGLRVIEITIYEDRGMSSGR
hE4-2     CMETHYEKVLKKISRYIQEQNEKIFAPRGLLLTDPVERGMRVVSFWAILC-------
            :  .  .: : : *   :::      :: :* ***     :.  :    .
```

FIG. 12

HUMAN PROTEIN ACYL TRANSFERASES AND METHODS OF USES THEREFOR

CROSS REFERENCE TO RELATED APPLICATIONS

This application is a divisional application of, and claims priority to, copending U.S. patent application Ser. No. 10/947,052, filed Sep. 22, 2004, which claims priority to U.S. Provisional Application Ser. No. 60/505,631, filed Sep. 24, 2003, each of which are hereby incorporated by reference in their entirety.

GOVERNMENT SPONSORED RESEARCH OR DEVELOPMENT

The government owns rights in the present invention pursuant to grant numbers R01CA50211 (RJD) and R01GM51466 (MEL) from the National Institutes of Health.

BACKGROUND OF THE INVENTION

1. Field of the Invention

The present invention relates generally to the fields of molecular biology and enzymology. More particularly, it concerns the isolation and characterization of human palmitoyltransferase complexes, and uses therefor.

2. Description of Related Art

Dozens of cellular and viral proteins are post-translationally modified with palmitate or other long-chain fatty acids through a reversible thioester linkage (Linder & Deschenes, 2003; Linder, 2001; Schlesinger et al., 1993). Examples include cell surface receptors, viral glycoproteins, and signal transducers including Ras, heterotrimeric G proteins, and non-receptor tyrosine kinases. Palmitoylation is almost exclusively a property of membrane proteins and can occur on intracellular membranes early in the secretory pathway, or later at the plasma membrane. Although this modification was first described over 30 years ago, the molecular mechanism of palmitate addition has yet to be elucidated and continues to be a matter of some controversy.

A variety of approaches have been used in an attempt to identify the enzyme(s) responsible for this function. A palmitoyltransferase activity assayed using mammalian H-Ras as a substrate was purified and identified as thiolase A, an enzyme required for fatty acid-oxidation (Liu et al., 1996a; Liu et al., 1996b). The localization of this enzyme in peroxisomes makes it an unlikely candidate for a physiological regulator of Ras palmitoylation. Palmitoyltransferase activities assayed using viral glycoproteins, the non-receptor tyrosine kinase p59fyn, or G-protein heterotrimer as substrates have been detergent-solubilized, but the instability of the activity has hampered purification and molecular identification (Dunphy et al., 1996, Dunphy et al., 2001; Berthiaume and Resh, 1995; Schmidt and Burns, 1989).

Accordingly, the identification of bona fide palmitoyl acyl transferases and the palmitoyl acyl transferase for Ras oncogene proteins remains an unachieved goal. In the absence of such an identification, the ability to screen for drugs that modulate the function of this family of enzymes remains limited.

SUMMARY OF THE INVENTION

The present invention relates to human palmitoyl acyl transferases. It also relates to the recombinant DNA moleculars encoding the palmitoyltransferase, a method for production of the recombinant protein, purification of the recombinant proteins, assay for PAT activity, and identification of modulator thereof.

Thus, in a first embodiment, there is provided a method of screening for modulators of human palmitoylation comprising (a) providing an isolated, active human DHHC palmitoyltransferase; (b) contacting said human palmitoyltransferase with a candidate substance and a source of palmitate; and (c) measuring palmitate transfer to said DHHC palmitoyltransferase (autopalmitoylation), wherein a change in palmitate transfer to the palmitoyltransferase, as compared to palmitate transfer to said DHHC palmitoyltransferase in the absence of said candidate substance, indicates that said candidate substance is a modulator of human palmitoylation.

In a second embodiment, there is provided a method of screening for modulators of human palmitoylation comprising (a) providing an isolated, active human DHHC palmitoyltransferase; (b) contacting said human palmitoyltransferase with a candidate substance, a source of palmitate and a substrate capable of accepting palmitate; and (c) measuring palmitate transfer to said substrate, wherein a change in palmitate transfer to said substrate, as compared to palmitate transfer to said substrate in the absence of said candidate substance, indicates that said candidate substance is a modulator of human palmitoylation.

The active human palmitoyltransferase are selected from the family of DHHC proteins and may be comprised of the Ras palmitoyltransferase hE2-1(DHHC9) and hE4-1, DHHC14 and hE4-1, DHHC18 and hE4-1, DHHC8 and hE4-1, DHHC5 and hE4-1, DHHC19 and hE4-1, hE2-1(DHHC9) and hE4-2, DHHC14 and hE4-2, DHHC18 and hE4-2, DHHC8 and hE4-2, DHHC5 and hE4-2, or DHHC19 and hE4-2.

The method may further comprise measuring palmitate transfer to the palmitoyltransferase (defined here as autopalmitoylation) or said substrate in the absence of said candidate substance. The autopalmitoylation reaction may comprise any of the 20 human DHHC proteins listed in FIG. 10A. The palmitate may comprise a label, such as a radioactive label, a fluorescent label, a chemiluminescent label or a dye. The substrate may be a Ras protein or other palmitoylation substrate or fragments thereof. Measuring may comprise scintillation counting, gel-based autoradiography, fluorimetry or microtiter plate assay.

In a second embodiment, there is provided an isolated and purified human Ras palmitoyltransferase complex. The human Ras palmitoyltransferase complex may be selected from the group consisting of (a) hE2-1(DHHC9), DHHC14, DHHC18, DHHC8, DHHC5 or DHHC19 alone or complexed with (b) hE4-1 or hE4-2. Furthermore, palmitoylation will be measured by monitoring the autopalmitoylation of DHHC proteins that occurs in the presence or absence of substrate.

In a third embodiment, there is provided an isolated and purified nucleic acid encoding a human Ras palmitoyltransferase subunit, such as hE4-1 (Gene ID 51125) or hE4-2 (Gene ID401647).

In a fourth embodiment, there is provided an expression cassette comprising a nucleic acid encoding a human Ras palmitoyltransferase subunit under the control of a heterologous promoter. The expression cassette may encode hE2-1 (DHHC9), hE4-1 or hE4-2; DHHC14, hE4-1 or hE4-2; DHHC18, hE4-1 or hE4-2; DHHC8, hE4-1 or hE4-2; DHHC5, hE4-1 or hE4-2; or DHHC19, hE4-1 or hE4-2. The expression cassette may encode a pair of subunits that together make a functional palmitoyl acyl transferase complex or a DHHC protein alone, and the expression cassette may comprise an internal ribosome entry site positioned between the two subunit coding regions. Alternatively, the expression construct may utilize two promoters, each driving the expression of one subunit. The expression cassette may be comprised within a host cell, such as bacteria, insect, yeast or mammalian cells. In particular, the host cell may be mammalian, such a mouse, hamster or human. The expression cassette may be comprised in a Bac, a Yac, or a viral vector.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herewith.

FIG. 3—Gene sequence of yeast ERF2 (SEQ ID NO: 1) and protein sequence of yeast Erf2 (SEQ ID NO: 2).

FIG. 4—Gene sequence of yeast ERF4 (SEQ ID NO: 3) and protein sequence of yeast Erf4 (SEQ ID NO: 4).

FIG. 6A-C—The Erf2p/Erf4p complex is a PAT for yeast Ras2 protein. ERF2 and ERF4 are required for the viability of palmitoylation-dependent yeast strains. (FIG. 6A). Plate assay demonstrating the requirement of functional ERF2 and ERF4 alleles for growth of RJY1277 expressing palmitoylation-dependent Ras2. Mutating residues, C189S or H201A, within the conserved DHHC-CRD of ERF2 leads to a loss in viability comparable to a complete deletion of ERF2. Viability was assessed on rich medium plates containing 2% glucose (YEP 2% Glu) (top) or rich plates containing 2% galactose and 0.1% 5-FOA (5.75 mM) YEP 2% Gal GOA) (bottom). A detailed description of this assay can be found in Bartels et al. (FIG. 6B) Immunoblot analysis of GST-Erf4p and FLAG-Erf2p from galactose induced cultures RJY543. Cells were solubilized in YPER reagent (Pierce) and the GST fusion proteins were partially purified on GSH agarose beads (Pierce). Samples were then immunoblotted with either anti (α)-GST to detect GST-Erf4p (top panel) or anti(α)-FLAG antibodies to detect FLAG-Erf2p (middle panel). Expression of FLAG-Erf2p was determined by affinity purification on anti-FLAG antibody linked to agarose beads followed by an anti-FLAG immunoblot (bottom panel). (FIG. 6C). The Ras PAT activity of partially purified extracts of ERF2 and ERF4 wild type and mutant strains was assayed as described in Example 1.

FIGS. 7A-C—Purification and PAT activity of Erf2p/Erf4p expressed in *E. coli*. (FIG. 7A) GLAD-Erf2p and GST-Erf4p were expressed together from an operon fusion in the pFLAG-MAC expression vector (Sigma). The gray and black boxes represent the GLAD epitope and GST, respectively. The white boxes represent the open reading frames of ERF2 and ERF4. The cells were lysed by high pressure (25,000 psi) homogenization and the GST-Erf4p/FLAG-Erf2p complex enriched using GSH agarose beads. FIG. 7B PAT assays were performed as described in Example 1. Reaction products were analyzed either directly (top panel) or prior to the PAT assay the GSH beads were heated (100° C., 15 min) (bottom panel). (FIG. 7C) Proteins partially purified by GSH agarose affinity chromatography were analyzed by immunoblotting with either anti-GST antibody (top panel) or anti-FLAG antibody (bottom panel).

FIG. 9—Autopalmitoylation of yeast DHHC domains. Membranes derived from yeast cells expressing GLAD-tagged Ynl326p, Yol003p, Ydr459p, Erf2p (co-expressed with Erf4p) or Akr1p from a Gal promoter were incubated with [$^3$H]palmitoyl-CoA. Radioactive palmitate was incorporated into the DHHC protein (upper panel). The identity of the band in each lane was confirmed by immunoblot with the FLAG antibody (lower panel). Psl10p was poorly expressed and thus, no autocylation was observed.

FIG. 10—Sequence alignment and phylogenetic relationship between *S. cerevisiae* Erf2p and human DHHC proteins. (FIG. 10A) Alignment of the DHHC-CRD region of yeast Erf2p (Erf2sc) with the human DHHC proteins (SEQ ID NO: 5). Gray indicates amino acids with high sequence conservation, gray arrow with moderate sequence conservation and black low conservation. (FIG. 10B) Phylogenetic relationship between Erf2sc and DHHC proteins from human (DHHC18, DHHC14, DHHC9, DHHC8, DHHC5, DHHC19), the fish Fugu rubipes (SF), *D. melanogaster* (DM), and *C. elegans* (CE).

FIG. 11—Sequence alignment of human homologs of Erf2p: Erf2 (SEQ ID NO:6, DHHC9 (SEQ ID NO:7), DHHC14 (SEQ ID NO:8), DHHC18 (SEQ ID NO:9), DHHC8 (SEQ ID NO:10), DHHC5 (SEQ ID NO:11), and DHHC19 (SEQ ID NO:12). The non-conserved C-terminus of DHHC5 and DHHC8 (350 amino acids) is not included in this alignment. The symbols under the alignment indicate sequence identity (*), highly conserved residue (::), and low sequence (:) conservation.

FIG. 12—Sequence alignment of human homologs of Erf4p: Erf4 (SEQ ID NO:13), hE4-1 (SEQ ID NO:14), and hE4-2 (SEQ ID NO:15). The symbols under the alignment indicate sequence identity (*), highly conserved residue (::), and low sequence (:) conservation.

DESCRIPTION OF ILLUSTRATIVE EMBODIMENTS

Prior Work Leading to Present Invention

Figure 1:
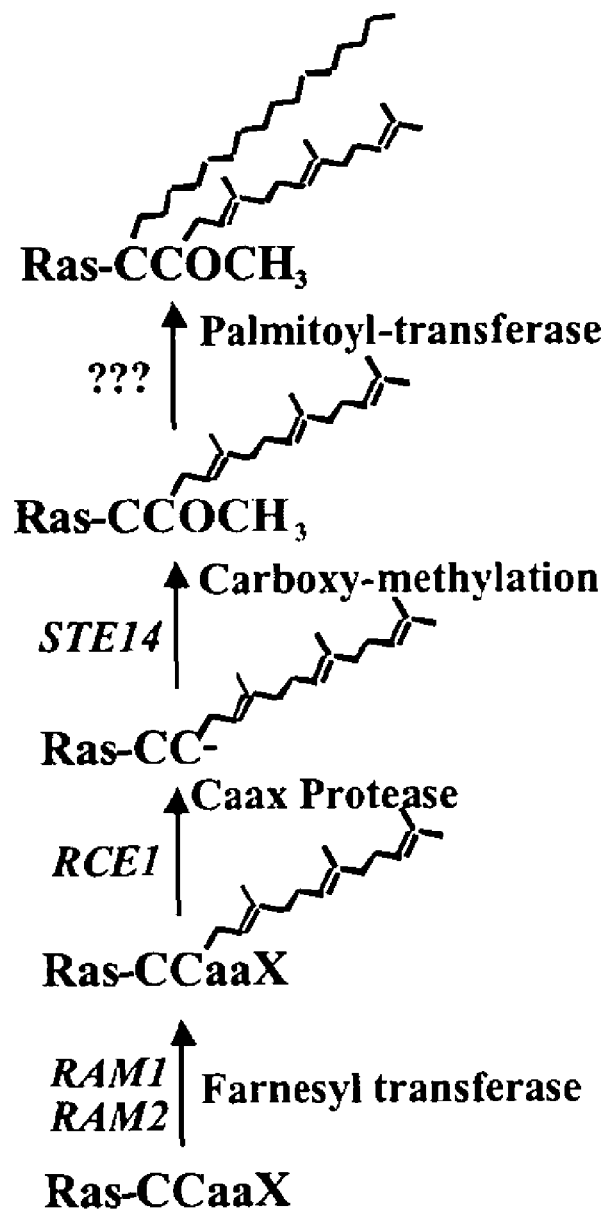
FIG. 1—Postranslational modification of Ras oncogene proteins. Proteins terminating in the conserved sequence motif, CaaX, are modified by a series of enzymatic steps that includes addition of a farnesyl moiety by the farnesyltransferase, proteolytic removal of the –aaX residues by the CaaX protease, carboxylmethylation by the methyltransferase, and palmitoylation of one or more cysteine residues generally in close proximity to the CaaX by a palmitoyltransferase.

Palmitoylation is required for efficient plasma membrane localization and transforming activity of oncogenic forms of Ras (Hancock et al., 1990). The present inventors determined that Ras oncogene products are highly conserved between mammalian and yeast systems, and that shared post-translational processing and subcellular localization steps are required for function: (a) transfer of a farnesyl moiety to the cysteine of the CCaaX motif; (b) protease removal of the –aaX terminus; (c) carboxylmethylation of the terminal cysteine; and (d) transfer of a palmitoyl moiety to the penultimate cysteine(s) (see FIG. 1 and reviews in Refs. Schafer and Rine (1992) and Clarke (1992)).

Figure 2:
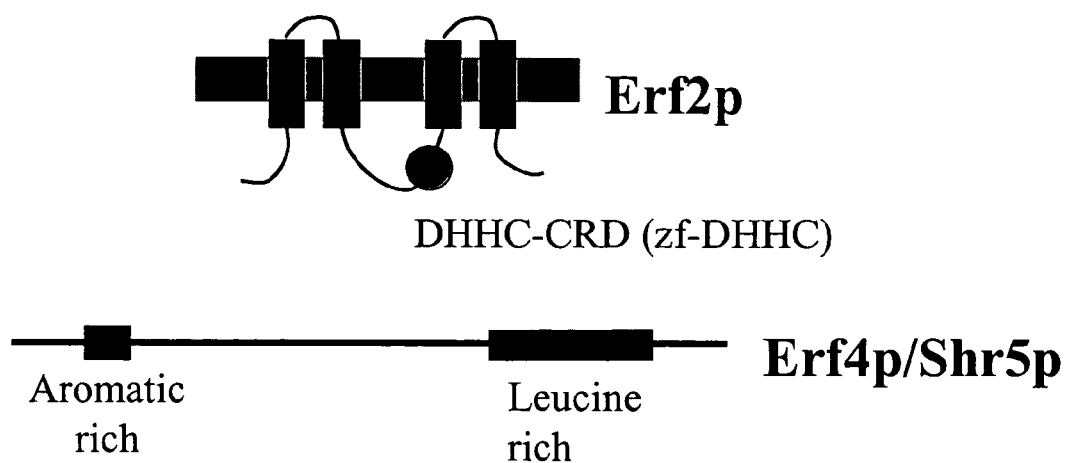
FIG. 2—Schematic diagram of yeast Erf2 and Erf4 proteins.

Previously, the palmitoylation-dependent alleles of yeast RAS2 were described, as was a genetic screen designed to identify mutations in such alleles (Mitchell et al., 1994; Bartels et al., 1999). Mutations in two genes, ERF2 and ERF4/SHR5, were identified that resulted in diminished palmitoylation of Ras2p and mislocalization of GFP-Ras2p (Bartels et al., 1999; Jung et al., 1995). Erf2p is a 41-kDa integral membrane protein localized at the ER, which contains a conserved Asp-His-His-Cys cysteine-rich domain (DHHC) between residues 164-228 (FIGS. 2 and 3). The DHHC domain, also referred to as the NEW1 or zf-DHHC domain (PF01529) is found in a large family of membrane proteins ranging from unicellular eukaryotes to humans (Bohm et al., 1997; Putilina et al., 1999). Genes encoding DHHC proteins in yeast include ERF2, AKR1, AKR2, PSL10/SWF1, YOL003c, YNL326c, and YDR459c. Erf4p is a 26-kDa peripheral ER membrane protein (FIGS. 2 and 4). When first isolated, it was not possible to know if the palmitoylation defect observed in erf2 and erf4 strains could affect palmitoylation directing or indirectly by perturbing Ras2p trafficking, and thereby prevent efficient interaction with a Ras palmitoyltransferase. The inventors were able to distinguish between these possibilities (Lobo et al., 2002).

Figure 5:
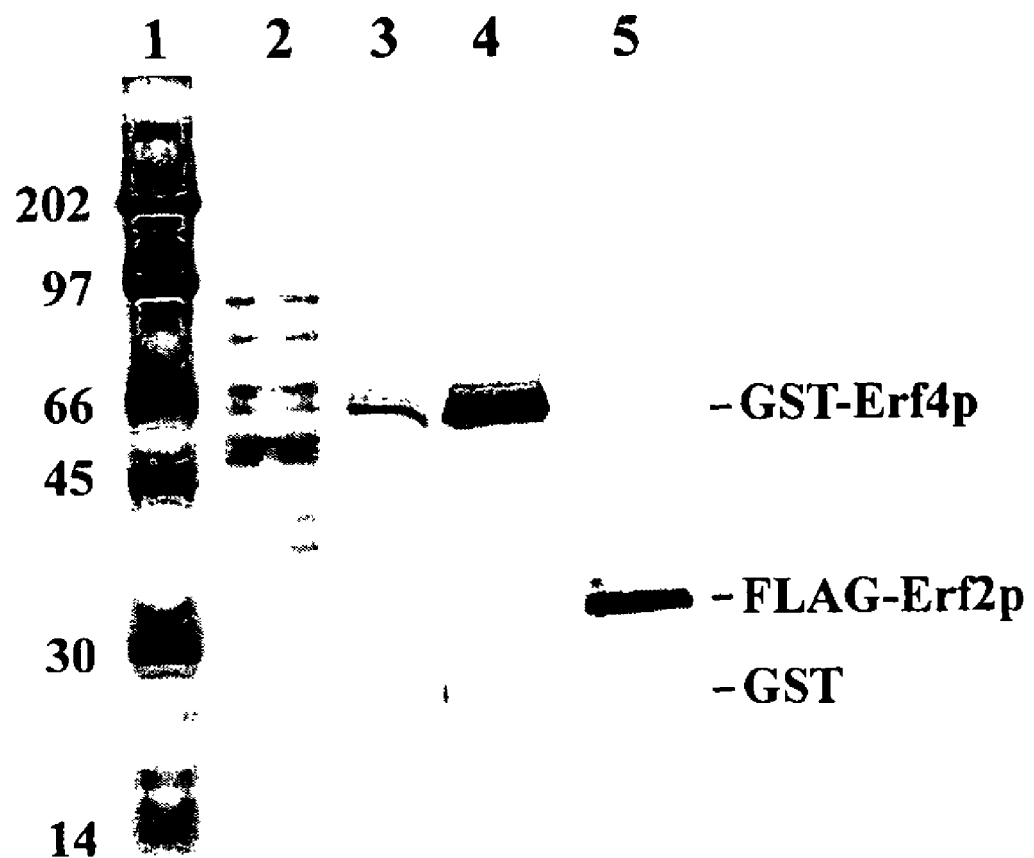
FIG. 5—Purification of Erf2p/Erf4p from yeast cell extracts. GST-Erf4p and FLAG-Erf2p were produced by galactose induction of yeast strain RJY543. Cells were lysed by homogenization and glutathione (GHS) affinity purification was performed as described in Example 1. A total cell extract (16.5 μg) (lane 2) or GSH affinity purified sample (1.4 μg) (lane 3) were resolved by SDS PAGE and the gel stained in Coomassie blue. Protein molecular weight standards were loaded in lane 1 and their size (kDa) indicated. The GSH bead enriched fraction was loaded on a second gel for immunoblotting with either anti-GST (lane 4) or anti-FLAG (lane 5) antibody.

The inventors next designed a strategy allowing the purification of the Erf2p/Erf4p complex from yeast (FIG. 5) and bacteria (FIG. 7A-C). It was determined that purified Erf2p and Erf4p constitute a protein acyl transferase responsible for the palmitoylation of yeast Ras2p (FIGS. 6A-C). The compatability of the previously described yeast system has permitted the testing of human homologs of these and other yeast enzymes. This has led to the present invention, which provides for identification of human palmitoyltransferase complexes, described in detail below. With the identification of active human palmitoyltransferase complexes, one can now screen for drugs that modify the function of these enzymes.

Figure 8:
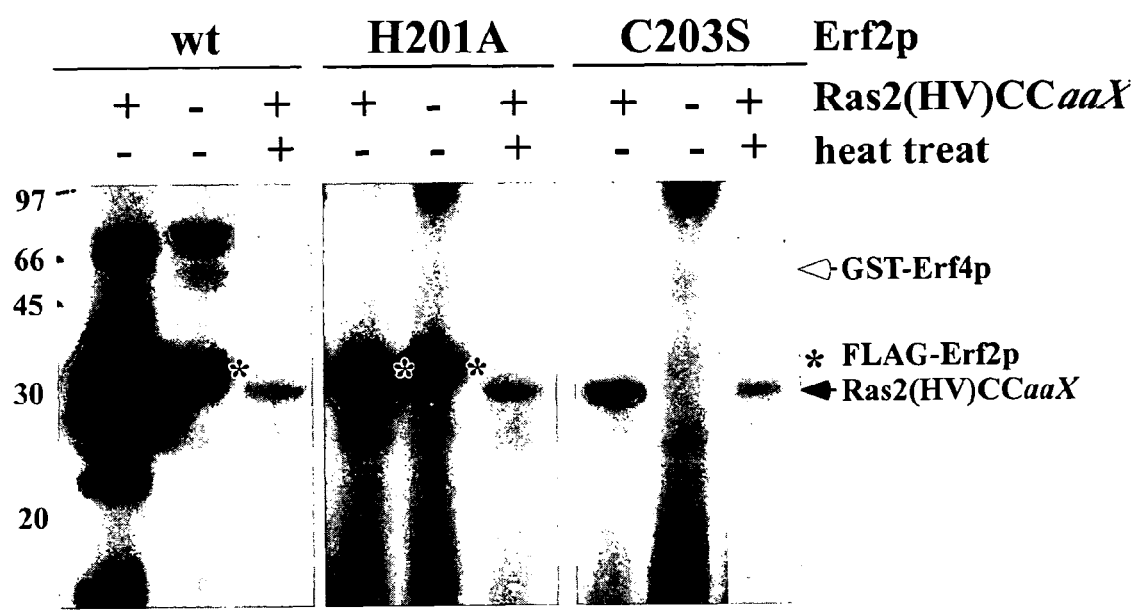
FIG. 8—Autopalmitoylation of Erf2p. [$^3$H]palmitoyl-CoA was added to wild type or Erf2p mutant (H201A or C203S) Erf2p/Erf4p complexes and Ras PAT assays were carried out as described in FIG. 1. The GST-Ras2(HV)CaaX was added to the Ras PAT reactions as indicated. A heat pre-treatment (100° C., 14 min) was performed to determine whether labeling was protein mediated. Samples were resolved by SDS-PAGE Bis-Tris gels, pH 6.4 (Nu-PAGE®), fixed and fluorography performed. The dried gel was exposed to film for 1 week. The asterisk indicates the migration position of FLAG-Erf2p. The arrow on the right indicates the migration position of GST-Ras2(HV)CCaaX.
Figure 15:
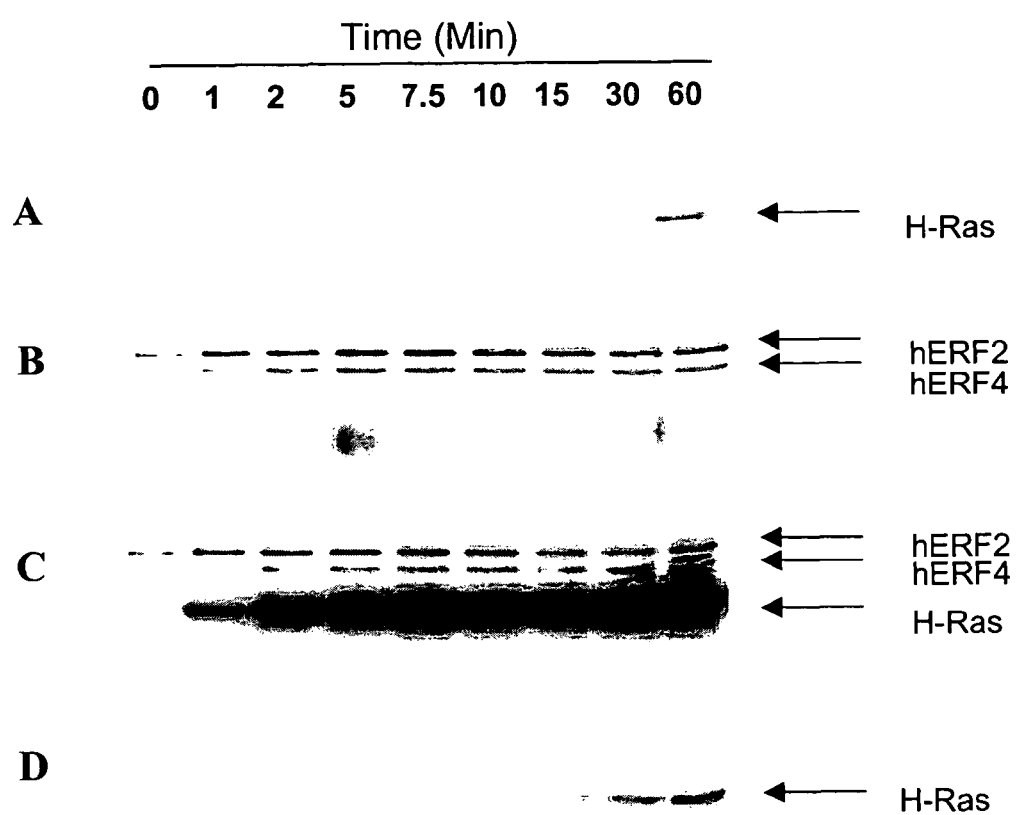
FIG. 15—Time course of hE2-1(DHHC9)/hE4-1 palmitoyltransferase activity. (A) Acylation of H-Ras in the absence of hErf2/hErf4 complex. (B) Acylation of hErf2/hErf4 complex in the absence of H-Ras. (C) A single tube PAT assay demonstrating acylation of H-Ras by the hErf2/hErf4 complex during a 60 min time course. (D) Acylation of H-Ras is reduced following heat inactivation of the hErf2/hErf4 complex.

The inventors have determined that the DHHC protein Erf2p becomes palmitoylated during the palmitoylation reaction. This autopalmitoylation reaction is dependent upon the cysteine residue within the DHHC-motif of Erf2p (FIG. 8). The inventors have shown that autopalmitoylation is a shared property of five DHHC proteins in yeast (FIG. 9) and human Erf2-1(DHHC9) (FIG. 15). This property can be used to screen for modulators of a DHHC palmitoyltransferase activity in the absence of a known substrate.

Present Invention: Identification and Characterization of Human Palmitoyl Acyl Transferases Palmitoylation is the covalent attachment of fatty acids to cysteine residues of membrane proteins. Palmitoylation of proteins occurs on cysteine residues located in a variety of sequence contexts (Linder and Deschenes, 2003) and the molecular signals for palmitoylation are not known. Palmitoylation of some proteins is reversible with cycles of acylation and deacylation, but the relevant acylating enzymes have not previously been identified.

The inventors' prior work has defined the functional unit of the palmitoyltransferase as a two-subunit enzyme comprised of one subunit related to yeast Erf2 and one subunit related to yeast Erf4. From this, the following human homologs corresponding to these subunits have now been identified:

TABLE 1

Erf2p (YLR246W) homologs (FIG. 11)

| NAME | GENE ID | GENE LOCUS |
| --- | --- | --- |
| hE2-1(DHHC9) | 51114 | Xq26 |
| DHHC14 | 79683 | 6q25 |
| DHHC18 | 84243 | 1p35 |
| DHHC8 | 29801 | 22q11.21 |
| DHHC5 | 25921 | 11q12 |
| DHHC19 | 131540 | 3q29 |

TABLE 2

Erf4p (YOL110W) homologs (FIG. 12)

| NAME | GENE ID | OTHER NAMES | GENE LOCUS |
| --- | --- | --- | --- |
| hE4-1 | 51125 | GOLGA7* | 8p11 |
| hE4-2 | 401647 | Gcp16-like | 10q24 |

*Golgi associated protein (Gcp16) (Ohta et al., 2003)

Figure 13:
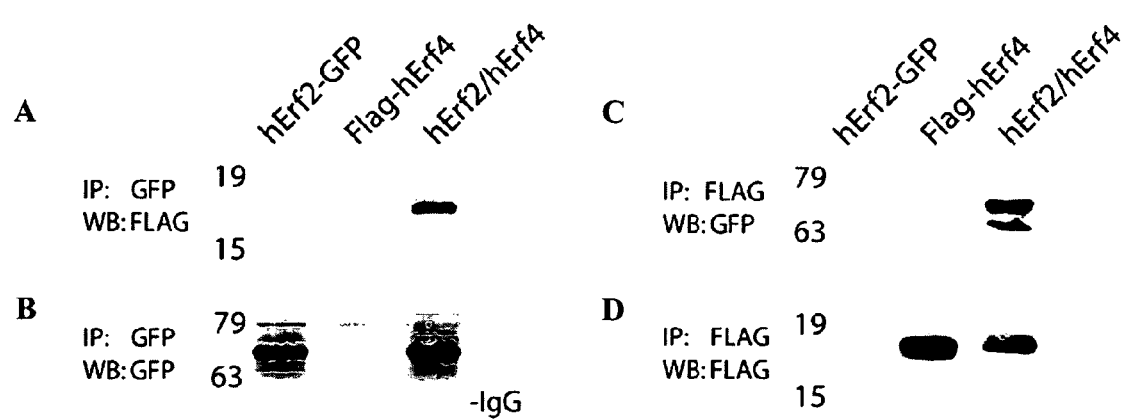
FIG. 13—Interaction between hE2-1(DHHC9) and hE4-1 expressed in HEK-293 cells. Whole cell extracts from HEK- 293 cells transiently transfected with hErf2-GFP (hE2-1/DHHC9), Flag-hErf4 (hE4-1), or hErf2 and hErf4 were subjected to immunoprecipitation with polyclonal antisera to GFP (A and B) or monoclonal ascites to the Flag epitope (C and D). Antigen complexes were detected with anti-Flag (A) or anti-GFP (C). To assess expression of hErf2-GFP and Flag-hErf4, nitrocellulose membranes were stripped and probed with anti-GFP (B) or anti-Flag (D) antibodies.

A key observation for establishing human Ras PAT activity is the pairing of hE2 and hE4 subunits (FIGS. 13 and 15). Neither subunit alone is capable of carrying out the palmitoylation reaction. The inventors predict that other pairings of hE2 and hE4 subunits will have activity toward human Ras proteins and potentially other substrates.

All DHHC proteins characterized to date by the inventors have the property of autoacylation, that is they undergo palmitoylation as a step in the palmitoyltransferase reaction. Examples of this fundamental property of DHHC proteins from yeast is shown in FIGS. 8 and 9. Based on this property it is thereby feasible to screen and characterize PAT inhibitors for any DHHC PAT without knowing the identity of the substrate or substrates.

Peptides and Polypeptides

As discussed above, a variety of different protein molecules have been implicated as human palmitoyl acyl transferase subunits. These proteins may be obtained from natural sources or synthesized. Thus, in certain embodiments, the present invention concerns proteinaceous compositions comprising these palmitoyl acyl transferases and subunits thereof. As used herein, "proteinaceous molecule," "proteinaceous composition," "proteinaceous compound," and/or "proteinaceous material" generally refer to proteins and peptides of varying lengths. All the "proteinaceous" terms described above may be used interchangeably herein.

In certain embodiments, one may wish to employ short molecules derived from the proteins on the preceding list. Peptides are contemplated of about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, to about 100 residues.

Proteinaceous compositions may be made by any technique known to those of skill in the art, including recombinant expression, isolation from natural sources, or chemical synthesis. In certain embodiments, the proteinaceous compound may be purified. Generally, "purified" refers to a specific protein, polypeptide, or peptide composition that has been subjected to fractionation to remove various other proteins, polypeptides, or peptides, and which composition substantially retains its activity.

It will be desirable to purify various proteins in accordance with the present invention. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography, polyacrylamide gel electrophoresis, and isoelectric focusing. A particularly efficient method of purifying peptides is fast protein liquid chromatography or even HPLC.

The term "purified protein or peptide" as used herein is intended to refer to a composition, isolated from other components, wherein the protein or peptide is purified to any degree relative to its naturally-obtainable state. A purified protein or peptide therefore also refers to a protein or peptide, free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation, chromatography steps such as ion exchange, gel filtration, reverse phase, hydroxylapatite and affinity chromatography, isoelectric focusing, gel electrophoresis, and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a great "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE 9Capaldi et al., 1977). It will therefore be appreciated that under differing electrophoresis conditions, the apparent molecular weights of purified or partially purified expression products may vary.

High performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

Nucleic Acids and Expression Constructs

Certain embodiments of the present invention concern a nucleic acid encoding a human palmitoyl acyl transferase subunit. The nucleic acid may be natural or synthetic. In other aspects, the nucleic acid may comprise a fragment of such nucleic acids, an antisense molecule, a ribozyme or an interfering RNA. In particular aspects, the nucleic acid is a cDNA. The term "nucleic acid" is well known in the art, and generally refers to a molecule (i.e., a strand) of DNA, RNA or a derivative or analog thereof. The term "nucleic acid" encompasses the terms "oligonucleotide" and "polynucleotide," each as a subgenus of the term "nucleic acid." The term "oligonucleotide" refers to a molecule of between about 3 to about 50 nucleobases in length. The term "polynucleotide" refers to at least one molecule of greater than about 50 nucleotides in length.

A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described in Froehler et al. (1986) and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146 and 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,194, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

In certain aspects, the present invention concerns a nucleic acid that is an isolated nucleic acid. As used herein, the term "isolated nucleic acid" refers to a nucleic acid molecule (e.g., an RNA or DNA molecule) that has been partially or substantially isolated free of total genomic and in vitro reaction products. In certain embodiments, "isolated nucleic acid" also refers to a nucleic acid that has been isolated free of the bulk of cellular components or in vitro reaction components.

A nucleic acid may be purified on polyacrylamide gels, cesium chloride centrifugation gradients, or by any other means known to one of ordinary skill in the art (see for example, Sambrook et al., 2001, incorporated herein by reference).

As used herein, "wild-type" refers to the naturally-occurring sequence of a nucleic acid at a genetic locus in the genome of an organism, or a sequence transcribed or translated from such a nucleic acid. Thus, the term "wild-type" also may refer to an amino acid sequence encoded by a nucleic acid. As a genetic locus may have more than one sequence or alleles in a population of individuals, the term "wild-type" encompasses all such naturally-occurring allele(s). As used herein, the term "polymorphic" means that variation exists (i.e., two or more alleles exist) at a genetic locus in the individuals of a population. As used herein "mutant" refers to a change in the sequence of a nucleic acid or its encoded protein, polypeptide or peptide that is the result of the hand of man.

In one embodiment, the present invention encompasses a nucleic acid that is complementary to a nucleic acid encoding a palmitoyl acyl transferase subunit. A nucleic acid is "complement(s)" or is "complementary" to another nucleic acid when it is capable of base-pairing with another nucleic acid according to the standard Watson-Crick, Hoogsteen or reverse Hoogsteen binding complementary rules. As used herein, the term "complementary" or "complement(s)" also refers to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. In certain embodiments, a "complementary" nucleic acid comprises a sequence in which about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range derivable therein, of the nucleotide sequence is capable of base-pairing with a single- or double-stranded nucleic acid molecule during hybridization. In certain embodiments, the term "complementary" refers to a nucleic acid that may hybridize to another nucleic acid strand or duplex in stringent conditions, as would be understood by one of ordinary skill in the art. In certain embodiments, a "partly complementary" nucleic acid comprises a sequence that may hybridize in low stringency conditions to a single or double stranded nucleic acid, or contains a sequence in which less than about 70% of the nucleobase sequence is capable of base-pairing with a single or double stranded nucleic acid molecule during hybridization.

As used herein, "hybridization," "hybridizes," or "capable of hybridizing" are understood to mean the forming of a double or triple stranded molecule or a molecule with partial double or triple stranded nature. The term "anneal" as used herein is synonymous with "hybridize." The terms "hybridization," "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to an nucleic acid under stringent conditions may be achieved by hybridization at low temperature and/or high ionic strength. Such conditions are termed "low stringency" or "low stringency conditions," and non-limiting examples of low stringency include hybridization performed at about 0.15 M to about 0.9 M NaCl at a temperature range of 20° C. to about 50° C. Of course, it is within the skill of one in the art to further modify the low or high stringency conditions to suite a particular application.

The present invention also concerns the isolation or creation of a recombinant construct or a recombinant host cell through the application of recombinant nucleic acid technology known to those of skill in the art or as described herein. A recombinant construct or host cell may comprise a nucleic acid encoding one or more genes for palmitoyltransferase subunits. A "gene" refers to a nucleic acid that is transcribed. In certain aspects, the gene includes regulatory sequences involved in transcription, or message production or composition. In particular embodiments, the gene comprises transcribed sequences that encode for a protein, polypeptide or peptide.

The nucleic acid(s) of the present invention, regardless of the length of the sequence itself, maybe combined with other nucleic acid sequences, including but not limited to, promoters, enhancers, polyadenylation signals, restriction enzyme sites, multiple cloning sites, coding segments, and the like, to create one or more nucleic acid construct(s). As used herein, a "nucleic acid construct" is a nucleic acid engineered or altered by the hand of man, and generally comprises one or more nucleic acid sequences organized by the hand of man.

Functionally equivalent codons are codons that encode the same amino acid, such as the six codons for arginine and serine, and also refers to codons that encode biologically equivalent amino acids. For optimization of expression in human cells, the codons are shown in Table 3 in preference of use from left to right. Thus, the most preferred codon for alanine is "GCC," and the least is "GCG." Codon usage for various organisms and organelles can be found at the website www.kazusa.or.jp/codon/, incorporated herein by reference, allowing one of skill in the art to optimize codon usage for expression in various organisms for other animals, as well as other organisms such as a yeast, based on the preferred codon usage as would be known to those of ordinary skill in the art.

TABLE 3

Preferred Human DNA Codons

| Amino Acids | | | Codons | | | | | |
|---|---|---|---|---|---|---|---|---|
| Alanine | Ala | A | GCC | GCT | GCA | GCG | | |
| Cysteine | Cys | C | TGC | TGT | | | | |
| Aspartic Acid | Asp | D | GAC | GAT | | | | |
| Glutamic acid | Glu | E | GAG | GAA | | | | |
| Phenylalanine | Phe | F | TTC | TTT | | | | |
| Glycine | Gly | G | GGC | GGG | GGA | GGT | | |
| Histidine | His | H | CAC | CAT | | | | |
| Isoleucine | Ile | I | ATC | ATT | ATA | | | |
| Lysine | Lys | K | AAG | AAA | | | | |
| Leucine | Leu | L | CTG | CTC | TTH | CTT | CTA | TTA |
| Methionine | Met | M | ATG | | | | | |
| Asparagine | Asn | N | AAC | AAT | | | | |
| Proline | Pro | P | CCC | CCT | CCA | CCG | | |
| Glutamine | Gln | Q | CAG | CAA | | | | |
| Arginine | Arg | R | CGC | AGG | CGG | AGA | CGA | CGT |
| Serine | Ser | S | AGC | TCC | TCT | AGT | TCA | TCG |
| Threonine | Thr | T | ACC | ACA | ACT | ACG | | |
| Valine | Val | V | GTG | GTC | GTT | GTA | | |
| Tryptophan | Trp | W | TGG | | | | | |
| Tyrosine | Tyr | Y | TAC | TAT | | | | |

It will also be understood that amino acid sequences or nucleic acid sequences may include additional residues, such as additional N- or C-terminal amino acids or 5' or 3' sequences, or various combinations thereof, and yet still be essentially as set forth in one of the sequences disclosed herein, so long as the sequence meets the criteria set forth above, including the maintenance of biological protein, polypeptide or peptide activity where expression of a proteinaceous composition is concerned. The addition of terminal sequences particularly applies to nucleic acid sequences that may, for example, include various non-coding sequences flanking either of the 5' and/or 3' portions of the coding region or may include various internal sequences, i.e., introns, which are known to occur within genes.

1. Vectors

As discussed above, the term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and yeast artificial chromosomes (e.g., YACs). One of skill in the art would be well equipped to construct a vector through standard recombinant techniques (see, for example, Maniatis et al., 1990, incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

a. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription of a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers or other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such an mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example, Sambrook et al., 2001, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, www.epd.isb-sib.ch/) could be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Table 4 lists non-limiting examples of elements/promoters that may be employed, in the context of the present invention, to regulate the express of a RNA. Table 5 provides non-limiting examples of inducible elements, which are regions of a nucleic acid sequence that can be activated in response to a specific stimulus.

TABLE 4

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987, Weinberger et al., 1984; Kiledjian et al., 1988; Porton et al., 1990 |
| Immunoglobulin Light Chain | Queen et al., 1983; Picard et al., 1984 |
| T-Cell Receptor | Luria et al., 1987; Winoto et al., 1989; Redondo et al., 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-Dra | Sherman et al., 1989 |
| β-Actin | Kawamoto et al., 1988; Ng et al., 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| γ-Globin | Bodine et al., 1987; Perex-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| α$_1$-Antitrypsin | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Drived Growth Factor (PDGF) | Pech et al., 1989 |
| Duchenne Muscular Dystrophy | Klamut et al., 1990 |

TABLE 4-continued

Promoter and/or Enhancer

| Promoter/Enhancer | References |
|---|---|
| SV40 | Banerji et al., 1981; Moreau et al. 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987, Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 5

Inducible Elements

| Element | Inducer | References |
|---|---|---|
| MT II | Phorbol Ester (TGA) Heavy Metals | Palmiter et al., 1982; Haslinger et al., 1985; Searle et al., 1985; Stuart et al., 1985; Imagawa et al., 1987; Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | Poly(rI) × Poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2_b | Interferon | Blanar et al., 1989 |
| HSP70 | EIA, SV40 Large T Antigen | Taylor et al., 1989, 1990a, 1990b |
| Proliferin | Phorbol Ester-TPA | Mordacq et al., 1989 |
| Tumor Necrosis Factor α | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Non-limiting examples of such regions include the human LIMK2 gene (Nomoto et al., 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki et al., 1998), DIA dopamine receptor gene (Lee et al., 1997), insulin-like growth factor II (Wu et al., 1997), and human platelet endothelial cell adhesion molecule-1 (Almendro et al., 1996).

b. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well as an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

c. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999; Levenson et al., 1998; and Cocea, 1997, incorporated herein by reference). "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference).

e. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with the PolyA tail appear to be more stable and are translated more efficiently. Thus, in other embodiments involving eukaryotes, it is preferred that the terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

f. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

g. Origins of Replication

In order to propagate a vector in a host cell, it may contain one or more origins of replication sites (often termed "ori"), which is a specific nucleic acid sequence at which replication is initiated. Alternatively, an autonomously replicating sequence (ARS) can be employed if the host cell is yeast.

h. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

i. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivative of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbialorganism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, E. coli LE392.

Further useful plasmid vectors include pIN vectors (Inouye et al., 1985); and pGEX vectors for use in generating glutathione S-transferase (GST) soluble fusion proteins for later purification and separation or cleavage. Other suitable fusion proteins are those with β-galactosidase, ubiquitin, and the like.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

2. Vector Delivery and Cell Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et al., 1989; Nabel et al., 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1974; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982); Fraley et al., 1979; Nicolau et al., 1987; Wong et al., 1980; Kaneda et al., 1989; Kato et al., 1991) and receptor-mediated transfection (Wu and Wu 1987; Wu and Wu, 1988); by microprojectile bombardment (PCT Publication Nos. WO 94/09699 and WO 95/06128; U.S. Pat. Nos. 5,610,042, 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s), or organism(s) may be stably or transiently transformed.

a. Injection

In certain embodiments, a nucleic acid may be delivered to an organelle, a cell, a tissue or an organism via one or more injections (i.e., a needle injection), such as, for example, subcutaneously, intradermally, intramuscularly, intervenously, intraperitoneally, etc. Methods of injection of vaccines are well known to those of ordinary skill in the art (e.g., injection of a composition comprising a saline solution). Further embodiments of the present invention include the introduction of a nucleic acid by direct microinjection. Direct microinjection has been used to introduce nucleic acid constructs into Xenopus oocytes (Harland and Weintraub, 1985).

b. Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rate heptocytes have been transfected with the chloramphenicol acetyltransferase gene (Tur-Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon-derived protoplasts is described by Dhir and Widholm in PCT Publication WO 92/17598, incorporated herein by reference. Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

c. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

d. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

e. Sonication Loading

Additional embodiments of the present invention include the introduction of a nucleic acid by direct sonic loading. LTK-fibroblasts have been transfected with the thymidine kinase gene by sonication loading (Fechheimer et al., 1987).

f. Liposome-Mediated Transfection

In a further embodiment of the invention, a nucleic acid may be entrapped in a lipid complex such as, for example, a liposome. Liposomes are vesicular structures characterized by a phospholipid bilayer member and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

g. Receptor Mediated Transfection

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

h. Microprojectile Bombardment

Microprojectile bombardment techniques can be used to introduce a nucleic acid into at least one, organelle, cell, tissue or organism (U.S. Pat. No. 5,550,318; U.S. Pat. No. 5,538,880; U.S. Pat. No. 5,610,042; and WO 94/09699, each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

Microprojectile bombardment may be used to transform various cell(s), tissue(s) or organism(s), such as for example any plant species. Examples of species which have been transformed by microprojectile bombardment include monocot species such as maize (WO 95/06128), barley (Ritala et al., 1994; Hensgens et al., 1993), wheat (U.S. Pat. No. 5,563,055, incorporated herein by reference), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, incorporated herein by reference), sunflower (Knittel et al., 1994), peanut (Singsit et al., 1997), cotton (McCabe and Martinell, 1993), tomato (Van Eck et al., 1995), and legumes in general (U.S. Pat. No. 5,563,055, incorporated herein by reference).

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the microprojectile stopping plate.

An illustrative embodiment of a method for delivering DNA into a cell (e.g., a plant cell) by acceleration is the Biolistics Particle Delivery System, which can be used to propel particles coated with DNA or cells through a screen, such as a stainless steel or Nytex screen, onto a filter surface covered with cells, such as for example, a monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

3. Host Cells

As used herein, the terms "cell," "cell line," and "cell culture" may be used interchangeably. All of these terms also include their progeny, which includes any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfect" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid.

In certain embodiments, it is contemplated that RNAs or proteinaceous sequences may be co-expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for RNAs, which could then be expressed in host cells transfected with the single vector.

In certain embodiments, the host cell or tissue may be comprised in at least one organism. In certain embodiments, the organism may be, but is not limited to, a prokaryote (e.g., a eubacteria, an archaea) or an eukaryote, as would be understood by one of ordinary skill in the art (see, for example, webpage phylogeny.Arizona.edu/tree/phylogeny.html).

Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Cell types available for vector replication and/or expression include, but are not limited to, bacteria, such as *E. coli* (e.g., *E. coli* strain RR1, *E. coli* LE392, *E. coli* B, *E. coli* X 1776 (ATCC No. 31537) as well as *E. coli* W3110 (F-, lambda-, prototropic, ATCC No. 273325), DH5α, JM109, and KC8, bacilli such as *Bacillus subtilis*; and other enterobacteriaceae such as *Salmonella typhimurium, Serratia marcescens*, various *Pseudomonas* specie, as well as a number of commercially available bacterial hosts such as SURE® Competent Cells and SOLOPACK™ Gold Cells (STRATAGENE®, La Jolla). In certain embodiments, bacterial cells such as *E. coli* LE392 are particularly contemplated as host cells for phage viruses.

Examples of eukaryotic host cells for replication and/or expression of a vector include, but are not limited to, HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

4. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MAXBAC® 2.0 from INVITROGEN® and BACPACK™ BACULOVIRUS EXPRESSION SYSTEM from CLONTECH®.

Other examples of expression systems include STRATAGENE®'S COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

It is contemplated that the proteins, polypeptides or peptides produced by the methods of the invention may be "overexpressed," i.e., expressed in increased levels relative to its natural expression in cells. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein, polypeptide or peptide in comparison to the level in natural cells is indicative of overexpression, as is a relative abundance of the specific protein, polypeptides or peptides in relation to the other proteins produced by the host cell and, e.g., visible on a gel.

In some embodiments, the expressed proteinaceous sequence forms an inclusion body in the host cell, the host cells are lysed, for example, by disruption in a cell homogenizer, washed and/or centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed. Inclusion bodies may be solubilized in solutions containing high concentrations of urea (e.g., 8M) or chaotropic agents such as guanidine hydrochloride in the presence of reducing agents, such as β-mercaptoethanol or DTT (dithiothreitol), and refolded into a more desirable conformation, as would be known to one of ordinary skill in the art.

V. Yeast

Yeast are unicellular fungi whose mechanisms of cell-cycle control are remarkably similar to that of humans. The precise classification is a field that uses the characteristics of the cell, ascospore and colony. Physiological characteristics are also used to identify species. One of the more well known characteristics is the ability to ferment sugars for the production of ethanol. Budding yeasts are true fungi of the phylum Ascomycetes, class Hemiascomycetes. The true yeasts are separated into one main order Saccharomycetales. Yeasts are characterized by a wide dispersion of natural habitats, and are common on plant leaves and flowers, soil and salt water. Yeasts are also found on the skin surfaces and in the intestinal tracts of warm-blooded animals, where they may live symbiotically or as parasites.

Yeasts multiply as single cells that divide by budding (e.g., *Saccharomyces*) or direct division (fission, e.g., *Schizosaccharomyces*), or they may grow as simple irregular filaments (mycelium). In sexual reproduction most yeasts form asci, which contain up to either haploid ascospores. These ascospores may fuse with adjoining nuclei and multiply through vegetative division or, as with certain yeasts, fuse with other ascospores.

The awesome power of yeast genetics is partially due to the ability to quickly map a phenotype producing gene to a region of the *S. cerevisiae* genome. For the past two decades, *S. cerevisiae* has been the model system for much of molecular genetic research because the basis cellular mechanics or replication, recombination, cell division and metabolism are generally conserved between yeast and larger eukaryotes, including mammals. It is also a straightforward matter to engineer yeast cells to express a variety of heterologous constructs, and to do so in a controlled fashion.

1. Yeast Cultures

Some yeast varieties reproduce almost as rapidly as bacteria and have a genome size less than 1% that of a mammal. They are amendable to repaid molecular genetic manipulation, whereby genes can be deleted, replaced, or altered. They also have the unusual ability to proliferate in a haploid state, in which only a single copy of each gene is present in the cell. This makes it easy to isolate and study mutations that inactivate a gene as one avoids the complication of having a second copy of the gene in the cell.

The process of culturing yeast strains involves isolation of a single yeast cell, maintenance of yeast cultures, and the propagation of the yeast until an amount sufficient for pitching is obtained. Pure yeast cultures are obtained from a number of sources such as commercial distributors or culture collections. Various procedures are used to collect pure cultures, including culturing from a single colony, a single cell, or a mixture of isolated cells and colonies.

The objective of propagation is to produce large quantities of yeast with known characteristics in as short a time as possible. One method is a batch system of propagation, starting with a few milliliters of stock culture and scaling up until a desired quantity of yeast has been realized. Scale-up introduces actively growing cells to a fresh supply of nutrients in order to produce a crop of yeast in the optimum physiological state.

2. Yeast Promoters

Useful yeast promoters for the conditional expression of toxic peptidases include those directing expression of metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in EP 73,675A, herein incorporated by reference in its entirety. Other examples of strong yeast promoters are the alcohol dehydrogenase, lactase and triosephosphate isomerase promoters.

For expression of yeast genes in yeast, to determine the effects of mutations, it is generally best to use the gene's promoter in a CEN plasmid so expression is similar to the wild-type gene. However, there are a variety of promoters to choose from for various purposes. One such promoter is the Gal 1,10 promoter, which is inducible by galactose. It is frequently valuable to be able to turn expression of the gene on and off so one can follow the time dependent effects of expression.

The Gal 1 gene and Gal 10 gene are adjacent and transcribed in opposite directions from the same promoter region. The regulatory region containing the UAS sequences can be cut out on a Ddel Sau3A fragment and placed upstream of any other gene to confer galactose inducible expression and glucose repression. The PGK, GPD and ADH1 promoters are high expression constitutive promoters (PGK=phosphoglycerate kinase, GPD=glyceraldehyde 3 phosphate dehydrogenase, ADH1=alcohol dehydrogenase). The ADH2 promoter is glucose repressible and it is strongly transcribed on non-fermentable carbon sources (similar to GAL 1 or 10) except not inducible by galactose. The CUP1 promoter is the metalothionein gene promoter. It is activated by copper or silver ions added to the medium. The CUP1 gene is one of a few yeast genes that is present in yeast in more than one copy. Depending on the strain, there can be up to eight copies of this gene. The PHO5 promoter is a secreted gene coding for an acid phosphatase. It is induced by low or no phosphate in the medium. The phosphatase is secreted in the chance it will be able to free up some phosphate from the surroundings. When phosphate is present, no PHO5 message can be found. When it is absent, it is turned on strongly.

3. Yeast Transformation Protocols

A variety of approaches are available for transforming yeast cells and include electroporation, lithium acetate and protoplasting. In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Protoplast fusion has been used to overcome sexual barriers that prevent genetically unrelated strains from mating (Svoboda, 1976), thus facilitating the total or partial exchange of genetic components (Provost et al., 1978; Wilson et al., 1982; Perez et al., 1984; Spencer et al., 1985; Pina et al., 1986; Skala et al., 1988; Janderová et al., 1990; Gupthar, 1992; Molnar and Sipiczki, 1993). The process relies on cell wall digestion followed by fusion with, e.g., polyethylene glycol (Kao and Michayluk, 1974) and the protoplast adhesion promoter, $Ca^{2+}$, have been exploited in yeast fusion experiments (van Solingena and van der Plaat, 1977; Svoboda, 1978; Wilson et al., 1982; Pina et al., 1986). Other workers report "an enhancement of the protoplast fusion rate" using electrofusion techniques instead of polyethylene glycol (Weber et al., 1981; Halfmann et al., 1982). The action of polyethylene glycol is not specific. It catalyses the aggregation of protoplasts between the same or different species.

The fusion process may be summarized as follows: (i) random aggregation of protoplasts into clumps of various sizes (Anné and Peberdy, 1975; Sarachek and Rhoads, 1981); (ii) conversion of the aggregates into syncytia ("chimaeric protoplast fusion product") by dissolution of membranes and merging of cytoplasmic contents (Ahkong et al., 1975; Gumpert, 1980; Svoboda, 1981; Sarachek and Rhoads, 1981; Klinner and Böttcher, 1984); (iii) membrane reorganization (Ahkong et al., 1975; Gumpert, 1980) and fusion of nuclei heterokaryons (Sarachek and Rhoads, 1981; Klinner and Böttcher, 1984).

Another approach uses electroporation. Cells are first grown to a density of about $1 \times 10^7$/ml (OD595 ca. 0.5) in minimal medium (transformation frequency is not harmed by growth until early stationary phase (OD595=1.5)). Cells are harvested by spinning at 3000 rpm for 5 min at 20° C., followed by washing once in ice-cold water and harvesting; a second time in ice-cold 1M sorbitol. It has been reported (Suga and Hatakeyama, 2001), that 15 min incubation of these cells in the presence of DTT at 25 mM increases electrocompetence. The final resuspension is in ice-cold 1M sorbitol at a density of $1-5 \times 10^9$/ml. Forty µl of the cell suspension are added to chilled eppendorfs containing the DNA for transformation (100 ng) and incubated on ice for 5 min.

The electroporator may be set as follows: (a) 1.5 kV, 200 ohms, 25 uF (Biorad); (b) 1.5 kV, 132 ohms, 40 uF (Jensen/Flowgen). Cells and DNA are transferred to a pre-chilled cuvette and pulsed; 0.9 ml of ice-cold 1M sorbitol is then immediately added to the cuvette; the cell suspension is then returned to the eppendorf and placed on ice while other electroporations are carried out. Cells are plated as soon as possible onto minimal selective medium. Transformants should appear in 4-6 days at 32° C.

The following lithium acetate protocol is derived from Okazaki et al. (1990). High-frequency transformation method and library transducing vectors for cloning mammalian cDNAs by trans-complementation of *Schizosaccharomyces pombe*. Cells are grown in a 150 ml culture in minimal medium to a density of $0.5-1 \times 10^7$ cells/ml (OD595=0.2-0.5). Media with low glucose, or MB media (see Okazaki et al.), in which the cells are less happy, may increase transformation efficiency. Cells are harvested at 3000 rpm for 5 min at room temperature, then washed in 40 ml of sterile water and spun down as before. The cells are resuspended at $1 \times 10^9$ cells/ml in 0.1 M lithium acetate (adjusted to pH 4.9 with acetic acid) and dispensed in 100 µl aliquots into eppendorf tubes. Incubation is at 30° C. (25° C. for ts mutants) for 60-120 min. Cells will sediment at this stage. One µg of plasmid DNA in 15 µl TE (pH 7.5) is added to each tube and mix by gentle vortexing, completely resuspending cells sedimented during the incubation. The tubes should not be allowed to cool down at this stage. 290 µl of 50% (w/v) PEG 4000 prewarmed at 30° C. (25° C. for ts mutants) is added. Next, mix by gentle vortexing and incubate at 30° C. (25° C. for ts mutants) for 60 min. The tubes are heat shocked at 43° C. for 15 min, followed by cooling to room temperature for 10 min. The tubes are then centrifuged at 4000 rpm for 2 min in an eppendorf centrifuge. The supernatant is carefully removed by aspiration. Cells are resuspended in 1 ml of ½ YE broth by pepetting up and down with a pipetman P1000, transferred to a 50 ml flash and diluted with 9 ml of ½ YE. The cells are incubated with shaking at 32° C. (25° C. for ts mutants) for 50 min or longer. Aliquots of less than 0.3 ml are plated onto minimal plates. If necessary, cells are centrifuged at this stage and resuspended in 1 ml of medica to spread more cells on a plate.

VI. Screening Assays

1. Screening for Modulators of the Protein Function

The present invention further comprises methods for identifying modulators of human palmitoyl acyl transferase. These assays may comprise random screening of large libraries of candidate substances; alternatively, the assays may be used to focus on particular classes of compounds selected with an eye towards structural attributes that are believed to make them more likely to modulate the function of palmitoyl acyl transferase. By function, it is meant that one may assay for the transfer of palmitoyl groups to appropriate substrates.

To identify a modulator, one generally will determine the function of palmitoyl acyl transferase in the presence and absence of the candidate substance, a modulator defined as any substance that alters function. For example, a method generally comprises:

(a) providing a candidate modulator;

(b) admixing the candidate modulator with an isolated palmitoyl acyl transferase in vitro or with a cell that expressed a palmitoyl acyl transferase in vitro or in vivo;

(c) measuring palmitoyl acyl transferase activity; and (d) comparing the activity in step (c) with the activity in the absence of said candidate modulator, wherein a difference between the activities measured indicates that said candidate modulator is, indeed, a modulator of the compound, cell or animal.

It will, of course, be understood that all the screening methods of the present invention are useful in themselves notwithstanding the fact that effective candidates may not be found. The invention provides methods for screening for such candidates, not solely methods of finding them.

2. Modulators

As used herein the term "candidate substance" refers to any molecule that may potentially inhibit or enhance palmitoyl acyl transferase activity. The candidate substance may be a protein or fragment thereof, a small molecule, or even a nucleic acid molecule. It may prove to be the case that the most useful pharmacological compounds will be compounds that are structurally related to palmitoyl acyl transferase, or substrates therefor. Using lead compounds to help develop improved compounds is known as "rational drug design" and includes not only comparisons with known inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using any antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen a large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

3. In Vitro Assays

An effective in vitro assay should be rapid, relatively inexpensive and scalable. such assays generally are isolated molecules, can be run quickly and in large numbers, and thereby increase the amount of information obtainable in a short period of time. A variety of vessels may be used to run the assays, including test tubes, plates, dishes and other surfaces such as dipsticks or beads.

One example of a cell free assay is a binding assay. While not directly addressing function of palmitoyl acyl transferase, the ability of a modulator to bind to a palmitoyl acyl transferase complex in a specific fashion is strong evidence of a related biological effect. For example, binding of a molecule to a palmitoyl acyl transferase may, in and of itself, be inhibitory, due to steric, allosteric or charge-charge interactions. The target may be either free in solution, fixed to a support, or expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in PCT Publication WO 84/03564. Large numbers of small peptide test compounds are synthesized on a solid substrate, such as plastic pins or some other surface. Bound polypeptide is detected by various methods.

4. In Cyto and In Vivo Assays

The present invention also contemplates the screening of compounds for their ability to modulate palmitoyl acyl transferase in cells, as well as in multicellular organisms. Various cell lines can be utilized for such screening assays, including yeast cells specifically engineered for this purpose (discussed above). Depending on the assay, culture may be required (discussed above). The cell is examined using any of a number of different assays for palmitoyl acyl transferase function. Animal models may also be used, although the readouts may be more complex, such as systemic or behavioral.

VII. EXAMPLES

The following examples are included to further illustrate various aspects of the invention. It should be appreciated by those of skill in the art that the techniques disclosed in the examples that follow represent techniques and/or compositions discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Yeast and Bacterial Strains—The construction of yeast strains RJY1277 (MAT leu2 ura3 trp1 ade2 ade8 lys2 ras1::HIS3 erf2:TRP1 RAS2(CSext) (YCp52-RAS2)) and RJY543 (MATa.ura3 lys2 ade2 trp1 his3 leu2) has been described elsewhere (Bartels et al., 1999). GST-Erf4p and GST-Ras2p were expressed in yeast strain RJY543. Overexpression of FLAG-Erf2p was performed from the plasmid pESC (Stratagene) also in RJY543. FLAG-Erf2p and GST-Erf4p were expressed in bacterial strain XL1 Blue (Stratagene) from an operon fusion constructed from the pFLAG-MAC expression vector (Sigma). The FLAG epitope tag and GST moiety were fused in frame to the N-terminus of Erf2p and Erf4p, respectively.

Expression Plasmid Construction and Purification of Protein Substrates—All GST fusions were constructed from the galactose-inducible vector PEG(KG) (Mitchell et al., 1993). GST-Ras2CCaaX represents the complete Ras2 protein (38 kDa) fused to GST. GST-(HV)CCaaX consists of the C-terminal 35 amino acid residues of Ras2p fused to GST, and GST-(HV)ACaaX is the same construct except that $Cys^{318}$ has been mutated to Ala. GST-CCaaX consists of the C-terminal 5 amino acid residues of Ras2p fused to GST. Expression and purification of GST fusion proteins in yeast were performed as follows. Strain RJY543 was co-transformed with the indicated GST-Ras2p vector and pMA210, a plasmid that expressed GAL4 under the control of the ADH1 promoter (Ma and Ptashne, 1987). The culture was grown to an $A_{600}$ of 0.4-0.6 in synthetic media containing 2% ethanol, 2% glycerol as the carbon source. The cells were induced by the addition of galactose (4% final concentration) and incubated overnight at 25° C. Cells were centrifuged (750×g) for 10 min and lysed in a solution of Y-PER® (Pierce) containing 1 mM DTT, 1 mM EDTA, 0.1% Triton X-100, and 0.13 mM phenylmethylsulfonyl at room temperature (30-40 min). The yeast lysate was centrifuged at 2,000 rpm (750×g) (10 min), and GSH-agarose (Pierce) beads were added to the supernatant. The GSH-agarose beads were eluted (1 h, room temperature) with 20 mM glutathione in 50 mM Tris-HCl (pH 7.4), 0.02% Triton X-100, 10% glycerol. As expected, GST-RasCCaaX fusions were membrane-associated due to the prenylation of the CaaX box cysteine. Analysis of the Ras substrate by SDS-PAGE revealed that the GST-Ras protein is the major band present in the preparation. The minor binds cross-react with anti-GST antibody and are either free GST or a proteolytic product of the GST-Ras fusion (data not shown).

H-Ras was expressed as an N-terminal $His_6$-tagged fusion in Sf9 cells and purified from detergent extracts of membranes using nickel chelate affinity chromatography (Camp and Hofmann, 1993). The stoichiometry of palmitate on the purified substrate has not been determined, but a significant fraction is probably lost during purification due to the action of thioesterases and the presence of reducing agents in the buffers. Myristoylated $G_{i1}$ was purified from bacteria expressing N-myristoyl transferase (Mumby and Linder, 1994). $G_{i1}$ was reconstituted with nonprenylated G subunits purified from Sf9 cells in the assay (Dunphy et al., 2001).

Purification of Erf2p/Erf4p Complex—RJY543 yeast cells expressing GST-Erf4p along with FLAG-Erf2p or FLAG-Erf2p mutants (Erf2(H201A)p, Erf2(C189S)p, Erf2(C203S)p) were solubilized in Y-PER® reagent as described above. E. coli cells expressing GST-Erf4p along with FLAG-Erf2p or FLAG-Erf2p mutants (Erf2(H201A)p, Erf2(C203S)p) were lysed by high pressure (25,000 p.s.i.) homogenization (Avestin) in 50 mM Tris-HCl, pH 7.4, 150 mM NaCl, 1 mM DTT, 1 mM EDTA, and 0.13 mM phenylmethylsulfonyl fluoride (Buffer A). Extracts were centrifuged at 6000 rpm (2800×g) for 15 min to remove unbroken cells and debris. Triton X-100 (0.3% final) was added to the supernatants, and samples were incubated at room temp for 20 min. The cell lysates were then diluted with equal volumes of Buffer A to a final concentration of 0.15% Triton X-100. GST-Erf4p and FLAG-Erf2p (wild-type and mutants) fusion proteins were affinity-purified from yeast and bacterial cell extracts by binding to GSH-agarose or anti-FLAG M2 antibody agarose beads (Sigma). The beads were washed three times with 50 mM Tris-HCl (pH 7.4). The volume of the wash each time was at least 10 times the bead volume. The beads were taken up in 50 mM Tris-HCl (pH 7.4), 0.02% Triton X-100, and 10% glycerol. The ratio of GST-Erf4p to FLAG-Erf2p partially purified from either yeast or bacteria depended on whether GSH-agarose or M2 antibody-agarose beads were used (an example in shown in FIG. 2).

Purification of hE2-1(DHHC9)/hE4-1 From Insect Cells Infected with Recombinant Baculovirus—Purification of the hE2-1(DHHC9)/hE4-1 (hErf2/hErf4) complex from SF9 cells was performed at 4° C. and all buffers were supplemented with protease inhibitors (Aprotinin 2 µg/ml; leupeptin 100 µM; pepstatin 1 µM; and PMSF 1 mM). Insect SF9 cells ($1.5×10^6$/ml) were co-inoculated with high titer Baculovirus expressing either hErf2-Myc-His or GST-hErf4. After 72 h, the cells were collected and the cell pellet was suspended in nitrogen cavitation buffer (50 mM Tris, pH 7.4; 300 mM NaCl; 1 mM EDTA<10 mM β-Mercaptoethanol) for 30 min at 400 psi. The cell lysate was cleared by centrifugation at 700×g for 10 min and the resulting postnuclear supernatant was centrifuged at 100,000×g for 30 min. The P100 was suspended by syringe in extraction buffer (TNEMG; 50 mM, Tris pH 7.4; 300 mM NaCl; 0.1 mM EDTA, 10 mM β-mercaptoethanol; and 10% glycerol) containing 1% n-dodecyl-beta-D-maltoside (Dojindo), transferred to a Dounce homogenizer for 5 strokes, and incubated with end-over-end rotation for 1 h. The extract was cleared by centrifugation at 100,000×g for 30 min, diluted 1:2 in extraction buffer without dodecyl-maltoside, applied to 2.0 ml of nickel affinity resin Ni-NTA (Qiagen), and incubated with end-over-end rotation for 1 h. The resin was washed with twenty volumes of TNEMG with 0.5% dodecyl-maltoside and 5 mM imidazole pH 7.4, and eluted with 200 mM imidazole pH 7.4 in TNEMG containing 0.5% maltoside. The elution was applied to 2 ml of glutathione affinity resin (Sigma) and incubated with end-over-end rotation for 1 h. The resin was washed with five volumes TNEMG with 0.5% Dodecyl-maltoside, twice with five volumes TNEMG containing 0.1% Dodecyl-maltoside, and eluted with 10 mM glutathione in 3 ml of (TNEDG; 50 mM Tris, pH 7.4; 150 mM NaCl; 1 mM EDTA; 1 mM DTT; 10% glycerol) containing 0.1% dodecyl-maltoside.

Immunoblotting—Proteins bound to the GSH-agarose beads were analyzed for the presence of both GST and FLAG peptide fusion proteins. GST fusion proteins were detected by immunoblotting with rabbit anti-GST (Molecular Probes) antibody and peroxidase-conjugated goat anti-rabbit secondary antibody (Sigma). FLAG-tagged proteins were detected on western blots by probing with anti-FLAG® M5 monoclonal antibody (Sigma) and peroxidase-conjugated sheep anti-mouse secondary antibody (Amersham Biosciences). The presence of FLAG-Erf2p was determined by affinity purification on anti-FLAG antibody-agarose beads followed by an anti-FLAG immunoblot.

Ras PAT Assays—Ras PAT activity was assayed by measuring the incorporation of tritiated palmitate. [$^3$H]palmitoyl-CoA substrate was synthesized from [$^3$H]palmitic acid (NEN) and Coenzyme A using acyl-CoA synthetase (Sigma) and purified as described (Taylor et al., 1990). The PAT assay (25 µl of final volume) was performed by adding 1.5 µg of GST-Ras(HV)CCaaX(2 µM) to GST-Erf4p/FLAG-Erf2p GSH beads in 1 mM DTT, 100 mM MES (pH 6.3). The reaction was started by the addition of 1 µl of [$^3$H]palmitoyl-CoA (0.5 µM), incubated for 15 min at 30° C., and terminated by the addition of 5 µl of a 5× solution of SDS gel loading buffer without DTT. Heat inactivation was performed by boiling (100° C., 15 min) the GSH beads containing GST-Erf4p/FLAG-Erf2p prior to the addition of substrates. The assays were analyzed by SDS-PAGE using Bis-Tris gels, pH 6.4 (Nu-PAGE®), and subjected to fluorography as described (Mitchell et al., 1994). Quantitation of Ras PAT activity was done by excising Ras protein bands from the gel, solubilizing them in Soluene S-350 (Packard), and counting in a scintillation counter.

The following modifications to the Ras PAT assay were performed to determined the fold purification of the enzyme. Cells were lysed by three rounds of high pressure homogenization (Avestin Emulsiflex-C5) (yeast, 30,000 p.s.i.; bacteria 25,000 p.s.i.) in 50 mM Tris-HCl, pH 7.4, 150 mM NaCl, 1 mM DTT, 1 mM EDTA, and 0.13 mM phenylmethylsulfonyl fluoride (Buffer A). The extracts were centrifuged at 3000 rpm (700×g) (yeast) or 6000 rpm (2800×g) (bacteria) for 15 min to remove unbroken cells and debris. Triton X-100 (0.3% final) was added to the supernatants, and samples were incubated at room temp for 20 min. The cell lysates were then diluted with equal volumes of Buffer A to a final concentration of 0.15% Triton X-100. GSH-agarose was added, and samples were incubated overnight at 4° C. The beads were washed three times with 50 mM Tris-HCl (pH 7.4), and the beads were taken up in 50 mM Tris-HCl (pH 7.4), 0.02% Triton X-100, and 10% glycerol. Ras PAT activity present on the GSH beads or in the yeast and bacterial extracts were quantitated in a 30-µl assay containing 100 mM Tris-HCl, pH 8.0, 0.4 µM [$^3$H]palmitoyl-CoA, and 0.75 µg of GST-Ras (HV)CCaaX (0.83 µM). Protein concentrations were determined by Bradford assay (cell extracts) or modified Bradford dye-binding assay for GSH bead-bound protein (Bonde et al., 1992). Reactions were terminated by the addition of 5 µl of a 5× solution of SDS gel loading buffer without DTT. Heat inactivation was performed by boiling the GSH beads (100° Cm 15 min) containing GST-Erf4p/FLAG-Erf2p prior to substrate addition.

Example 2

Identification of the Yeast Erf2/Erf4 Palmitoyltransferase—Deletion of either ERF2 or ERF4 results in a nonviable strain when a palmitoylation-dependent Ras2 allele is the only Ras gene expressed (Mitchell et al., 1994) (FIG. 6A). The DHHC domain is required for Erf2p function; mutation of Cys$^{189}$ to Ser or His$^{201}$ to Ala abolishes Erf2p function. The phenotypes of single and double deletions of ERF2 and ERF4 mutant strains are indistinguishable suggesting that they function at the same step. Consistent with this prediction, FLAG-tagged Erf2p co-purifies with GST-Erf4p on a GSH-agarose affinity column (FIG. 6B) and GST-Erf4p co-purifies with FLAG-Erf2p using anti-FLAG antibody-agarose beads (data not shown). The level of Erf2p that is detected is reduced when isolated from erf4 cells, suggesting either that Erf4p is involved in the stability of Erf2p or our ability to extract Erf2p (FIG. 6B). Of the two loss-of-function alleles described above, Erf2(C189S)p, fails to interact with Erf4p, and the level of mutant protein detected is reduced. The other non-functional mutant protein, Erf2(H201A)p, is still able to interact with Erf4p (FIG. 6B).

To examine if the Erf2p and Erf4p complex is directly involved in the palmitoylation of Ras, the inventors performed an in vitro palmitoylation assay on the GSH-agarose-enriched Erf2p/Erf4p complex. A prenylated Ras substrate protein, Ras2-(HV)CCaaX, was purified from yeast as a GST fusion protein. The CaaX box of GST-Ras2(HV)CCaaX is prenylated, aax-proteolyzed, and carboxyl-methylated (Li et al., 2002). Incubation of Ras2p with bead-bound Erf2p/Erf4p in the presence of [$^3$H]palmitoyl-CoA led to incorporation of the label onto the Ras2p substrate (FIG. 6C). As expected of a protein-mediated reaction, incorporation of [$^3$H]palmitate is prevented by heating the beads (100° C., 15 min) prior to adding the substrates. In the presence of Erf2p/Erf4p, 0.14 µmol/min of plamitate was incorporated into the Ras2p substrate. This represents an acceleration of the spontaneous rate of ~160-fold.

Consistent with radiolabeling studies in vivo (Bartels et al., 1999), palmitoylation in vitro requires both Erf2p and Erf4p. Removal of either from the assay abolished Ras2p palmitoylation. The DHHC domain of Erf2p is also important for the palmitoylation reaction. Mutating Cys$^{189}$ or His$^{201}$ residues within the conserved DHHC domain of Erf2p abolished Ras PAT activity (FIG. 6C). The loss of Ras PAT activity observed with the Erf2(C189S)p mutant can be attributed to its absence from the complex (FIG. 6C). However, the loss of Ras PAT activity in the Erf2(H201A)p suggests that the conserved histidine of the DHHC signature sequence might play a more direct role catalyzing palmitate transfer. Mutation of Cys$^{318}$, the residue palmitoylated on Ras in vivo, to Ala also abolished palmitoylation in the in vitro Ras PAT assay. Palmitoylation of Ras2p is sensitive to treatment with hydroxylamine (1 M, pH 7.6, 30 min) as expected if the modification is a thioester linkage (data not shown).

Overexpression of GST-Erf4p and FLAG-Erf2p from high copy inducible plasmids results in detectable Ras PAT activity with a specific activity of 37 pmol/min/mg. Partial purification of GSH affinity beads increases the specific activity to 1300 pmol/min/mg, representing a 35-fold purification. The specific activity of the partially purified complex is an underestimate because FST-Erf4p is present in large excess over Erf2p. These data are consistent with the conclusion that the Erf2p/Erf4p complex itself constitutes the Ras PAT activity.

To rule out the possibility that PAT activity was co-purifying as a minor component of the yeast affinity purification, the inventors purified the Erf2p/Erf4p complex from *E. coli* expressing an operon fusion of FLAG-Erf2p and GST-Erf4p driven by the P$_{tac}$ promoter (FIGS. 7A-7C). Proteins are not modified with thioester-linked fatty acids in bacteria. As seen in FIG. 7B, Erf2p/Erf4β isolated from *E. coli* is able to carry out palmitoylation of Ras2p. The Erf2p/Erf4p activity purified from extracts exhibits the same heat sensitivity as the activity isolated from yeast. No Ras PAT activity is detected in *E. coli* not expressing ERF2 and ERF4. Total extracts expression the GST-Erf4p/FLAG-Erf2 operon fusion have Ras PAT activity of 4.5 pmol/min/mg. Purification by FSH-agarose affinity chromatography increases the specific activity to 340 pmol/min/mg or a 76-fold purification. The importance of the signature $^{200}$DHHC$^{203}$ motif of the DHHC is also evident in experiments with bacterially expressed Erf2p/Erf4p. FLAG-Erf2(H201A)p and FLAG-0Erf2(C203S)p can be co-purified with GST-Erf4p, but no Ras PAT activity above background levels is detected (FIGS. 7A-7C).

Erf2p appears to be directly involved in the transfer of palmitate to Ras based on the fact that wild-type FLAG-Erf2p becomes labeled in the presence of [$^3$H]palmitoyl-CoA (FIG. 8). Incubating Erf2p/Erf4p partially purified from yeast with [$^3$H]-palmitoyl-CoA in the absence of the Ras2(HV)CaaX substrate results in the formation of an acyl-enzyme intermediate (FIG. 8). Appearance of the tritium-labeled Erf2p was sensitive to heat inactivation, indicating that autopalmitoylation requires a native conformation of Erf2p. It was shown in FIGS. 6A-C and 7A-C that the DHHC signature in the DHHC domain of Erf2p is required for Ras PAT activity. This domain is also involved in the formation of the palmitoyl-Erf2p intermediate. Although the Erf4p-Erf2(H201A)p mutant does not display Ras PAT activity, it still forms the [$^3$H]palmitoylated Erf2(H201A)p acylbenzyme intermediate (FIG. 8). This suggests that His$^{201}$ may play a role in the transfer of plamitate from the acylated Erf2p to Ras. The conserved cysteine of the DHHC motif (Erf2C203Sp) behaves similarly to the Erf2 (H201A)p mutant, i.e., stable expression, co-purification with Erf4p, and loss of Ras PAT activity. However, unlike Erf2(H201A)p, the Erf2(C203S)p mutant protein does not form the palmitoylated enzyme intermediate (FIG. 8) suggesting that Cys$^{203}$ may be the site of palmitate attachment. Together, these results suggest that the Ras PAT reaction involves the formation of a [$^3$H]palmitoylated Erf2p acyl-enzyme intermediate prior to transfer of labeled palmitate to the Ras substrate. The significance of this demonstration of a DHHC intermediate is that the method can be applied to other DHHC proteins, and if an intermediate is observed, this would indicate that it was functioning as a PAT, even in the absence of a known substrate.

To begin to evaluate the protein substrate specificity of the Erf2p/Erf4p Ras PAT, full-length GST-RAs2 was compared with GST fused to the final 28 amino acid residues of the Ras2 hypervariable (HV) region. The HV domain is required for palmitoylation of Ras in vivo (Dong et al., 2003). Erf2p/Erf4p Ras PAT palmitoylated GST(HV)CCIIS to levels similar to full-length GST-Ras2CCIIS. Consistent with the importance of the hypervariable domain for substrate recognition, in vitro palmitoylation of GST-CCaaX is reduced 10-fold compared with GST-(HV)CCaaX. Next, the inventors examined whether yeast Ras PAT is able to palmitoylate mammalian H-Ras, which like yeast Ras, is farnesylated on a C-terminal CaaX box and palmitoylated on two adjacent cysteine residues. H-Ras was indeed palmitoylated by yeast Ras PAT but at levels much lower (5%) than the proposed natural substrate, Ras2p (40 vs 2720 pmol palmitate transferred/min/µmol substrate). The reduction in labeling could be due to differences between the H-Ras and yeast Ras2 hypervariable domains that the inventors show above is required for Ras PAT activity. Alternatively, it could be due to incomplete farnesylation of the H-Ras purified form Sf9 insect cells or to residual palmitate remaining on the purified H-Ras. The inventors also examined $G_{i1}$, a mammalian G-protein subunit, which is normally palmitoylated on a cysteine residue adjacent to a myristoylated N-terminal glycine. This substrate was produced in a strain expressing N-myristoyltransferase, resulting in a purified preparation that is stoichiometrically N-myristoylated (Mumby and Linder, 1994) but has not been palmitoylated in vivo. Ras PAT was able to palmitoylate the $G_{i1}$, but again, the level was ~5% that of yeast Ras2p (55 vs 2720 pmol palmitate transferred/min/µmol substrate). These results suggest that the Ras PAT is capable of palmitoylating other substrates but exhibits a strong preference for specific protein substrates.

Figure 17:
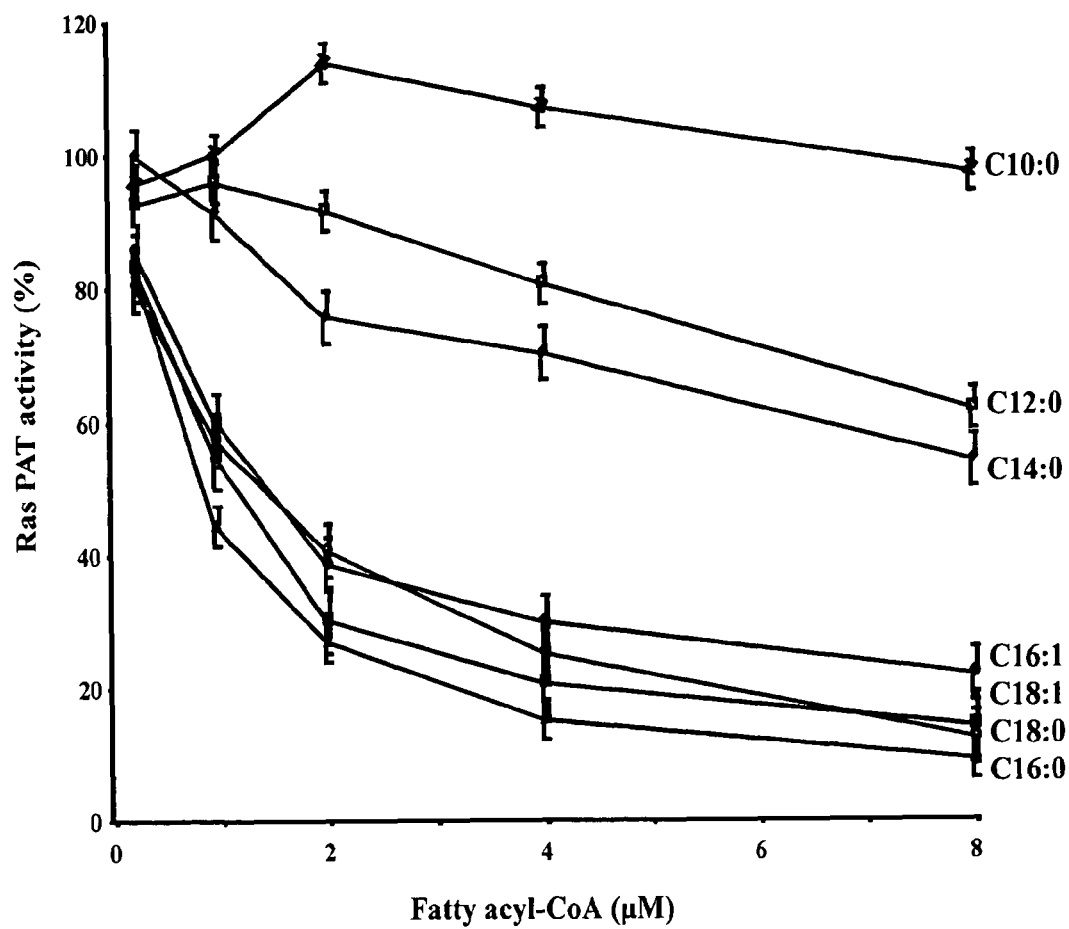
FIG. 17—Concentration dependent inhibition of yeast PAT activity by acyl-CoAs. Partially purified yeast Erf2p/Erf4p was assayed for PAT activity in the presence of 0.5 µM [$^3$H] palmitoyl-CoA and the indicated concentrations of unlabeled acyl-CoA substrates as indicated: decanoyl-CoA (C10:0), lauroyl-CoA (C12:0), myristoyl-CoA (C14:0) palmitoyl-CoA (C16:0), palmitoyleoyl-CoA (C16:1), stearoyl-CoA (C18:0), and oleoyl-CoA (C18:1). Radiolabeled palmitoylated GST-Ras(HV)CCaaX was excised from the gel and quantitated. Results are expressed as a percent of Ras PAT activity in the absence of competitor (100%).
Figure 18:
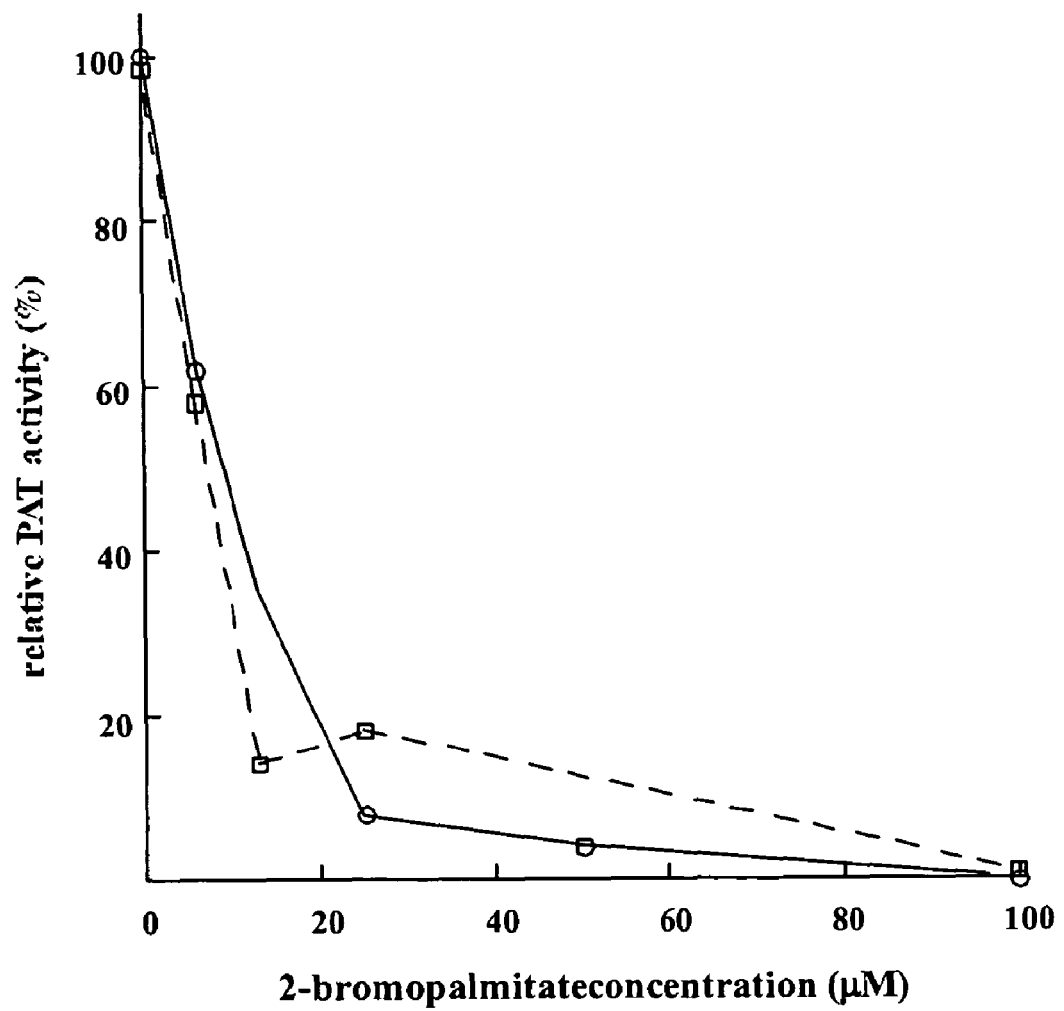
FIG. 18—Inhibition of Erf2p/Erf4p-dependent PAT by 2-bromopalmitate. Partially purified Erf2p/Erf4p was assayed for palmitoyltransferase activity using GST-Ras (HV)CCaaX (1.33 µM) and 0.5 µM [$^3$H]palmitoyl-CoA as substrate. Radiolabeled palmitoylated GST-Ras(HV)CCaaX was excised from the gel and quantitated. Results are expressed as a percent of Ras PAT activity in the absence of competitor (100%).

The lipid substrate specificity of Ras PAT was investigated by adding increasing amounts of unlabeled acyl-CoA competitors to the radioactive Ras PAT reaction. As expected, addition of unlabeled palmitoyl-CoA was the most effective competitor, achieving 90% inhibition at 8 µM, a 16-fold excess (FIG. 17). Decanoyl (C10:0) was ineffective at similar concentrations. Lauryl (12:0) and myristoyl (14:0) were more effective, but maximal inhibition required palmitoyl or longer acyl chain lengths. Both saturated and unsaturated fatty acyl-CoAs were effective inhibitors. Little difference was observed between C16:0 and C16:1, or C18:0 and C18:1. The lack of complete acyl-CoA substrate specificity of Ras PAT is consistent with the finding that thioester-linked fatty acids on protein are heterogeneous in vivo (Linder, 2001).

Isolation and Characterization of Human Palmitoyltransferases—Identification of the yeast Erf2/Erf4 PAT provided the information necessary to identify mammalian, including human, homologs of the Ras PAT. The sequence of yeast Erf2p was used to search for homologous sequences in humans. Putative Erf2 homologs are predicted to be integral membrane proteins with 4 transmembrane domains that contain a DHHC domain. Sequence alignments predict that DHHC9 (hE2-1), DHHC14, DHHC18, DHHC8, DHHC5, and DHHC19 have the highest sequence homology to Erf2 (FIG. 10A). In addition to the observed high degree of sequence homology observed within the DHHC domain of these four DHHC proteins, phylogenetics analysis reveals that DHHC9 (hE2-1), DHHC14, DHHC18, DHHC8, DHHC5, and DHHC19 fall within the same branch of the tree as yeast Erf2 (FIG. 10B).

A similar strategy was used to identify the mammalian homolog of Erf4. The yeast sequence was used to search for homologous sequences. Initial attempts to identify a putative homolog failed due to low sequence conservation. However, it was possible to identify other fungal homologs of Erf4 in A. nidulan and S. pombe. By using the S. cerevisiae and S. pombe sequences it was possible to identify a weak match with Erf4 in the human genome. The initial human sequence is named hE4-1. One other putative homolog (designated hE4-2) was identified using hE4-1 as the query sequence (FIG. 11).

Figure 14:
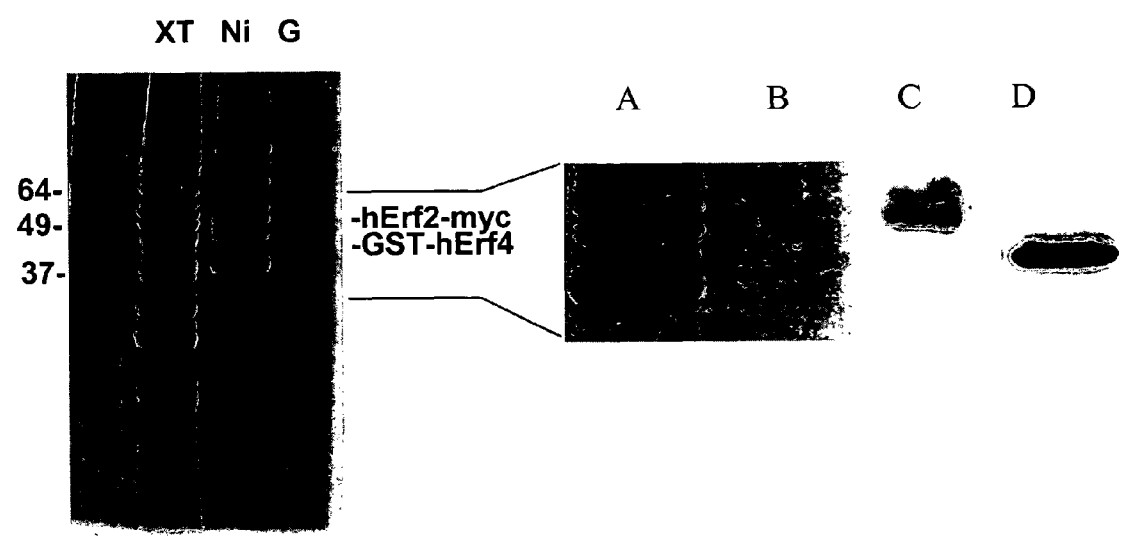
FIG. 14—Purification of hE2-1(DHHC9)/hE4-1 from insect cells. A detergent extract (XT) of membranes from SF9 cells expressing hErf2-myc (hE2-1/DHHC9) and GST-hErf4 (hE4-1) was cleared by centrifugation, and the hE2-1/hE4-1 complex was purified by sequential nickel chelate (Ni) and glutathione (G) affinity chromatography. The left panel is a Coomassie Blue stained gel. The right panel is an enlargement of the Ni and glutathione eluates of the same gel (A and B). Western blot analysis was performed with anti-myc (C) or anti-GST antibodies to confirm the identity of hE2-1 (DHHC9) and hE4-1, respectively.
Figure 16:
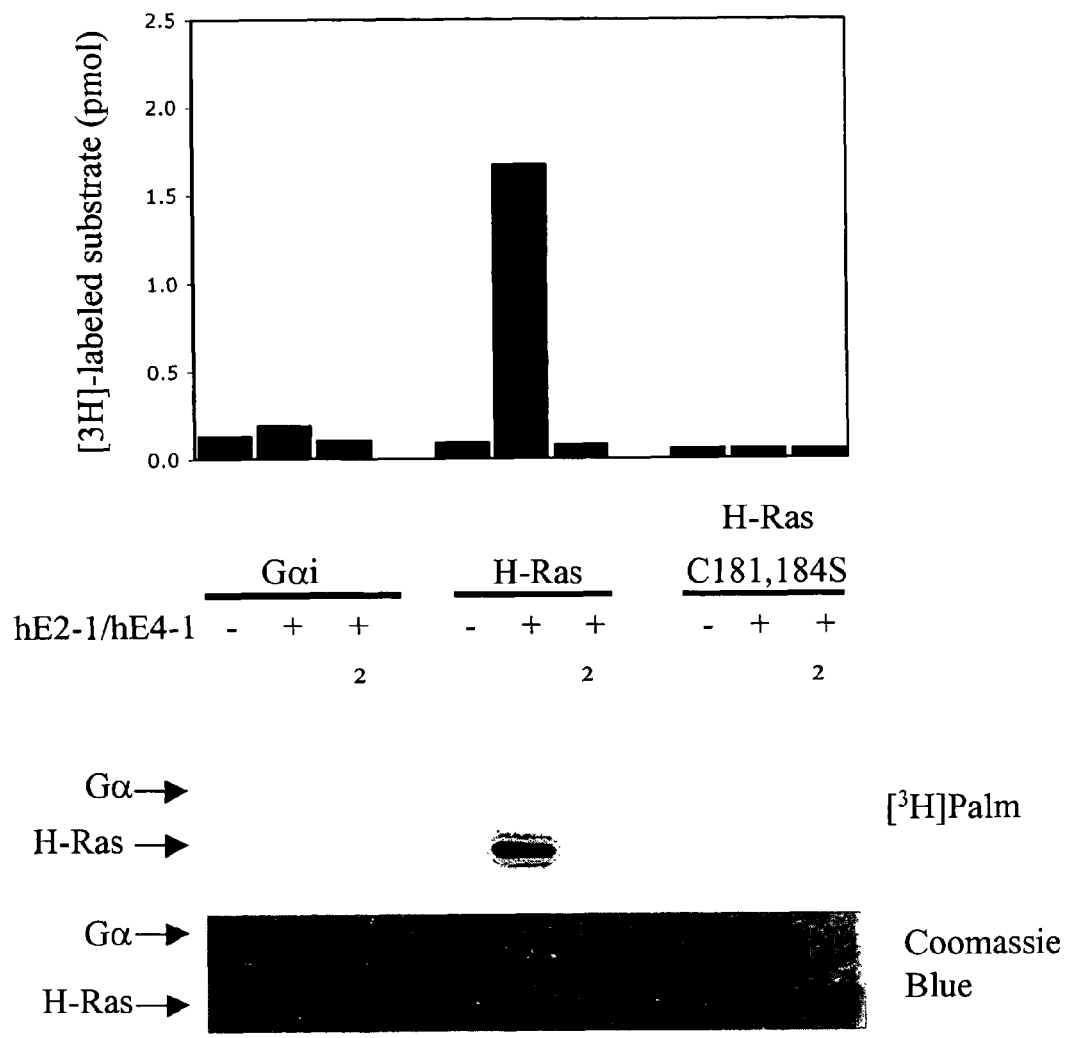
FIG. 16—Substrate specificity of hE2-1(DHHC9)/hE4-1 palmitoyltransferase activity. Gαi, H-Ras, or palmitoylation-defective H-Ras (C181,184S) were incubated in the absence or presence of purified hE2-1(DHHC9)/hE4-1 and [$^3$H] palmitoyl-CoA. A third reaction for each substrate contained heat-inactivated hE2-1/hE4-1(Δ). Reactions were resolved by SDS-PAGE and the gel stained with Coomassie Blue. Radioactive palmitate incorporation was visualized by fluorography ([$^3$H]Palm) or quantitated by scintillation counting (bar graph). hErf2 and hErf4 palmitoylation is faintly visible in the center lane of each set of reactions.

To test whether the human Erf2 and human Erf4 homologs of S. cerevisiae Erf2 and Erf4, respectively, posses PAT activity, the inventors expressed epitope-tagged versions of human E2-1(DHHC9) and hE4-1 proteins in mammalian tissue culture cells. As expected from studies in yeast, hE2-1 and hE4-1 co-immunoprecipitate (FIG. 13). Similar results were obtained when hexahistidine- and GST-tagged versions of the human proteins were expressed in insect cells using recombinant Baculovirus (not shown). The complex was purified from insect cells using metal chelate chromatography and glutathione agarose and the identity of the hE2-1(DHHC9) and hE4-1 confirmed by immunoblot (FIG. 14). The purified complex was tested for PAT activity using [$^3$H]palmitoyl-CoA. A time course of the palmitoyltransferase reaction is shown in FIG. 15. In the absence of added substrate, autoacylation of hE2-1(DHHC9) is observed. hE4-1 also becomes palmitoylated during the reaction. Palmitoylation of hE4-1 is dependent upon the presence of hE2-1 (DHHC9) (not shown). A characteristic of the autoacylation reaction is its rapid time course and appearance before hE4-1 palmitoylation. When the hE2-1(DHHC9)/hE4-1 complex is incubated with [$^3$H]palmitoyl-CoA and the human H-Ras substrate, H-Ras becomes palmitoylated (FIG. 15) at the appropriate cysteine residues. H-Ras(C181, 184S) that lacks the palmitoylated cysteines, is not a substrate for hE2-1/hE4-1 (FIG. 16). The hE2-1(DHHC9)/hE4-1 complex exhibits substrate specificity similar to the yeast Erf2p/Erf4p. Myristoylated $G_{i\alpha l}$ is not a substrate for the hE2-1 (DHHC9)/hE4-1 complex (FIG. 16).

Example 3

Methods have been established to screen for inhibitors of palmitoyl acyl transferases. The assay is based on the yeast Erf2/Erf4 PAT expressed and purified from yeast, bacteria, baculovirus, or cultured mammalian cell hosts or human hE2/hE4 similarly expressed and purified. The lipid donor for the PAT reaction is [$^3$H]- or [$^{14}$C]-palmitoyl-CoA. The palmitoyl acceptor is Erf2p (autopalmitoylation), a Ras protein or a fragment thereof, or a peptide based on the sequence of the Ras C-terminus. The method is easily adapted for other palmitoyl-protein substrates or DHHC-PATs.

Two types of assays are envisioned. The first takes place on a solid support, as described above. GST-Ras or fragments thereof are attached to glutathione agarose columns and the reaction product quantitated after washing. Quantitation can take the form of either scintillation counting or scintillation proximity assays (SPA). Putative inhibitors, synthetic or natural product chemical libraries can then be screened with the help of robotic high throughput methods.

Inhibition of autopalmitoylation or substrate palmitoylation can come about by substrates or substrate analogs. The inventors have used lipid substrates (acyl-CoAs) and putative lipid substrate analog (2-bromopalmitate) to demonstrate the feasibility of screening for modulators of human acyl transferase activity. The lipid substrate specificity of yeast Erf2p/Erf4p for Ras palmitoylation was investigated by adding increasing amounts of unlabeled acyl-CoA competitors to the radioactive Ras PAT reaction. As expected, addition of unlabeled palmitoyl-CoA was the most effective competitor, achieving 90% inhibition at μm, a 16-fold excess (FIG. 17). Decanoyl (C10:0) was ineffective at similar concentrations. Lauryl (12:0) and myristoyl (14:0) were more effective, but maximal inhibition required palmitoyl or longer acyl chain lengths. Both saturated and unsaturated fatty acyl-CoAs were effective inhibitors. Little difference was observed between C16:0 and C16:1, or C18:0 and C18:1. The lack of complete acyl-CoA substrate specificity of Ras PAT is consistent with the finding that thioester-linked fatty acids on protein are heterogeneous in vivo (Linder, 2001).

The non-metabolizable fatty acid, 2-Bromopalmitate (2-BP) has been reported to inhibit PAT activity in vivo (Webb et al., 2000). The enzymatic target of 2-BP inhibition was presumed to be PAT, but since the enzyme was not known until the present studies, there was no way to confirm that this was the case. The inventors tested whether 2-bromopalmitate could inhibit yeast Erf2p/Erf4p activity for Ras in vitro. As shown in FIG. 17, yeast PAT was purified as described above and a PAT assay performed in the presence or absence of increasing concentrations of 2-BP. 2-BP inhibits the Erf2/Erf4-dependent PAT activity using yeast Ras2 as a substrate. The concentration required for 50% inhibition of PAT enzyme in vitro agrees well with the inhibition of palmitoylation observed by Webb et al. (2000).

Figure 19:
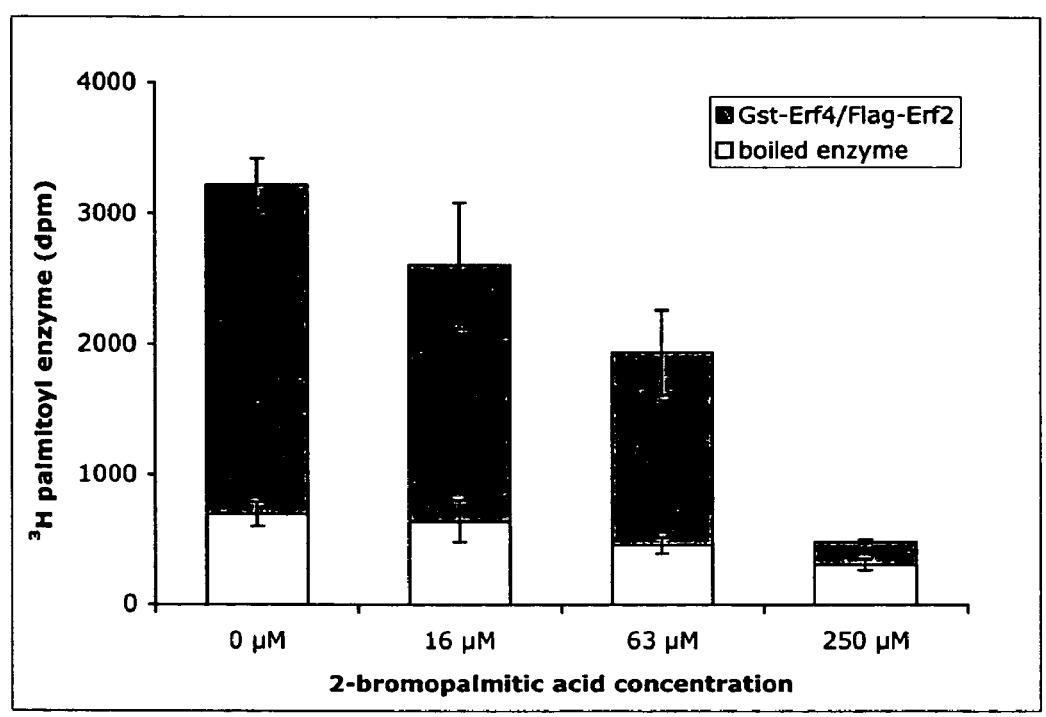
FIG. 19—Inhibition of autopalmitoylation of Erf2p. Partially purified Erf2p/GST-Erf4p (2.7 nM) was bound to the well of a GSH coated microtiter plate. The complex was incubated in reaction buffer (122 mM NaCl, 183 mM Tris HCl pH 7.8, 0.6 mM DTT and 0.035% Triton X-100) (registered trademark of Union Carbide Chemicals and Plastics Co., Inc. for a compound of formula $C_{14}H_{22}O(C_2H_4O)_n$ (CAS No. 9002-93-1); hereinafter referred to as "Triton X-100") in the presence or absence of 2-bromopalmitate (16 µM, 63 µM or 250 µM). The autopalmitoylation reaction was initiated by addition of 5 µl of 3 µM [$^3$H]palmitoyl CoA and the reaction was incubated for 30 minutes at 25° C. The wells were washed (3×200 µl 20 mM phosphate pH 6 with 1% Triton X-100) and 3×200 µl 25% ipa in water. Finally, wash with 2×200 µl 20 mM phosphate pH 6 with 150 mM NaCl. The wells were counted in scintillation fluid.

The inventors tested whether 2-BP inhibits autopalmitoylation of yeast Erf2p. When the purified Erf2p/Erf4p complex was incubated with [$^3$H]palmitoyl-CoA and increasing concentration of 2-BP, autopalmitoylation of Erf2p was inhibition in a dose-dependent manner (FIG. 19). These results demonstrate the feasibility of the method to screen for modulators of acyltransferase activity in the absence of a substrate.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from this concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope of the invention as defined by the appended claims.

VIII. REFERENCES

The following references, to the extent that they provide exemplary procedural or other details supplementary to those set forth herein, are specifically incorporated herein by reference:

U.S. Pat. No. 4,659,774
U.S. Pat. No. 4,682,195
U.S. Pat. No. 4,683,202
U.S. Pat. No. 4,683,202
U.S. Pat. No. 4,684,611
U.S. Pat. No. 4,816,571
U.S. Pat. No. 4,879,236
U.S. Pat. No. 4,952,500
U.S. Pat. No. 4,959,463
U.S. Pat. No. 5,141,813
U.S. Pat. No. 5,264,566
U.S. Pat. No. 5,302,523
U.S. Pat. No. 5,322,783
U.S. Pat. No. 5,384,253
U.S. Pat. No. 5,428,148
U.S. Pat. No. 5,464,765
U.S. Pat. No. 5,538,877
U.S. Pat. No. 5,538,880
U.S. Pat. No. 5,550,318
U.S. Pat. No. 5,554,744
U.S. Pat. No. 5,563,055
U.S. Pat. No. 5,574,146
U.S. Pat. No. 5,580,859
U.S. Pat. No. 5,589,466
U.S. Pat. No. 5,602,244
U.S. Pat. No. 5,610,042
U.S. Pat. No. 5,645,897
U.S. Pat. No. 5,656,610
U.S. Pat. No. 5,702,932
U.S. Pat. No. 5,705,629
U.S. Pat. No. 5,736,524
U.S. Pat. No. 5,780,448
U.S. Pat. No. 5,789,215
U.S. Pat. No. 5,871,986
U.S. Pat. No. 5,925,565
U.S. Pat. No. 5,928,906
U.S. Pat. No. 5,935,819
U.S. Pat. No. 5,945,100
U.S. Pat. No. 5,981,274
U.S. Pat. No. 5,994,624
Ahkong et al., Nature, 253:194-195, 1975
Almendro et al., J. Immunol., 157(12):5411-5421, 1996
Angel et al., Mol. Cell. Biol., 7:2256, 1987a
Angel et al., Cell, 49:729, 1987b
Anné and Peberdy, Archieves of Microbiol., 105:201-205, 1975
Atchison and Perry, Cell, 46:253, 1986
Atchison and Perry, Cell, 48:121, 1987
Ausubel et al., In: Current Protocols in Molecular Biology, John, Wiley & Sons, Inc., New York, 1996.

Banerji et al., Cell, 27(2 Pt 1):299-308, 1981.
Banerji et al., Cell, 33(3):729-740, 1983.
Bano et al., Biochem. J., 330:723-731, 1998.
Bartels et al., Mol. Cell. Biol., 19:6775-6787, 1999.
Bates, Mol. Biotechnol., 2(2):135-145, 1994.
Battraw and Hall, Theor. App. Genet., 82(2):161-168, 1991.
Berkhout et al., Cell, 59:273-282, 1989.
Berthiaume and Resh, J. Biol. Chem., 270:22399-22405, 1995.
Bhattacharjee et al., J. Plant Bioch. Biotech., 6(2):69-73, 1997.
Bizzozero et al., J. Biol. Chem., 262:13550-13557, 1987.
Blanar et al., EMBO J., 8:1139, 1989.
Bodine and Ley, EMBO J., 6:2997, 1987.
Bohm et al., Nucleic Acids Res., 25:2464-2469, 1997.
Bonde et al., Anal. Biochem., 200:195-198, 1992.
Boshart et al., Cell, 41:521, 1985.
Bosze et al., EMBO J., 5(7):1615-1623, 1986.
Bower et al., J. Plant, 2:409-416, 1992.
Braddock et al., Cell, 58:269, 1989.
Buising and Benbow, Mol. Gen. Genet., 243(1):71-81, 1994.
Bulla and Siddiqui, J. Virol., 62:1437, 1986.
Camp and Hofmann, J. Biol. Chem., 268:22566-22574, 1993.
Campbell and Villarreal, Mol. Cell. Biol., 8:1993, 1988.
Campere and Tilghman, Genes and Dev., 3:537, 1989.
Campo et al., Nature, 303:77, 1983.
Capaldi et al., Biochem. Biophys. Res. Comm., 74(2):425-433, 1977.
Carbonelli et al., FEMS Microbiol. Lett., 177(1):75-82, 1999.
Casa et al., Proc. Natl. Acad. Sci. USA, 90(23):11212-11216, 1993.
Celander and Haseltine, J. Virology, 61:269, 1987.
Celander et al., J. Virology, 62:1314, 1988.
Charmoun et al., Science, 293:2080-2084, 2001.
Chandler et al., Cell, 33:489, 1983.
Chandler et al., Proc. Natl. Acad. Sci. USA, 94(8):3596-601, 1997.
Chang et al., Mol. Cell. Biol., 9:2153, 1989.
Chatterjee et al., Proc. Natl. Acad. Sci. USA, 86:9114, 1989.
Chen and Okayama, Mol. Cell. Biol., 7(8):2745-2752, 1987.
Choi et al., Cell, 53:519, 1988.
Christou et al., Proc. Natl. Acad. Sci. USA, 84(12):3962-3966, 1987.
Clarke, Ann. Rev. Biochem., 61:355-386, 1992.
Cocea, Biotechniques, 23(5):814-816, 1997.
Cohen et al., J. Cell, Physiol., 5:75, 1987.
Costa et al., Mol. Cell. Biol., 8:81, 1988.
Cripe et al., EMBO J., 6:3745, 1987.
Culotta and Hamer, Mol. Cell. Biol., 9:1376, 1989.
Dandolo et al., J. Virology, 47:55-64, 1983.
De Villiers et al., Nature, 312(5991):242-246, 1984.
Deschamps et al., Science, 230:1174-1177, 1985.
D'Halluin et al., Plant Cell, 4(12):1495-1505, 1992.
Dong et al., Mol. Cell. Biol., 23(18):6574-6584, 2003.
Duncan and Gilman, J. Biol. Chem., 271:23594-23600, 1996.
Dunphy et al., Biochem. Biophys. Acta, 1485:185-198, 2001.
Dunphy et al., J. Biol. Chem., 271:7154-7159, 1996.
Dunphy et al., J. Biol. Chem., 276:43300-43304, 2001.
Edbrooke et al., Mol. Cell. Biol., 9:1908, 1989.
Edlund et al., Science, 230:912-916, 1985.
European Appln. 0273085
European Appln. 266,032
European Appln. 73,675A
Fechheimer et al., Proc. Natl. Acad. Sci. USA, 84:8463-8467, 1987.
Feng and Holland, Nature, 334:6178, 1988.
Firak and Subramanian, Mol. Cell. Biol., 6:3667, 1986.
Foecking and Hofstetter, Gene, 45(1):101-105, 1986.
Fraley et al., Proc. Natl. Acad. Sci. USA, 76:3348-3352, 1979.
Froehler et al., Nucleic Acids Res., 14(13):5399-5407, 1986.
Fujita et al., Cell, 49:357, 1987.
Ghosh and Bachhawat, In: Liver Diseases, Targeted Diagnosis and Therapy Using Specific Receptors and Ligands, We et al. (Eds.), Marcel Dekker, NY, 87-104, 1991.
Gilles et al., Cell, 33:717, 1983.
Gloss et al., EMBO J., 6:3735, 1987.
Godbout et al., Mol. Cell. Biol., 8:1169, 1988.
Goodbourn and Maniatis, Proc. Natl. Acad. Sci. USA, 85:1447, 1988.
Goodbourn et al., Cell, 45:601, 1986.
Gopal, Mol. Cell. Biol., 5:1188-1190, 1985.
Graham and Van Der Eb, Virology, 52:456-467, 1973.
Greene et al., Immunology Today, 10:272, 1989.
Grosschedl and Baltimore, Cell, 41:885, 1985.
Gumpert, Archives of Microbiol., 126:263-269, 1980.
Gupthat, J. Canadian Microbiol., 38:1233-1237, 1992.
Hagio et al., Plant Cell Rep., 10(5):260-264, 1991.
Halfmann et al., Current Genetics, 6:25-28, 1982.
Hancock et al., Cell, 63:133-139, 1990.
Harlan and Weintraub, J. Cell Biol., 101:1094-1099, 1985.
Haslinger and Karin, Proc. Natl. Acad. Sci. USA, 82:8572, 1985.
Hauber and Cullen, J. Virology, 62:673, 1988.
He et al., Plant Cell Reports, 14(2-3):192-196, 1994.
Hen et al., Nature, 321:249, 1986.
Hensel et al., Lymphokine Res., 8:347, 1989.
Hensgens et al., Plant Mol. Biol., 22(6):1101-1127, 1993.
Herr and Clarke, Cell, 45:461, 1986.
Hirochika et al., J. Virol., 61:2599, 1987.
Hirsch et al., Mol. Cell. Biol., 10:1959, 1990.
Holbrook et al., Virology, 157:211, 1987.
Horlick and Benfield, Mol. Cell. Biol., 9:2396, 1989.
Hou and Lin, Plant Physiology, 111:116, 1996.
Huang et al., Cell, 27:245, 1981.
Hug et al., Mol. Cell. Biol., 8:3065, 1988.
Hwang et al., Mol. Cell. Biol., 10:585, 1990.
Imagawa et al., Cell, 51:251, 1987.
Imbra and Karin, Nature, 323:555, 1986.
Imler et al., Mol. Cell. Biol., 7:2558, 1987.
Imperiale and Nevins, Mol. Cell. Biol., 4:875, 1984.
Inouye and Inouye, Nucleic Acids Res., 13: 3101-3109, 1985.
Jakobovits et al., Mol. Cell. Biol., 8:2555, 1988.
Jameel and Siddiqui, Mol. Cell. Biol., 6:710, 1986.
Janderová et al., J. Basic Microbiol., 30:499-505, 1990.
Jaynes et al., Mol. Cell. Biol., 8:62, 1988.
Johnson et al., Mol. Cell. Biol., 9:3393, 1989.
Jung et al., Mol. Cell. Biol., 15:1333-1342, 1995.
Kadesch and Berg, Mol. Cell. Biol., 6:2593, 1986.
Kaeppler et al., Plant Cell Reports, 9:415-418, 1990.
Kaneda et al., Science, 243:375-378, 1989.
Kao and Michayluk, Planta, 115:355-367, 1974.
Karin et al., Mol. Cell. Biol., 7:606, 1987.
Katinka et al., Cell, 20:393, 1980.
Kato et al., J. Biol. Chem., 266:3361-3364, 1991.
Kawamoto et al., Mol. Cell. Biol., 8:267, 1988.
Kiledjian et al., Mol. Cell. Biol., 8:145, 1988.
Klamut et al., Mol. Cell. Biol., 10:193, 1990.
Klein et al., Nature, 327:70-73, 1987.
Klinner and Böttcher, Zeitschrift für allgemeine Mikrobiologie, 24:539-544, 1984a.
Knittel et al., Plant Cell Reports, 14(2-3):81-86, 1994.
Koch et al., Mol. Cell. Biol., 9:303, 1989.
Kraus et al. FEBS Lett., 428(3):165-170, 1998.
Kriegler and Botchan, In: Eukaryotic Viral Vectors, Gluzman (Ed.), Cold Spring Harbor: Cold Spring Harbor Laboratory, NY, 1982.
Kriegler and Botchan, Mol. Cell. Biol., 3:325, 1983.

Kriegler et al., Cell, 38:483, 1984.
Kriegler et al., Cell, 53:45, 1988.
Kuhl et al., Cell, 50:1057, 1987.
Kunz et al., Nucl. Acids Res., 17:1121, 1989.
Lareyre et al., J. Biol. Chem., 274(12):8282-8290, 1999.
Larsen et al., Proc. Natl. Acad. Sci. USA, 83:8283, 1986.
Laspia et al., Cell, 59:283, 1989.
Latimer et al., Mol. Cell. Biol., 10:760, 1990.
Lazzeri, Methods Mol. Biol., 49:95-106, 1995.
Lee and Treisman, Curr. Biol., 11:1147-1152, 2001.
Lee et al., Biochem. Biophys. Res. Commun., 240(2):309-313, 1997.
Lee et al., Environ. Mol. Mutagen., 13(1):54-59, 1989.
Lee et al., Nature, 294:228, 1981.
Lee et al., Nucleic Acids Res., 12:4191-206, 1984.
Levenson et al., Hum. Gene Ther., 9(8):1233-1236, 1998.
Levinson et al., Nature, 295:79, 1982.
Li et al., J. Biol. Chem., 277:28870-28876, 2002.
Lin et al., Mol. Cell. Biol., 10:850, 1990.
Linder & Deschenese, Biochem 42(15):4311-20, 2003.
Linder, In: The Enzymes: Protein Lipidatio, Tamanoi and Sigman (Eds.), Vol. XXI:215-240, Academic Press, San Diego, 2001.
Liu et al., J. Biol. Chem., 271:23269-23276, 1996.
Liu et al., J. Biol. Chem., 274-3252, 1999.
Lobo et al., J. Biol. Chem., 277:41268-41273, 2002.
Luria et al., EMBO J., 6:3307, 1987.
Lusky and Botchan, Proc. Natl. Acad. Sci. USA, 83:3609, 1986.
Lusky et al., Mol. Cell. Biol., 3:1108, 1983.
Ma and Ptashne, Cell, 48:847-853, 1987.
Macejak and Sarnow, Nature, 353:90-94, 1991.
Majors and Varmus, Proc. Natl. Acad. Sci. USA, 80:5866, 1983.
Maniatis et al., Molecular Cloning, A Laboratory Manual, Cold Spring Harbor Press, Cold Spring Harbor, N.Y., 1990.
McCabe and Martinell, Bio-Technology, 11(5):596-598, 1993.
McNeall et al., Gene, 76:81, 1989.
Miksicek et al., Cell, 46:203, 1986.
Mitchell et al., J. Biol. Chem., 269:21540-21546, 1994.
Mitchell et al., Yeast, 9:715-72219, 1993.
Molnar and Sipiczki, Current Genetics, 24:45-52, 1993.
Mordacq and Linzer, Genes and Dev., 3:760, 1989.
Moreau et al., Nucl. Acids Res., 9:6047, 1981.
Muesing et al., Cell, 48:691, 1987.
Mumby and Linder, Methods Enzymol. 237:254-268, 1994.
Nabel et al., Science, 244(4910):1342-1344, 1989.
Ng et al., Nuc. Acids Res., 17:601, 1989.
Nicolau and Sene, Biochem. Biophys. Acta, 721:185-190, 1982.
Nicolau et al., Methods Enzymol., 149:157-176, 1987.
Nomoto et al., Gene, 236(2):259-271, 1999.
Ohta et al., J. Biol. Chem., 278:51957-51967, 2003.
Okazaki et al., Nucl. Acids Res., 18:6485-6489, 1990.
Omirulleh et al., Plant Mol. Biol., 21(3):415-28, 1993.
Ondek et al., EMBO J., 6:1017, 1987.
Ornitz et al., Mol. Cell. Biol., 7:3466, 1987.
Palmiter et al., Nature, 300:611, 1982.
PCT Publication WO 84/03564
PCT Publication WO 92/17598
PCT Publication WO 94/09699
PCT Publication WO 95/06128
Pech et al., Mol. Cell. Biol., 9:396, 1989.
Pelletier and Sonenberg, Nature, 334(6180):320-325, 1988.
Perales et al., Proc. Natl. Acad. Sci. USA, 91:4086-4090, 1994.
Perez et al., Current Genetics, 8:575-580, 1984.
Perez-Stable and Constantini, Mol. Cell. Biol., 10:1116, 1990.
Picard and Schaffner, Nature, 307:83, 1984.
Pina et al., Applied Environ. Microbiol., 51:995-1003, 1986.
Pinkert et al., Genes and Dev., 1:268, 1987.
Ponta et al., Proc. Natl. Acad. Sci. USA, 82:1020, 1985.
Porton et al., Mol. Cell. Biol., 10:1076, 1990.
Potrykus et al., Mol. Gen. Genet., 199:183-188, 1985.
Potter et al., Proc. Natl. Acad. Sci. USA, 81:7161-7165, 1984.
Provost et al., FEMS Microbiol. Lett., 3:309-312, 1978.
Putilina et al., Mol. Cell. Biochem., 195:219-226, 1999.
Queen and Baltimore, Cell, 35:741, 1983.
Quinn et al., Mol. Cell. Biol., 9:4713, 1989.
Redondo et al., Science, 247:1225, 1990.
Reisman and Rotter, Mol. Cell. Biol., 9:3571, 1989.
Resendez Jr. et al., Mol. Cell. Biol., 8:4579, 1988.
Rhodes et al., Methods Mol. Biol., 55:121-131, 1995.
Ripe et al., Mol. Cell. Biol., 9:2224, 1989.
Rippe et al., Mol. Cell. Biol., 10:689-695, 1990.
Ritala et al., Plant Mol. Biol., 24(2):317-325, 1994.
Rittling et al., Nuc. Acids Res., 17:1619, 1989.
Rosen et al., Cell, 41:813, 1988.
Roth et al., J. Cell. Biol., 159(1):23-28, 2002.
Sakai et al., Genes and Dev., 2:114, 1988.
Sambrook et al., In: Molecular Cloning, Cold Spring Harbor Laboratory Press, Cold Spring Harbor, N.Y., 2001.
Sarachek and Rhoads, Current Genetics, 4:221-222, 1981.
Satake et al., J. Virology, 62:970, 1988.
Schafer and Rine, Annu. Rev. Genet., 26:209-237, 1992.
Schaffner et al., J. Mol. Biol., 201:81, 1988.
Schlesinger et al., In: Lipid Modification of Proteins, Schlesinger (Ed.), 2-19, CRC Press, Boca Raton, Fla., 1993.
Schmidt and Burns, Biochem., Soc. Trans., 17:625-626, 1989.
Searle et al., Mol. Cell. Biol., 5:1480, 1985.
Sharp and Marciniak, Cell, 59:229, 1989.
Shaul and Ben-Levy, EMBO J., 6:1913, 1987.
Sherman et al., Mol. Cell. Biol., 9:50, 1989.
Singsit et al., Transgenic Res., 6(2):169-176, 1997.
Skala et al., Current Genetics, 13:101-104, 1988.
Sleigh and Lockett, J. EMBO, 4:3831, 1985.
Spalholz et al., Cell, 42:183, 1985.
Spandau and Le, J. Virology, 62:427, 1988.
Spandidos and Wilkie, EMBO J., 2:1193, 1983.
Spencer et al., Current Genetics, 9:649-652, 1985.
Stephens and Hentschel, Biochem. H., 248:1, 1987.
Stuart et al., Nature, 317:828, 1985.
Suga and Hatakeyama, Yeast, 18:1015-1021, 2001.
Sullivan and Peterlin, Mol. Cell. Biol., 7:3315, 1987.
Svoboda, Acta Histochemica, 23:211-217, 1981.
Svoboda, Archives of Microbiol., 110:313-318, 1976.
Svoboda, J. General Microbiol., 109:169-175, 1978.
Swartzendruber and Lehman, J. Cell, Physiology, 85:179, 1975.
Takebe et al., Mol. Cell. Biol., 8:466, 1988.
Tavernier et al., Nature, 301:634, 1983.
Taylor and Kingston, Mol. Cell. Biol., 10:165, 1990a.
Taylor and Kingston, Mol. Cell. Biol., 10:176, 1990b.
Taylor et al., Anal. Biochem., 184:311-316, 1990.
Taylor et al., J. Biol. Chem., 264:15160, 1989.
Thiesen et al., J. Virology, 62:614, 1988.
Tomes et al., Plant Mol. Biol., 14(2):261-268, 1990.
Torbet et al., Crop Science, 38(1):226-231, 1998.
Torbet et al., Plant Cell Reports, 14(10):635-640, 1995.
Treisman, Cell, 42:889, 1985.
Tronche et al., Mol. Biol. Med., 7:173, 1990.
Trudel and Constantini, Genes and Dev., 6:954, 1987.
Tsukada et al., Plant Cell Physiol., 30(4):599-604, 1989.
Tsumaki et al., J. Biol. Chem., 273(36):22861-22864, 1998.
Tur-Kaspa et al., Mol. Cell. Biol., 6:716-718, 1986.
Tyndell et al., Nuc. Acids Res., 9:6231, 1981.

Van Eck et al., Plant Cell Reports, 14(5):299-304, 1995.
van Solingen and van der Plaat, J. Bacteriology, 130:946-947, 1977.
Vannice and Levinson, J. Virology, 62:1305, 1988.
Vasseur et al., Proc. Natl. Acad. Sci. USA, 77:1068, 1980.
Wagner et al., Proc. Natl. Acad. Sci. USA 87(9):3410-3414, 1990.
Wang and Calame, Cell, 47:241, 1986.
Webb et al., J. Biol. Chem., 275, 261-70, 2000.
Weber et al., Cell, 36:983, 1984.
Weber et al., Current Genetics, 4:165-166, 1981.
Weinberger et al., Mol. Cell. Biol., 8:988, 1984.
Wilson et al., Molecular Genetics, 186:95-100, 1982.
Wilson et al., Science, 244:1344-1346, 1989.
Winoto and Baltimore, Cell, 59:649, 1989.
Wong et al., Gene, 10:87-94, 1980.
Wu and Wu, Adv. Drug Delivery Rev., 12:159-167, 1993.
Wu and Wu, Biochemistry, 27:887-892, 1988.
Wu and Wu, J. Biol. Chem., 262:4429-4432, 1987.
Wu et al., Biochem. Biophys. Res. Commun., 233(1):221-6, 1997.
Yang et al., Proc. Natl. Acad. Sci. USA, 87:9568-9572, 1990.
Yutzey et al., Mol. Cell. Biol., 9:1397, 1989.
Zhao-Emonet et al., Biochem. Biophys. Acta, 1442(2-3):109-119, 1998.
Zhou et al., Exp. Hematol, 21:928-933, 1993.

What is claimed is:

1. A method of screening for modulators of a human palmitoyltransferase, the method comprising: (a) providing an isolated, active human palmitoyltransferase protein complex comprising a protein having the amino acid sequence of SEQ ID NO: 7 (DHHC9) and the polypeptide of SEQ ID NO:14 (hE4-1) or a complex comprising SEQ ID NO:7 (DHHC 9) and the polypeptide of SEQ ID NO:15 (hE4-2) ; (b) contacting said human palmitoyltransferase complex with a candidate substance and a source of palmitate; and (c) measuring palmitate transfer to said palmitoyltransferase (autopalmitoylation) in the presence and absence of candidate substance, wherein a change in palmitate transfer to said human palmitoyltransferase, as compared to palmitate transfer to said human palmitoyltransferase in the absence of said candidate substance, indicates that said candidate substance is a modulator of human palmitoylation.

2. A method of screening for modulators of a human palmitoyltransferase, the method comprising: (a) providing an isolated, active human palmitoyltransferase protein complex comprising a protein having the amino acid sequence of SEQ ID NO: 9 (DHHC18) and the polypeptide of SEQ ID NO:14 (hE4-1) or a complex comprising SEQ ID NO: 9 (DHHC 18) and the polypeptide of SEQ ID NO:15 (hE4-2); (b) contacting said human palmitoyltransferase with a candidate substance and a source of palmitate complex; and (c) measuring palmitate transfer to said palmitoyltransferase (autopalmitoylation) in the presence and absence of candidate substance, wherein a change in palmitate transfer to said human palmitoyltransferase, as compared to palmitate transfer to said human palmitoyltransferase in the absence of said candidate substance, indicates that said candidate substance is a modulator of human palmitoylation.

3. The method of claim 1, wherein said palmitate comprises a label.

4. The method of claim 3, wherein said label is a radioactive label, a fluorescent label, a chemilluminescent label or a dye.

5. The method of claim 1, wherein measuring comprises scintillation counting, gel-based autoradiography, fluorimetry, or microtiter plate assay.

6. A method of screening for modulators of a human palmitoyltransferase comprising: (a) providing an isolated, active human palmitoyltransferase comprising a protein having the amino acid sequence of SEQ ID NO: 7 (DHHC9) and the polypeptide of SEQ ID NO:14 (hE4-1) or a complex comprising SEQ ID NO:7 (DHHC 9) and the polypeptide of SEQ ID NO:15 (hE4-2); (b) contacting said human palmitoyltransferase complex with a candidate substance, a source of palmitate, and a substrate capable of accepting palmitate; and (c) measuring palmitate transfer to said substrate in the presence and absence of candidate substance, wherein a change in palmitate transfer to said palmitoyltransferase or substrate, as compared to palmitate transfer to said palmitoyltransferase or substrate in the absence of said candidate substance, indicates that said candidate substance is a modulator of human palmitoylation.

7. A method of screening for modulators of a human palmitoyltransferase comprising: (a) providing an isolated, active human palmitoyltransferase comprising a protein having the amino acid sequence of SEQ ID NO: 9 (DHHC18) and the polypeptide of SEQ ID NO:14 (hE4-1) or a complex comprising SEQ ID NO: 9 (DHHC 18) and the polypeptide of SEQ ID NO:15 (hE4-2); (b) contacting said human palmitoyltransferase complex with a candidate substance, a source of palmitate, and a substrate capable of accepting palmitate; and (c) measuring palmitate transfer to said substrate in the presence and absence of candidate substance, wherein a change in palmitate transfer to said palmitoyltransferase or substrate, as compared to palmitate transfer to said palmitoyltransferase or substrate in the absence of said candidate substance, indicates that said candidate substance is a modulator of human palmitoylation.

8. The method of claim 6, wherein said palmitate comprises a label.

9. The method of claim 8, wherein said label is a radioactive label, a fluorescent label, a chemilluminescent label or a dye.

10. The method of claim 6, wherein said substrate is a Ras protein or fragment thereof.

11. The method of claim 6, wherein measuring comprises scintillation counting, gel-based autoradiography, fluorimetry, or microtiter plate assay.

12. A method of screening for modulators of a human palmitoyltransferase, the method comprising: (a) providing an isolated, active human palmitoyltransferase protein complex comprising a protein having the amino acid sequence of SEQ ID NO: 14 (hE4-1) and a protein selected from the group comprising SEQ ID NO: 7 (DHHC9) and the polypeptide of SEQ ID NO:9 (DHHC 18) or an isolated protein complex comprising a protein having the amino acid sequence of SEQ ID NO:15 (hE4-2) and SEQ ID NO: 9 DHHC 18; (b) contacting said human palmitoyltransferase complex with a candidate substance and a source of palmitate; and (c) measuring palmitate transfer to said palmitoyltransferase (autopalmitoylation) in the presence and absence of candidate substance, wherein a change in palmitate transfer to said human palmitoyltransferase, as compared to palmitate transfer to said human palmitoyltransferase in the absence of said candidate substance, indicates that said candidate substance is a modulator of human palmitoylation.

13. The method of claim 12, wherein said palmitate comprises a label.

14. The method of claim 13, wherein said label is a radioactive label, a fluorescent label, a chemilluminescent label or a dye.

15. The method of claim 12, wherein measuring comprises scintillation counting, gel-based autoradiography, fluorimetry, or microtiter plate assay.

* * * * *

SEQUENCE LISTING

<160> NUMBER OF SEQ ID NOS: 15

<210> SEQ ID NO 1
<211> LENGTH: 1080
<212> TYPE: DNA
<213> ORGANISM: Artificial Sequence
<220> FEATURE:
<223> OTHER INFORMATION: Description of Artificial Sequence: Synthetic Primer

<400> SEQUENCE: 1

```
atggccttgg tctctagaag gtcgacaaga tcggaaagca cctcaataac aaaggaagag      60
catacaggag aaggttcatt gacgaagttg ttcttccgat ggcttgttac cttggagggt     120
gatcaggata taaacgatgg aaaaggttat atatcgttac cgaatgtctc gaattatata     180
ttcttccttg gtggcaggtt caggacagta aagggcgcca aaccgttgtg gttaggtgtt     240
ctccttgcta ttgtatgtcc catggttctc ttctccatat ttgaggctca caaattgtgg     300 catcccaaa atggttataa agtgctggtc attttcttct attattttg ggtcataacg       360 ctagcatcct ttatcagaac agccactagt gatcctggcg ttcttccgag aaatattcat     420
ttaagtcaac taagaaataa ttatcagatc ccgcaagaat attacaactt gataacacta     480
ccaacacatt cttcaatttc aaaagacatt actatcaagt attgtccatc atgtaggata     540
tggagaccac ctcggtcttc tcactgttcc acatgtaacg tctgcgtaat ggttcatgac     600
caccattgca tatgggtcaa taattgcata ggaaaaagga actaccggtt cttttaata      660 ttcctgttag gtgcaatact ttcgtccgtc atattattaa ctaattgtgc catccatatt     720
gcacgggaat caggggggcc tcgcgattgt cccgttgcaa tattgttact ttgctatgca     780
gggctaacct tatggtatcc ggcaatactg tttacttatc acatatttat ggcaggtaat     840
cagcaaacaa caagggaatt tttgaaaggt attggatcga aaaaaaaccc tgtattccat     900
cgtgtggtca aggaggaaaa catatataat aagggtcct ttttgaaaaa tatgggtcac      960
ttgatgttag aaccaagggg cccaagcttt gtaagtgcca gaaagccaca tgaagctgga    1020
gattggagat ttatggattt atcgccagca cacagctttg aaaaaataca gaaatataa    1080
```

<210> SEQ ID NO 2
<211> LENGTH: 359
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 2

```
Met Ala Leu Val Ser Arg Arg Ser Thr Arg Ser Glu Ser Thr Ser Ile
1               5                   10                  15

Thr Lys Glu Glu His Thr Gly Glu Gly Ser Leu Thr Lys Leu Phe Phe
            20                  25                  30

Arg Trp Leu Val Thr Leu Glu Gly Asp Gln Asp Ile Asn Asp Gly Lys
        35                  40                  45

Gly Tyr Ile Ser Leu Pro Asn Val Ser Asn Tyr Ile Phe Phe Leu Gly
    50                  55                  60

Gly Arg Phe Arg Thr Val Lys Gly Ala Lys Pro Leu Trp Leu Gly Val
65                  70                  75                  80

Leu Leu Ala Ile Val Cys Pro Met Val Leu Phe Ser Ile Phe Glu Ala
                85                  90                  95

His Lys Leu Trp His Thr Gln Asn Gly Tyr Lys Val Leu Val Ile Phe
            100                 105                 110

Phe Tyr Tyr Phe Trp Val Ile Thr Leu Ala Ser Phe Ile Arg Thr Ala
        115                 120                 125

Thr Ser Asp Pro Gly Val Leu Pro Arg Asn Ile His Leu Ser Gln Leu
130                 135                 140

Arg Asn Asn Tyr Gln Ile Pro Gln Glu Tyr Tyr Asn Leu Ile Thr Leu
145                 150                 155                 160

Pro Thr His Ser Ser Ile Ser Lys Asp Ile Thr Ile Lys Tyr Cys Pro
                165                 170                 175

Ser Cys Arg Ile Trp Arg Pro Pro Arg Ser Ser His Cys Ser Thr Cys
            180                 185                 190

Asn Val Cys Val Met Val His Asp His His Cys Ile Trp Val Asn Asn
        195                 200                 205

Cys Ile Gly Lys Arg Asn Tyr Arg Phe Phe Leu Ile Phe Leu Leu Gly
210                 215                 220

Ala Ile Leu Ser Ser Val Ile Leu Leu Thr Asn Cys Ala Ile His Ile
225                 230                 235                 240

Ala Arg Glu Ser Gly Gly Pro Arg Asp Cys Pro Val Ala Ile Leu Leu
                245                 250                 255

Leu Cys Tyr Ala Gly Leu Thr Leu Trp Tyr Pro Ala Ile Leu Phe Thr
            260                 265                 270

Tyr His Ile Phe Met Ala Gly Asn Gln Gln Thr Thr Arg Glu Phe Leu
        275                 280                 285

Lys Gly Ile Gly Ser Lys Lys Asn Pro Val Phe His Arg Val Val Lys
290                 295                 300

Glu Glu Asn Ile Tyr Asn Lys Gly Ser Phe Leu Lys Asn Met Gly His
305                 310                 315                 320

Leu Met Leu Glu Pro Arg Gly Pro Ser Phe Val Ser Ala Arg Lys Pro
                325                 330                 335

His Glu Ala Gly Asp Trp Arg Phe Met Asp Leu Ser Pro Ala His Ser
            340                 345                 350

Phe Glu Lys Ile Gln Lys Ile
        355

<210> SEQ ID NO 3
<211> LENGTH: 714
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 3
```

```
atgtgcgata gccatcaaaa ggaagaagat aacgcaaata cgagcgaaag ggcgttattt    60
tttaattacc atgagttttc gtattcattc tacgaagacc tcggttccga agacgctaaa   120
cccacagagc acgacgaaga ccacaaattg tgtattacac atttcccgaa tgtgtatgct   180
gctcggggct ctgccgagtt ccaggtgacc cgggtggtac gagtgccccg cggttcgat    240
gagtctcgca gcagccttga aacgccacaa tttagtacac agcttcccgg tagcgagccg   300
gcggcaatcg tgggcgacga tggcactagc tttgtgcggt gcgggcgtta cgacattggg   360
gatcacgtgt ttggctgctc ctccgtctcg cctctgtcag aatatcttag tgcggcagag   420
ctcgcggagg ttgtgcaccg ggtaaacgga ttcttgctgc gtgaagaagg tgaggtgttc   480
gggtggcgta acttaagtgg cctgttgctc gatatgctta cgggcggtct gtggagctgg   540
gttttggggc cccttctttc tagacctgtg tttcaggagt ctctcgcgtt agagcagtac   600
gtggcgcagc taaactcgcc gggaggtctg cttcacgagc gcggtgtgcg cctagtattg   660
ccccgacggt ccgggtgcct atccctagat ttcgtcgtgc cccgacccaa atag         714
```

<210> SEQ ID NO 4
<211> LENGTH: 237
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Met Cys Asp Ser His Gln Lys Glu Glu Asp Asn Ala Asn Thr Ser Glu
1               5                   10                  15
Arg Ala Leu Phe Phe Asn Tyr His Glu Phe Ser Tyr Ser Phe Tyr Glu
            20                  25                  30
Asp Leu Gly Ser Glu Asp Ala Lys Pro Thr Glu His Asp Glu Asp His
        35                  40                  45
Lys Leu Cys Ile Thr His Phe Pro Asn Val Tyr Ala Ala Arg Gly Ser
    50                  55                  60
Ala Glu Phe Gln Val Thr Arg Val Val Arg Val Pro Arg Arg Phe Asp
65                  70                  75                  80
Glu Ser Arg Ser Ser Leu Glu Thr Pro Gln Phe Ser Thr Gln Leu Pro
                85                  90                  95
Gly Ser Glu Pro Ala Ala Ile Val Gly Asp Asp Gly Thr Ser Phe Val
            100                 105                 110
Arg Cys Gly Arg Tyr Asp Ile Gly Asp His Val Phe Gly Cys Ser Ser
        115                 120                 125
Val Ser Pro Leu Ser Glu Tyr Leu Ser Ala Ala Glu Leu Ala Glu Val
    130                 135                 140
Val His Arg Val Asn Gly Phe Leu Leu Arg Glu Glu Gly Glu Val Phe
145                 150                 155                 160
Gly Trp Arg Asn Leu Ser Gly Leu Leu Leu Asp Met Leu Thr Gly Gly
                165                 170                 175
Leu Trp Ser Trp Val Leu Gly Pro Leu Leu Ser Arg Pro Val Phe Gln
            180                 185                 190
Glu Ser Leu Ala Leu Glu Gln Tyr Val Ala Gln Leu Asn Ser Pro Gly
        195                 200                 205
Gly Leu Leu His Glu Arg Gly Val Arg Leu Val Leu Pro Arg Arg Ser
    210                 215                 220
Gly Cys Leu Ser Leu Asp Phe Val Val Pro Arg Pro Lys

```
225                 230                 235

<210> SEQ ID NO 5
<211> LENGTH: 1070
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 5

Ile Lys Tyr Cys Pro Ser Cys Arg Ile Trp Arg Pro Arg Ser Ser
  1               5                  10                  15

His Cys Ser Thr Cys Asn Val Cys Val Met Val His His Cys Ile
                 20                  25                  30

Trp Val Asn Asn Cys Ile Gly Lys Arg Asn Tyr Arg Phe Leu Ile
             35                  40                  45

Phe Leu Leu Lys Tyr Cys Phe Thr Cys Lys Met Phe Arg Pro Arg
 50                  55                  60

Thr Ser His Cys Ser Val Cys Asp Asn Cys Val Glu Arg Phe Asp His
 65                  70                  75                  80

His Cys Pro Trp Val Gly Asn Cys Val Gly Arg Arg Asn Tyr Arg Phe
                 85                  90                  95

Phe Tyr Ala Phe Ile Leu Lys Tyr Cys Tyr Thr Cys Lys Ile Phe Arg
                100                 105                 110

Pro Pro Arg Ala Ser His Cys Ser Ile Cys Asp Asn Cys Val Glu Arg
            115                 120                 125

Phe Asp His His Cys Pro Trp Val Gly Asn Cys Val Gly Lys Arg Asn
130                 135                 140

Tyr Arg Tyr Phe Tyr Leu Phe Ile Leu Lys Tyr Cys Phe Thr Cys Lys
145                 150                 155                 160

Ile Phe Arg Pro Pro Arg Ala Ser His Cys Ser Leu Cys Asp Asn Cys
                165                 170                 175

Val Glu Arg Phe Asp His His Cys Pro Trp Val Gly Asn Cys Val Gly
                180                 185                 190

Lys Arg Asn Tyr Arg Phe Phe Tyr Met Phe Ile Met Lys Trp Cys Ala
            195                 200                 205

Thr Cys His Phe Tyr Arg Pro Pro Arg Cys Ser His Cys Ser Val Cys
210                 215                 220

Asp Asn Cys Val Glu Asp Phe Asp His His Cys Pro Trp Val Asn Asn
225                 230                 235                 240

Cys Ile Gly Arg Arg Asn Tyr Arg Tyr Phe Phe Leu Phe Leu Met Lys
                245                 250                 255

Trp Cys Ala Thr Cys Arg Phe Tyr Arg Pro Pro Arg Cys Ser His Cys
                260                 265                 270

Ser Val Cys Asp Asn Cys Val Glu Glu Phe Asp His His Cys Pro Trp
            275                 280                 285

Val Asn Asn Cys Ile Gly Arg Arg Asn Tyr Arg Tyr Phe Phe Leu Phe
290                 295                 300

Leu Leu Gln Trp Cys Pro Lys Cys Cys Phe His Arg Pro Pro Arg Thr
305                 310                 315                 320

Tyr His Cys Pro Trp Cys Asn Ile Cys Val Glu Asp Phe Asp His His
                325                 330                 335

Cys Lys Trp Val Asn Asn Cys Ile Gly His Arg Asn Phe Arg Phe Phe
            340                 345                 350
```

-continued

```
Met Leu Leu Val Val Ser Ile Cys Lys Lys Cys Ile Tyr Pro Lys Pro
            355                 360                 365

Ala Arg Thr His His Cys Ser Ile Cys Asn Arg Cys Val Leu Lys Met
        370                 375                 380

Asp His His Cys Pro Trp Leu Asn Asn Cys Val Gly His Tyr Asn His
385                 390                 395                 400

Arg Tyr Phe Phe Ser Phe Cys Val Tyr Lys Cys Pro Lys Cys Cys Ser
                405                 410                 415

Ile Lys Pro Asp Arg Ala His His Cys Ser Val Cys Lys Arg Cys Ile
            420                 425                 430

Arg Lys Met Asp His His Cys Pro Trp Val Asn Asn Cys Val Gly Glu
        435                 440                 445

Asn Asn Gln Lys Tyr Phe Val Leu Phe Thr Ile Tyr Lys Cys Pro Lys
    450                 455                 460

Cys Cys Cys Ile Lys Pro Glu Arg Ala His His Cys Ser Ile Cys Lys
465                 470                 475                 480

Arg Cys Ile Arg Lys Met Asp His His Cys Pro Trp Val Asn Asn Cys
                485                 490                 495

Val Gly Glu Lys Asn Gln Arg Phe Phe Val Leu Phe Thr Ile Arg Tyr
            500                 505                 510

Cys Asp Arg Cys Gln Leu Ile Lys Pro Asp Arg Cys His His Cys Ser
        515                 520                 525

Val Cys Asp Lys Cys Ile Leu Lys Met Asp His His Cys Pro Trp Val
    530                 535                 540

Asn Asn Cys Val Gly Phe Ser Asn Tyr Lys Phe Phe Leu Leu Phe Leu
545                 550                 555                 560

Val Arg Phe Cys Asp Arg Cys His Leu Ile Lys Pro Asp Arg Cys His
                565                 570                 575

His Cys Ser Val Cys Ala Met Cys Val Leu Lys Met Asp His His Cys
            580                 585                 590

Pro Trp Val Asn Asn Cys Ile Phe Gly Ser Asn Tyr Lys Phe Phe Leu
        595                 600                 605

Gln Phe Leu Trp Glu Leu Cys Asn Lys Cys Asn Leu Met Arg Pro Lys
    610                 615                 620

Arg Ser His His Cys Ser Arg Cys Gly His Cys Val Arg Arg Met Asp
625                 630                 635                 640

His His Cys Pro Trp Ile Asn Asn Cys Val Gly Glu Asp Asn His Trp
                645                 650                 655

Leu Phe Leu Gln Leu Cys Leu Gln Tyr Cys Lys Val Cys Gln Ala Tyr
            660                 665                 670

Lys Ala Pro Arg Ser His His Cys Arg Lys Cys Asn Arg Cys Val Met
        675                 680                 685

Lys Met Asp His His Cys Pro Trp Ile Asn Asn Cys Cys Gly Tyr Gln
    690                 695                 700

Asn His Ala Ser Phe Thr Leu Phe Leu Leu Arg Arg Cys Arg Tyr Cys
705                 710                 715                 720

Leu Val Leu Gln Pro Leu Arg Ala Arg His Cys Arg Glu Cys Arg Arg
                725                 730                 735

Cys Val Arg Arg Tyr Asp His Cys Pro Trp Met Glu Asn Cys Val
            740                 745                 750

Gly Glu Arg Asn His Pro Leu Phe Val Val Tyr Leu Ser Ile Phe Cys
        755                 760                 765

Ser Thr Cys Leu Ile Arg Lys Pro Val Arg Ser Lys His Cys Gly Val
```

```
                    770                 775                 780
Cys Asn Arg Cys Ile Ala Lys Phe Asp His His Cys Pro Trp Val Gly
785                 790                 795                 800

Asn Cys Val Gly Ala Gly Asn His Arg Tyr Phe Met Gly Tyr Leu Asn
                805                 810                 815

Val Arg Cys Ser Thr Cys Asp Leu Arg Lys Pro Ala Arg Ser Lys His
                820                 825                 830

Cys Ser Val Cys Asn Trp Cys His Arg Phe Asp His His Cys Val
        835                 840                 845

Trp Val Asn Asn Cys Ile Gly Ala Trp Asn Ile Arg Tyr Phe Leu Ile
850                 855                 860

Tyr Val Arg Thr Phe Cys Thr Ser Cys Leu Ile Arg Lys Pro Leu Arg
865                 870                 875                 880

Ser Leu His Cys His Val Cys Asn Cys Val Ala Arg Tyr Asp Gln
                885                 890                 895

His Cys Leu Trp Thr Gly Arg Cys Ile Gly Phe Gly Asn His His Tyr
                900                 905                 910

Tyr Ile Phe Phe Leu Asp Leu His Cys Asn Leu Cys Asn Val Asp Val
                915                 920                 925

Ser Ala Arg Ser Lys His Cys Ser Ala Cys Asn Lys Cys Val Cys Gly
            930                 935                 940

Phe Asp His His Cys Lys Trp Leu Asn Asn Cys Val Gly Glu Arg Asn
945                 950                 955                 960

Tyr Arg Leu Phe Leu His Ser Val Asn Gln Phe Cys His Leu Cys Lys
                965                 970                 975

Val Ile Val Asn Lys Lys Thr Lys His Cys Ile Ser Cys Asn Lys Cys
                980                 985                 990

Val Ser Gly Phe Asp His His Cys Lys Trp Ile Asn Asn Cys Val Gly
            995                 1000                1005

Ser Arg Asn Tyr Trp Phe Phe Phe Ser Thr Val Glu Asp Trp Cys Ala
    1010                1015                1020

Lys Cys Gln Leu Val Arg Pro Ala Arg Ala Trp His Cys Arg Ile Cys
1025                1030                1035                1040

Gly Ile Cys Val Arg Arg Met Asp His His Cys Val Trp Tyr Ser Val
                1045                1050                1055

Ile Ile Thr Ala Gly Met Ala Tyr Ile Phe Leu Ile Gln Leu
                1060                1065                1070

<210> SEQ ID NO 6
<211> LENGTH: 359
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Met Ala Leu Val Ser Arg Arg Ser Thr Arg Ser Glu Ser Thr Ser Ile
1               5                   10                  15

Thr Lys Glu Glu His Thr Gly Glu Gly Ser Leu Thr Lys Leu Phe Phe
                20                  25                  30

Arg Trp Leu Val Thr Leu Glu Gly Asp Gln Asp Ile Asn Asp Gly Lys
            35                  40                  45

Gly Tyr Ile Ser Leu Pro Asn Val Ser Asn Tyr Ile Phe Phe Leu Gly
        50                  55                  60
```

-continued

```
Gly Arg Phe Arg Thr Val Lys Gly Ala Lys Pro Leu Trp Leu Gly Val
 65                  70                  75                  80

Leu Leu Ala Ile Val Cys Pro Met Val Leu Phe Ser Ile Phe Glu Ala
                 85                  90                  95

His Lys Leu Trp His Thr Gln Asn Gly Tyr Lys Val Leu Val Ile Phe
            100                 105                 110

Phe Tyr Tyr Phe Trp Val Ile Thr Leu Ala Ser Phe Ile Arg Thr Ala
        115                 120                 125

Thr Ser Asp Pro Gly Val Leu Pro Arg Asn Ile His Leu Ser Gln Leu
130                 135                 140

Arg Asn Asn Tyr Gln Ile Pro Gln Glu Tyr Tyr Asn Leu Ile Thr Leu
145                 150                 155                 160

Pro Thr His Ser Ser Ile Ser Lys Asp Ile Thr Ile Lys Tyr Cys Pro
                165                 170                 175

Ser Cys Arg Ile Trp Arg Pro Pro Arg Ser Ser His Cys Ser Thr Cys
            180                 185                 190

Asn Val Cys Val Met Val His Asp His His Cys Ile Trp Val Asn Asn
        195                 200                 205

Cys Ile Gly Lys Arg Asn Tyr Arg Phe Phe Leu Ile Phe Leu Leu Gly
210                 215                 220

Ala Ile Leu Ser Ser Val Ile Leu Leu Thr Asn Cys Ala Ile His Ile
225                 230                 235                 240

Ala Arg Glu Ser Gly Gly Pro Arg Asp Cys Pro Val Ala Ile Leu Leu
                245                 250                 255

Leu Cys Tyr Ala Gly Leu Thr Leu Trp Tyr Pro Ala Ile Leu Phe Thr
            260                 265                 270

Tyr His Ile Phe Met Ala Gly Asn Gln Gln Thr Thr Arg Glu Phe Leu
        275                 280                 285

Lys Gly Ile Gly Ser Lys Lys Asn Pro Val Phe His Arg Val Val Lys
290                 295                 300

Glu Glu Asn Ile Tyr Asn Lys Gly Ser Phe Leu Lys Asn Met Gly His
305                 310                 315                 320

Leu Met Leu Glu Pro Arg Gly Pro Ser Phe Val Ser Ala Arg Lys Pro
                325                 330                 335

His Glu Ala Gly Asp Trp Arg Phe Met Asp Leu Ser Pro Ala His Ser
            340                 345                 350

Phe Glu Lys Ile Gln Lys Ile
        355

<210> SEQ ID NO 7
<211> LENGTH: 382
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Met Phe Leu Leu Ser Cys Asn Arg Lys Thr His Phe Gly Ala Gly Ile
 1               5                  10                  15

Pro Ile Met Ser Val Met Val Arg Lys Lys Val Thr Arg Lys Trp
                 20                  25                  30

Glu Lys Leu Pro Gly Arg Asn Thr Phe Cys Cys Asp Gly Arg Val Met
            35                  40                  45

Met Ala Arg Gln Lys Gly Ile Phe Tyr Leu Thr Leu Phe Leu Ile Leu
        50                  55                  60
```

Gly Thr Cys Thr Leu Phe Phe Ala Phe Glu Cys Arg Tyr Leu Ala Val
 65                  70                  75                  80

Gln Leu Ser Pro Ala Ile Pro Val Phe Ala Met Leu Phe Leu Phe
             85                  90                  95

Ser Met Ala Thr Leu Leu Arg Thr Ser Phe Ser Asp Pro Gly Val Ile
             100                 105                 110

Pro Arg Ala Leu Pro Asp Glu Ala Ala Phe Ile Glu Met Glu Ile Glu
             115                 120                 125

Ala Thr Asn Gly Ala Val Pro Gly Tyr Gln Arg Pro Pro Arg Ile
130                 135                 140

Lys Asn Phe Gln Ile Asn Asn Gln Ile Val Lys Leu Lys Tyr Cys Tyr
145                 150                 155                 160

Thr Cys Lys Ile Phe Arg Pro Pro Arg Ala Ser His Cys Ser Ile Cys
                 165                 170                 175

Asp Asn Cys Val Glu Arg Phe Asp His His Cys Pro Trp Val Gly Asn
             180                 185                 190

Cys Val Gly Lys Arg Asn Tyr Arg Tyr Phe Tyr Leu Phe Ile Leu Ser
             195                 200                 205

Leu Ser Leu Leu Thr Ile Tyr Val Phe Ala Phe Asn Ile Val Tyr Val
210                 215                 220

Ala Leu Lys Ser Leu Lys Ile Gly Phe Leu Glu Thr Leu Lys Glu Thr
225                 230                 235                 240

Pro Gly Thr Val Leu Glu Val Leu Ile Cys Phe Phe Thr Leu Trp Ser
             245                 250                 255

Val Val Gly Leu Thr Gly Phe His Thr Phe Leu Val Ala Leu Asn Gln
             260                 265                 270

Thr Thr Asn Glu Asp Ile Lys Gly Ser Trp Thr Gly Lys Asn Arg Val
             275                 280                 285

Gln Asn Pro Tyr Ser His Gly Asn Ile Val Lys Asn Cys Cys Glu Val
             290                 295                 300

Leu Cys Gly Pro Leu Pro Pro Ser Val Leu Asp Arg Arg Gly Ile Leu
305                 310                 315                 320

Pro Leu Glu Glu Ser Gly Ser Arg Pro Pro Ser Thr Gln Glu Thr Ser
                 325                 330                 335

Ser Ser Leu Leu Pro Gln Ser Pro Ala Pro Thr Glu His Leu Asn Ser
             340                 345                 350

Asn Glu Met Pro Glu Asp Ser Ser Thr Pro Glu Glu Met Pro Pro Pro
             355                 360                 365

Glu Pro Pro Glu Pro Pro Gln Glu Ala Ala Glu Ala Glu Lys
             370                 375                 380

<210> SEQ ID NO 8
<211> LENGTH: 488
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Met Pro Pro Gly Gly Gly Pro Met Lys Asp Cys Glu Tyr Ser Gln
 1               5                  10                  15

Ile Ser Thr His Ser Ser Ser Pro Met Glu Ser Pro His Lys Lys Lys
             20                  25                  30

Lys Ile Ala Ala Arg Arg Lys Trp Glu Val Phe Pro Gly Arg Asn Lys

-continued

```
                35                  40                  45
Phe Phe Cys Asn Gly Arg Ile Met Met Ala Arg Gln Thr Gly Val Phe
 50                  55                  60

Tyr Leu Thr Leu Val Leu Ile Leu Val Thr Ser Gly Leu Phe Phe Ala
 65                  70                  75                  80

Phe Asp Cys Pro Tyr Leu Ala Val Lys Ile Thr Pro Ala Ile Pro Ala
                 85                  90                  95

Val Ala Gly Ile Leu Phe Phe Val Met Gly Thr Leu Leu Arg Thr
                100                 105                 110

Ser Phe Ser Asp Pro Gly Val Leu Pro Arg Ala Thr Pro Asp Glu Ala
                115                 120                 125

Ala Asp Leu Glu Arg Gln Ile Asp Ile Ala Asn Gly Thr Ser Ser Gly
130                 135                 140

Gly Tyr Arg Pro Pro Arg Thr Lys Glu Val Ile Ile Asn Gly Gln
145                 150                 155                 160

Thr Val Lys Leu Lys Tyr Cys Phe Thr Cys Lys Ile Phe Arg Pro Pro
                165                 170                 175

Arg Ala Ser His Cys Ser Leu Cys Asp Asn Cys Val Glu Arg Phe Asp
                180                 185                 190

His His Cys Pro Trp Val Gly Asn Cys Val Gly Lys Arg Asn Tyr Arg
                195                 200                 205

Phe Phe Tyr Met Phe Ile Leu Ser Leu Ser Phe Leu Thr Val Phe Ile
                210                 215                 220

Phe Ala Phe Val Ile Thr His Val Ile Leu Arg Ser Gln Gln Thr Gly
225                 230                 235                 240

Phe Leu Asn Ala Leu Lys Asp Ser Pro Ala Ser Val Leu Glu Ala Val
                245                 250                 255

Val Cys Phe Phe Ser Val Trp Ser Ile Val Gly Leu Ser Gly Phe His
                260                 265                 270

Thr Tyr Leu Ile Ser Ser Asn Gln Thr Thr Asn Glu Asp Ile Lys Gly
                275                 280                 285

Ser Trp Ser Asn Lys Arg Gly Lys Glu Asn Tyr Asn Pro Tyr Ser Tyr
290                 295                 300

Gly Asn Ile Phe Thr Asn Cys Cys Val Ala Leu Cys Gly Pro Ile Ser
305                 310                 315                 320

Pro Ser Leu Ile Asp Arg Arg Gly Tyr Ile Gln Pro Asp Thr Pro Gln
                325                 330                 335

Pro Ala Ala Pro Ser Asn Gly Ile Thr Met Tyr Gly Ala Thr Gln Ser
                340                 345                 350

Gln Ser Asp Met Cys Asp Gln Asp Gln Cys Ile Gln Ser Thr Lys Phe
                355                 360                 365

Val Leu Gln Ala Ala Thr Pro Leu Leu Gln Ser Glu Pro Ser Leu
370                 375                 380

Thr Ser Asp Glu Leu His Leu Pro Gly Lys Pro Gly Leu Gly Thr Pro
385                 390                 395                 400

Cys Ala Ser Leu Thr Leu Gly Pro Pro Thr Pro Pro Ala Ser Met Pro
                405                 410                 415

Asn Leu Ala Glu Ala Thr Leu Ala Asp Val Met Pro Arg Lys Asp Glu
                420                 425                 430

His Met Gly His Gln Phe Leu Thr Pro Asp Glu Ala Pro Ser Pro Pro
                435                 440                 445

Arg Leu Leu Ala Ala Gly Ser Pro Leu Ala His Ser Arg Thr Met His
450                 455                 460
```

```
Val Leu Gly Leu Ala Ser Gln Asp Ser Leu His Glu Asp Ser Val Arg
465                 470                 475                 480

Gly Leu Val Lys Leu Ser Ser Val
                485

<210> SEQ ID NO 9
<211> LENGTH: 388
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Met Lys Asp Cys Glu Tyr Gln Gln Ile Ser Pro Gly Ala Ala Pro Leu
  1               5                  10                  15

Pro Ala Ser Pro Gly Ala Arg Arg Pro Gly Pro Ala Ala Ser Pro Thr
                 20                  25                  30

Pro Gly Pro Gly Pro Ala Pro Pro Ala Ala Pro Ala Pro Pro Arg Trp
             35                  40                  45

Ser Ser Ser Gly Ser Gly Ser Gly Ser Gly Ser Leu Gly Arg
 50                  55                  60

Arg Pro Arg Arg Lys Trp Glu Val Phe Pro Gly Arg Asn Arg Phe Tyr
 65                  70                  75                  80

Cys Gly Gly Arg Leu Met Leu Ala Gly His Gly Gly Val Phe Ala Leu
                 85                  90                  95

Thr Leu Leu Leu Ile Leu Thr Thr Thr Gly Leu Phe Phe Val Phe Asp
                100                 105                 110

Cys Pro Tyr Leu Ala Arg Lys Leu Thr Leu Ala Ile Pro Ile Ile Ala
            115                 120                 125

Ala Ile Leu Phe Phe Phe Val Met Ser Cys Leu Leu Gln Thr Ser Phe
130                 135                 140

Thr Asp Pro Gly Ile Leu Pro Arg Ala Thr Val Cys Glu Ala Ala Ala
145                 150                 155                 160

Leu Glu Lys Gln Ile Asp Asn Thr Gly Ser Ser Thr Tyr Arg Pro Pro
                165                 170                 175

Pro Arg Thr Arg Glu Val Leu Ile Asn Gly Gln Met Val Lys Leu Lys
            180                 185                 190

Tyr Cys Phe Thr Cys Lys Met Phe Arg Pro Pro Arg Thr Ser His Cys
        195                 200                 205

Ser Val Cys Asp Asn Cys Val Glu Arg Phe Asp His His Cys Pro Trp
210                 215                 220

Val Gly Asn Cys Val Gly Arg Arg Asn Tyr Arg Phe Phe Tyr Ala Phe
225                 230                 235                 240

Ile Leu Ser Leu Ser Phe Leu Thr Ala Phe Ile Phe Ala Cys Val Val
                245                 250                 255

Thr His Leu Thr Leu Arg Ala Gln Gly Ser Asn Phe Leu Ser Thr Leu
            260                 265                 270

Lys Glu Thr Pro Ala Ser Val Leu Glu Leu Val Ile Cys Phe Phe Ser
        275                 280                 285

Ile Trp Ser Ile Leu Gly Leu Ser Gly Phe His Thr Tyr Leu Val Ala
    290                 295                 300

Ser Asn Leu Thr Thr Asn Glu Asp Ile Lys Gly Ser Trp Ser Ser Lys
305                 310                 315                 320

Arg Gly Gly Glu Ala Ser Val Asn Pro Tyr Ser His Lys Ser Ile Ile
```

```
                325                 330                 335
Thr Asn Cys Cys Ala Val Leu Cys Gly Pro Leu Pro Ser Leu Ile
            340                 345                 350

Asp Arg Arg Gly Phe Val Gln Ser Asp Thr Val Leu Pro Ser Pro Ile
            355                 360                 365

Arg Ser Asp Glu Pro Ala Cys Arg Ala Lys Pro Asp Ala Ser Met Val
        370                 375                 380

Gly Gly His Pro
385

<210> SEQ ID NO 10
<211> LENGTH: 419
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10

Met Pro Arg Ser Pro Gly Thr Arg Leu Lys Pro Ala Lys Tyr Ile Pro
 1               5                   10                  15

Val Ala Thr Ala Ala Leu Leu Val Gly Ser Ser Thr Leu Phe Phe
                20                  25                  30

Val Phe Thr Cys Pro Trp Leu Thr Arg Ala Val Ser Pro Ala Val Pro
            35                  40                  45

Val Tyr Asn Gly Ile Ile Phe Leu Phe Val Leu Ala Asn Phe Ser Met
        50                  55                  60

Ala Thr Phe Met Asp Pro Gly Val Phe Pro Arg Ala Asp Glu Asp Glu
65                  70                  75                  80

Asp Lys Glu Asp Asp Phe Arg Ala Pro Leu Tyr Lys Asn Val Asp Val
                85                  90                  95

Arg Gly Ile Gln Val Arg Met Lys Trp Cys Ala Thr Cys His Phe Tyr
            100                 105                 110

Arg Pro Pro Arg Cys Ser His Cys Ser Val Cys Asp Asn Cys Val Glu
        115                 120                 125

Asp Phe Asp His His Cys Pro Trp Val Asn Asn Cys Ile Gly Arg Arg
    130                 135                 140

Asn Tyr Arg Tyr Phe Phe Leu Phe Leu Leu Ser Leu Ser Ala His Met
145                 150                 155                 160

Val Gly Val Val Ala Phe Gly Leu Val Tyr Val Leu Asn His Ala Glu
                165                 170                 175

Gly Leu Gly Ala Ala His Thr Thr Ile Thr Met Ala Val Met Cys Val
            180                 185                 190

Ala Gly Leu Phe Phe Ile Pro Val Ile Gly Leu Thr Gly Phe His Val
        195                 200                 205

Val Leu Val Thr Arg Gly Arg Thr Thr Asn Glu Gln Val Thr Gly Lys
    210                 215                 220

Phe Arg Gly Gly Val Asn Pro Phe Thr Arg Gly Cys Cys Gly Asn Val
225                 230                 235                 240

Glu His Val Leu Cys Ser Pro Leu Ala Pro Arg Tyr Val Val Glu Pro
                245                 250                 255

Pro Arg Leu Pro Leu Ala Val Ser Leu Lys Pro Pro Phe Leu Arg Pro
            260                 265                 270

Glu Leu Leu Asp Arg Ala Ala Pro Leu Lys Val Lys Leu Ser Asp Asn
        275                 280                 285
```

```
Gly Leu Lys Ala Gly Leu Gly Arg Ser Lys Ser Lys Gly Ser Leu Asp
        290                 295                 300

Arg Leu Asp Glu Lys Pro Leu Asp Leu Gly Pro Pro Leu Pro Pro Lys
305                 310                 315                 320

Ile Glu Ala Gly Thr Phe Ser Ser Asp Leu Gln Thr Pro Arg Pro Gly
                325                 330                 335

Ser Ala Glu Ser Ala Leu Ser Val Gln Arg Thr Ser Pro Pro Thr Pro
                340                 345                 350

Ala Met Tyr Lys Phe Arg Pro Ala Phe Pro Lys Val Pro Phe Cys Gly
            355                 360                 365

Pro Gly Glu Gln Val Pro Gly Pro Asp Ser Leu Thr Leu Gly Asp Asp
    370                 375                 380

Ser Ile Arg Ser Leu Asp Phe Val Ser Glu Pro Ser Leu Asp Leu Pro
385                 390                 395                 400

Asp Tyr Gly Pro Gly Gly Leu His Ala Ala Tyr Pro Pro Ser Pro Pro
                405                 410                 415

Leu Ser Ala

<210> SEQ ID NO 11
<211> LENGTH: 423
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 11

Met Pro Ala Glu Ser Gly Lys Arg Phe Lys Pro Ser Lys Tyr Val Pro
1               5                   10                  15

Val Ser Ala Ala Ala Ile Phe Leu Val Gly Ala Thr Thr Leu Phe Phe
                20                  25                  30

Ala Phe Thr Cys Pro Gly Leu Ser Leu Tyr Val Ser Pro Ala Val Pro
            35                  40                  45

Ile Tyr Asn Ala Ile Met Phe Leu Phe Val Leu Ala Asn Phe Ser Met
    50                  55                  60

Ala Thr Phe Met Asp Pro Gly Ile Phe Pro Arg Ala Glu Glu Asp Glu
65                  70                  75                  80

Asp Lys Glu Asp Asp Phe Arg Ala Pro Leu Tyr Lys Thr Val Glu Ile
                85                  90                  95

Lys Gly Ile Gln Val Arg Met Lys Trp Cys Ala Thr Cys Arg Phe Tyr
                100                 105                 110

Arg Pro Pro Arg Cys Ser His Cys Ser Val Cys Asp Asn Cys Val Glu
            115                 120                 125

Glu Phe Asp His His Cys Pro Trp Val Asn Asn Cys Ile Gly Arg Arg
    130                 135                 140

Asn Tyr Arg Tyr Phe Phe Leu Phe Leu Leu Ser Leu Thr Ala His Ile
145                 150                 155                 160

Met Gly Val Phe Gly Phe Gly Leu Leu Tyr Val Leu Tyr His Ile Glu
                165                 170                 175

Glu Leu Ser Gly Val Arg Thr Ala Val Thr Met Ala Val Met Cys Val
            180                 185                 190

Ala Gly Leu Phe Phe Ile Pro Val Ala Gly Leu Thr Gly Phe His Val
    195                 200                 205

Val Leu Val Ala Arg Gly Arg Thr Thr Asn Glu Gln Val Thr Gly Lys
210                 215                 220
```

-continued

```
Phe Arg Gly Gly Val Asn Pro Phe Thr Asn Gly Cys Cys Asn Asn Val
225                 230                 235                 240

Ser Arg Val Leu Cys Ser Ser Pro Ala Pro Arg Tyr Leu Gly Arg Pro
                245                 250                 255

Lys Lys Glu Lys Thr Ile Val Ile Arg Pro Pro Phe Leu Arg Pro Glu
            260                 265                 270

Val Ser Asp Gly Gln Ile Thr Val Lys Ile Met Asp Asn Gly Ile Gln
        275                 280                 285

Gly Glu Leu Arg Arg Thr Lys Ser Lys Gly Ser Leu Glu Ile Thr Glu
290                 295                 300

Ser Gln Ser Ala Asp Ala Glu Pro Pro Pro Lys Pro Asp Leu
305                 310                 315                 320

Ser Arg Tyr Thr Gly Leu Arg Thr His Leu Gly Leu Ala Thr Asn Glu
                325                 330                 335

Asp Ser Ser Leu Leu Ala Lys Asp Ser Pro Thr Pro Thr Met Tyr
            340                 345                 350

Lys Tyr Arg Pro Gly Tyr Ser Ser Ser Thr Ser Ala Ala Met Pro
        355                 360                 365

His Ser Ser Ala Lys Leu Ser Arg Gly Asp Ser Leu Lys Glu Pro
370                 375                 380

Thr Ser Ile Ala Glu Ser Ser Arg His Pro Ser Tyr Arg Ser Glu Pro
385                 390                 395                 400

Ser Leu Glu Pro Glu Ser Phe Arg Ser Pro Thr Phe Gly Lys Ser Phe
                405                 410                 415

His Phe Asp Pro Leu Ser Ser
            420

<210> SEQ ID NO 12
<211> LENGTH: 282
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

Met Thr Leu Leu Thr Asp Ala Thr Pro Leu Val Lys Glu Pro His Pro
1               5                   10                  15

Leu Pro Leu Val Pro Arg Pro Trp Phe Leu Pro Ser Leu Phe Ala Ala
            20                  25                  30

Phe Asn Val Val Leu Leu Val Phe Phe Ser Gly Leu Phe Phe Ala Phe
        35                  40                  45

Pro Cys Arg Trp Leu Ala Gln Asn Gly Glu Trp Ala Phe Pro Val Ile
    50                  55                  60

Thr Gly Ser Leu Phe Val Leu Thr Phe Phe Ser Leu Val Ser Leu Asn
65                  70                  75                  80

Phe Ser Asp Pro Gly Ile Leu His Gln Gly Ser Ala Glu Gln Gly Pro
                85                  90                  95

Leu Thr Val His Val Val Trp Val Asn His Gly Ala Phe Arg Leu Gln
            100                 105                 110

Trp Cys Pro Lys Cys Cys Phe His Arg Pro Arg Thr Tyr His Cys
        115                 120                 125

Pro Trp Cys Asn Ile Cys Val Glu Asp Phe Asp His His Cys Lys Trp
    130                 135                 140

Val Asn Asn Cys Ile Gly His Arg Asn Phe Arg Phe Phe Met Leu Leu
145                 150                 155                 160
```

```
Val Leu Ser Leu Cys Leu Tyr Ser Gly Ala Met Leu Val Thr Cys Leu
            165                 170                 175

Ile Phe Leu Val Arg Thr Thr His Leu Pro Phe Ser Thr Asp Lys Ala
            180                 185                 190

Ile Ala Ile Val Ala Val Ser Ala Ala Gly Leu Leu Val Pro Leu
            195                 200                 205

Ser Leu Leu Leu Ile Gln Ala Leu Ser Val Ser Ser Ala Asp Arg
    210                 215                 220

Thr Tyr Lys Gly Lys Cys Arg His Leu Gln Gly Tyr Asn Pro Phe Asp
225                 230                 235                 240

Gln Gly Cys Ala Ser Asn Trp Tyr Leu Thr Ile Cys Ala Pro Leu Gly
                245                 250                 255

Pro Lys Ala Ala Ala Ser Trp Met Arg Leu Ala Ser Ala Ser Cys Arg
                260                 265                 270

Ala Lys Pro Trp Ala Val Cys Phe Pro Ser
            275                 280

<210> SEQ ID NO 13
<211> LENGTH: 237
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 13

Met Cys Asp Ser His Gln Lys Glu Glu Asp Asn Ala Asn Thr Ser Glu
  1               5                  10                  15

Arg Ala Leu Phe Phe Asn Tyr His Glu Phe Ser Tyr Ser Phe Tyr Glu
             20                  25                  30

Asp Leu Gly Ser Glu Asp Ala Lys Pro Thr Glu His Asp Glu Asp His
         35                  40                  45

Lys Leu Cys Ile Thr His Phe Pro Asn Val Tyr Ala Ala Arg Gly Ser
 50                  55                  60

Ala Glu Phe Gln Val Thr Arg Val Val Arg Val Pro Arg Arg Phe Asp
 65                  70                  75                  80

Glu Ser Arg Ser Ser Leu Glu Thr Pro Gln Phe Ser Thr Gln Leu Pro
                 85                  90                  95

Gly Ser Glu Pro Ala Ala Ile Val Gly Asp Asp Gly Thr Ser Phe Val
            100                 105                 110

Arg Cys Gly Arg Tyr Asp Ile Gly Asp His Val Phe Gly Cys Ser Ser
        115                 120                 125

Val Ser Pro Leu Ser Glu Tyr Leu Ser Ala Ala Glu Leu Ala Glu Val
    130                 135                 140

Val His Arg Val Asn Gly Phe Leu Arg Glu Glu Gly Glu Val Phe
145                 150                 155                 160

Gly Trp Arg Asn Leu Ser Gly Leu Leu Leu Asp Met Leu Thr Gly Gly
                165                 170                 175

Leu Trp Ser Trp Val Leu Gly Pro Leu Leu Ser Arg Pro Val Phe Gln
            180                 185                 190

Glu Ser Leu Ala Leu Glu Gln Tyr Val Ala Gln Leu Asn Ser Pro Gly
        195                 200                 205

Gly Leu Leu His Glu Arg Gly Val Arg Leu Val Leu Pro Arg Arg Ser
    210                 215                 220

Gly Cys Leu Ser Leu Asp Phe Val Val Pro Arg Pro Lys
```

```
225                 230                 235
```

<210> SEQ ID NO 14
<211> LENGTH: 137
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 14

```
Met Arg Pro Gln Gln Ala Pro Val Ser Gly Lys Val Phe Ile Gln Arg
 1               5                  10                  15

Asp Tyr Ser Ser Gly Thr Arg Cys Gln Phe Gln Thr Lys Phe Pro Ala
            20                  25                  30

Glu Leu Glu Asn Arg Ile Asp Arg Gln Gln Phe Glu Thr Val Arg
        35                  40                  45

Thr Leu Asn Asn Leu Tyr Ala Glu Ala Glu Lys Leu Gly Gly Gln Ser
    50                  55                  60

Tyr Leu Glu Gly Cys Leu Ala Cys Leu Thr Ala Tyr Thr Ile Phe Leu
65                  70                  75                  80

Cys Met Glu Thr His Tyr Glu Lys Val Leu Lys Val Ser Lys Tyr
                85                  90                  95

Ile Gln Glu Gln Asn Glu Lys Ile Tyr Ala Pro Gln Gly Leu Leu Leu
            100                 105                 110

Thr Asp Pro Ile Glu Arg Gly Leu Arg Val Ile Glu Ile Thr Ile Tyr
        115                 120                 125

Glu Asp Arg Gly Met Ser Ser Gly Arg
    130                 135
```

<210> SEQ ID NO 15
<211> LENGTH: 157
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 15

```
Met Gly Leu Thr Thr Asp Phe Leu Pro Tyr Glu Met Leu Leu Gly Pro
 1               5                  10                  15

Val Phe Thr Leu Leu Pro Val His Asn Leu Gln Glu Leu Arg Arg Ser
            20                  25                  30

Ala Ser Leu Ala Thr Lys Val Phe Ile Gln Arg Asp Tyr Ser Asp Gly
        35                  40                  45

Thr Ile Cys Gln Phe Gln Thr Lys Phe Pro Pro Glu Leu Asp Ser Arg
    50                  55                  60

Ile Glu Arg Gln Leu Phe Glu Glu Thr Val Lys Thr Leu Asn Gly Phe
65                  70                  75                  80

Tyr Ala Glu Ala Glu Lys Ile Gly Gly Ser Ser Tyr Leu Glu Gly Cys
                85                  90                  95

Leu Ala Cys Ala Thr Ala Tyr Phe Ile Phe Leu Cys Met Glu Thr His
            100                 105                 110

Tyr Glu Lys Val Leu Lys Lys Ile Ser Arg Tyr Ile Gln Glu Gln Asn
        115                 120                 125

Glu Lys Ile Phe Ala Pro Arg Gly Leu Leu Leu Thr Asp Pro Val Glu
    130                 135                 140
```

```
Arg Gly Met Arg Val Val Ser Phe Trp Ala Ile Leu Cys
145                 150                 155
```